US 7,901,894 B2

(12) United States Patent
Hangauer et al.

(10) Patent No.: US 7,901,894 B2
(45) Date of Patent: *Mar. 8, 2011

(54) KINASE INHIBITORS

(75) Inventors: David G. Hangauer, East Amherst, NY (US); Karen L. Milkiewicz, Exton, PA (US)

(73) Assignee: The Research Foundation of State University of New York, Amherst, NY (US)

(*) Notice: Subject to any disclaimer, the term of this patent is extended or adjusted under 35 U.S.C. 154(b) by 244 days.

This patent is subject to a terminal disclaimer.

(21) Appl. No.: 11/261,858

(22) Filed: Oct. 27, 2005

(65) Prior Publication Data

US 2006/0089401 A1    Apr. 27, 2006

Related U.S. Application Data

(63) Continuation of application No. 09/482,585, filed on Jan. 13, 2000, now Pat. No. 7,070,936.

(60) Provisional application No. 60/115,643, filed on Jan. 13, 1999.

(51) Int. Cl.
| G01N 33/53 | (2006.01) |
| C12Q 1/48 | (2006.01) |
| C12P 7/38 | (2006.01) |
| C07K 5/00 | (2006.01) |
| C07K 7/00 | (2006.01) |
| C07K 16/00 | (2006.01) |
| C07K 17/00 | (2006.01) |
| C07D 293/00 | (2006.01) |
| C07D 421/00 | (2006.01) |

(52) U.S. Cl. ............ 435/7.1; 435/15; 435/194; 530/334; 548/100

(58) Field of Classification Search .................... 435/7.1, 435/15, 194; 530/334; 548/100
See application file for complete search history.

(56) References Cited

U.S. PATENT DOCUMENTS

| 5,464,861 A | 11/1995 | Dobrusin et al. ............ 514/414 |
| 5,532,167 A | 7/1996 | Cantley et al. ................ 436/89 |
| 5,552,534 A | 9/1996 | Hirschmann et al. ........ 536/17.4 |
| 5,648,378 A | 7/1997 | Huang |
| 5,705,585 A | 1/1998 | Hogan, Jr. ...................... 527/200 |
| 5,736,412 A | 4/1998 | Zambias et al. |
| 6,011,175 A | 1/2000 | Scbti et al. .................... 562/557 |
| 6,420,338 B1 | 7/2002 | Schneider et al. ............ 514/12 |
| 6,552,066 B1 | 4/2003 | Sharpe et al. ................ 514/419 |
| 6,747,053 B2 | 6/2004 | Gabriel et al. |
| 7,005,445 B2 | 2/2006 | Hangauer, Jr. et al. ....... 514/419 |
| 7,070,936 B1 | 7/2006 | Hangauer, Jr. et al. ........ 435/7.1 |
| 7,129,225 B2 * | 10/2006 | Nicotera et al. ................ 514/64 |
| 7,141,596 B2 | 11/2006 | Combs et al. |
| 2003/0016615 A1 | 1/2003 | Lee et al. ................. 369/112.24 |
| 2004/0019015 A1 | 1/2004 | Nicotera et al. ............... 514/64 |
| 2005/0256159 A1 | 11/2005 | Barton et al. |
| 2006/0030544 A1 | 2/2006 | Hangauer, Jr. et al. ......... 514/80 |
| 2006/0122197 A1 | 6/2006 | Yao et al. |
| 2006/0172971 A1 | 8/2006 | Nicotera et al. ................ 514/64 |
| 2008/0004241 A1 * | 1/2008 | Hangauer ....................... 514/80 |

FOREIGN PATENT DOCUMENTS

| DE | 43 07 883 A1 | 9/1993 |
| EP | 0 370 381 A2 | 5/1990 |
| EP | 0 463 638 B1 | 1/1992 |
| EP | 0 846 464 A2 | 6/1998 |
| EP | 0974584 A1 | 1/2000 |
| JP | S45-39538 | 12/1970 |
| WO | WO 91/09849 | 7/1991 |
| WO | WO 96/35805 | 11/1996 |
| WO | WO 96/39384 | 12/1996 |
| WO | WO 96/39385 | 12/1996 |
| WO | WO 97/29091 | 8/1997 |
| WO | WO 98/07695 | 2/1998 |
| WO | WO 98/27108 | 6/1998 |
| WO | WO 9915500 A1 | 4/1999 |
| WO | WO 99/34018 | 7/1999 |
| WO | WO 99/48868 | 9/1999 |
| WO | WO-9954309 A1 | 10/1999 |
| WO | WO-9959973 A1 | 11/1999 |
| WO | WO-0042213 A1 | 7/2000 |
| WO | WO-0116097 A1 | 3/2001 |
| WO | WO 01/53274 A1 | 7/2001 |
| WO | WO 01/55111 | 8/2001 |
| WO | WO-0160814 A2 | 8/2001 |
| WO | WO 01/85726 A1 | 11/2001 |
| WO | WO 01/98290 A2 | 12/2001 |
| WO | WO 02/00661 A1 | 1/2002 |
| WO | WO 02/04459 A1 | 1/2002 |
| WO | WO 02/072548 A2 | 9/2002 |
| WO | WO 02/080926 | 10/2002 |

(Continued)

OTHER PUBLICATIONS

Terent'ev et al., Chemistry of Heterocyclic Compounds. p. 455; Apr. 23, 1966.*
Pigulla et al., Archiv der Pharmazie. vol. 312(1): 12-18; 1979.*
Kuehm-Caubere et al., J. Med. Chem. vol. 40: 1201-1210; 1997.*
Huang et al., "Polyhydroxylated 3-(N-Phenyl) Carbamoyl-2-Iminochromene Derivatives as Potent Inhibitors of Tyrosine Kinase p60$^{c\text{-}src}$", Bioorganic & Medicinal Chemistry Letters 5(20):2423-2428 (1995).
Casnellie et al. Adv. Enzyme Regul., 22:501-515 (1984).
Engström et al. Meth. Enzymol., 107:130-154 (1984).
Fukunaga et al. Protein Phosphorylation, Second Edition, Chapter 13, pp. 291-313 (1999).
Kemp et al. TIBS, 15:342-346 (1990).
Kemp et al. Meth. Enzymol., 200:121-134 (1991).
Marsilje et al. Bioorg. Med. Chem. Lett., 10:477-481 (2000).
Metfalf III et al. Curr. Pharm. Design, 8:2049-2075 (2002).

(Continued)

Primary Examiner — Sue Liu
(74) Attorney, Agent, or Firm — Mintz Levin Cohn Ferris Glovsky and Popeo, P.C.; Ivor R. Elrifi; Heidi A. Erlacher

(57) ABSTRACT

The present invention provides a method for identifying inhibitors of protein kinases. Methods are also provided for inhibiting protein kinase activity. Specific non-peptide protein tyrosine kinase inhibitors are provided. The protein kinases produced using the method of the present invention may be used to treat a number of conditions in patients, including cancer, psoriasis, atherosclerosis, or immune system activity.

9 Claims, 15 Drawing Sheets

FOREIGN PATENT DOCUMENTS

| WO | WO 02/080926 A1 | 10/2002 |
|---|---|---|
| WO | WO-03086385 | 3/2003 |
| WO | WO 03/093297 | 11/2003 |
| WO | WO 03/093297 A2 | 11/2003 |
| WO | WO-2004022525 A1 | 3/2004 |
| WO | WO 2004/056774 A2 | 7/2004 |
| WO | WO 2005/032493 A2 | 4/2005 |
| WO | WO 2007/026920 A2 | 3/2007 |

OTHER PUBLICATIONS

Milkiewicz et al. *Bioorg. Med. Chem. Lett.*, 10:483-486 (2000).
Pearson et al. *Meth. Enzymol.*, 200:62-81 (1991).
Ruzzene et al. *Protein Phosphorylation*, Second Edition, Chapter 10, pp. 221-253 (1999).
Sawyer *Expert Opin. Investig. Drugs*, 13(1):1-19 (2004).
Shoichet *Nature*, 432:862-865 (2004).
Songyang et al. *Meth. Mol. Biol.*, 87:87-98 (1998).
Sparks et al. *Int. J. Biochem.*, 18(6)497-504 (1986).
Chemical Abstracts vol. 67, No. 1 (1967) abstract No. 1850x (Chi-Ting Chou) p. 166 & Yao Hsueh Ao, vol. 13, No. 6 (1966).
Hoover et al. *J. Med. Chem.*, 41(16):2934-2938 (1998).
Patent Abstracts of Japan vol. 013, No. 384 (1989) & JP 01 132579 A (SS Pharmaceut. CO. LTD.) abstract only (1989).
Poulain et al. *J. Med. Chem.*, 44(21):3378-3390 (2001).
Romero et al. *J. Med. Chem.*, 37(7):999-1014 (1994).
Supplementary Partial European Search Report for EP 02 77 3833, mailed Sep. 29, 2005.
Al-Obeidi et al., "Protein Tyrosine Kinases: Structure, Substrate Specificity, and Drug Discovery", *Biopoly*, 47:197-223 (1998).
Bishop et al., "Screening a Hydroxystilbene Library for Selective Inhibition of the B Cell Antigen Receptor Kinase Cascade", *Tetrahedron*, 53(35):11995-12004 (1997).
Budde et al., "Discovery, Development, and Testing of Substrates and Inhibitors of $PP60^{C-SRC}$", *Int. J. Pharmacognosy*, 33:27-34 (1995).
Dolle, R. E., "Discovery of enzyme inhibitors through combinatorial chemistry", *Mol. Diversity*, 2:223-236 (1996).
Lawrence et al., "Protein Kinase Inhibitors: The Tyrosine-Specific Protein Kinases", *Pharmacol. Ther.*, 77(2):81-114 (1998).
Norman et al., "A Structure-Based Library Approach to Kinase Inhibitors", *J. Am. Chem. Soc.*, 118:7430-7431 (1996).
Stahura et al., "Molecular scaffold-based design and comparison of combinatorial libraries focused on the ATP-binding site of protein kinases", *J. Mol. Graphics Modelling*, 17:1-9 (1999).
Sun et al., "CombiDOCK: Structure-based combinatorial docking and library design", *J. Computer-Aided Mol. Des.*, 12:597-604 (1998).
Taylor et al., "Protein kinase inhibition: natural and synthetic variations on a theme", *Curr. Opin. Chem. Biol.*, 1:219-226 (1997).
Tegge et al., "Analysis of protein kinase substrate specificity by the use of peptide libraries on cellulose paper (SPOT-Method)", *Meth. Mol. Biol.*, 87:99-106 (1998).
Alfaro-Lopez et al. *J. Med. Chem.*, 41:2252-2260 (1998).
Burke et al. *J. Med. Chem.*, 36(4):425-432 (1993).
Burke, et al. *Acc. Chem. Res.*, 36:426-433 (2003).
Choi "Development of a Cellular Mimetic Protein Kinase Assay and a Novel Methodology for Determining the Mode of Inhibition for Multisubstrate" thesis, Bell & Howell Co., Aug. 1999.
Faltynek et al. *Biochem.*, 34:12404-12410 (1995).
Fry et al. *Science*, 265:1093-1095 (1994).
Hanke et al. *J Biol. Chem.*, 271(2):695-701 (1996).
Hsiao et al. *Synthesis*, pp. 1043-1046 (1998).
Hubbard *EMBO J.*, 16(18):5572-5581 (1997).
Johnson, et al., *Nature Reviews*, 1:696-709 (2002).
Kim et al. *Int. J. Peptide Protein Res.*, 44:457-465 (1994).
Lai et al. *J. Org. Chem.*, 61:1872-1874 (1996).
Lai et al. *J. Peptide Res.*, 51:271-281 (1998).
Levitzki et al. *Science*, 267:1782-1788 (1995).
Levitzki, *Acc. Chem. Res.*, 36:462-469 (2003).
Lou et al. *Bioorg. Med. Chem.*, 4(5):677-682 (1996).
McCluskey, et al. *J. Med Chem.*, 45:1151-1175 (2002).
Mohammadi et al. *Science*, 276:955-960 (1997).
Nair et al. *J. Med. Chem.*, 38:4276-4283 (1995).
Nair et al. *Synthesis*, pp. 810-814 (1995).
Patrick et al. *DDT*, 1(8):325-330 (1996).
Pestell, et al. *Oncogene*, 19:6607-6612 (2000).
Ramdas et al. *Arch. Biochem. Biophys.*, 323(2):237-242 (1995).
Rewcastle et al. *J. Med. Chem.*, 39:1823-1835 (1996).
Saperstein et al. *Biochem.*, 28:5694-5701 (1989).
Sawutz et al. *Biochem. Pharmacol.*, 51:1631-1638 (1996).
Showalter et al. *Pharmacol. Ther.*, 76(1-3):55-71 (1997).
Susa, et al., *TiPS*, 21:489-495 (2000).
Thakkar et al. *J. Med. Chem.*, 36:2950-2955 (1993).
Xu et al. *Nature*, 385:595-602 (1997).
Zhang, *Annu. Rev. Pharmacol. Toxicol.*, 42:209-234 (2002).
Zheng et al. *Biochem.*, 32:2154-2161 (1993).
"Amersham Pharmacia Biotech to Market and Distribute BioFocus' SoftFocus(TM) Kinase Libraries in North America," News release: Nov. 23, 1999.
Abram et al., "Src Family Tyrosine Kinases and Growth Factor Signaling," *Experimental Cell Research*, 254:1-13 (2000).
Bakhtiar et al., "Quantification of the Anti-Leukemia Drug STI1571 (Gleevec) and its Metabolite (CGP 74588) in Monkey Plasma Using a Semi-Automated Solid Phase Extraction Procedure and Liquid Chromatography-Tandem Mass Spectrometry," *Journal of Pharmaceutical & Biomedical Analysis*, 28(6):1183-1194 (2002).
Biscardi et al., "c-Src, Receptor Tyrosine Kinases and Human Cancer," *Advances in Cancer Research*, 61-119 (1999).
Biscardi et al., "Tyrosine Kinase Signaling in Breast Cancer: Epidermal Growth Factor Receptor and c-Src Interactions in Breast Cancer." *Breast Cancer Res.*, 2:203-210 (2000).
Blume-Jensen et al., "Oncogenic Kinase Signaling," *Nature*, 411:355-365 (2001).
Bridges, "Chemical Inhibitors of Protein Kinases," *Chemical Reviews*, 101(8):2541-2571 (2001).
Davidson et al., "Discovery and characterization of a substrate selective p38α inhibitor", *Biochemistry*, 43:11658-11671 (2004).
Druker, "STI571 (Gleevec) as a Paradigm for Cancer Therapy," *Trends in Molecular Medicine*, 8(4 Suppl):S14-18 (2002) (Abstract).
Duong, et al., "Inhibition of Osteoclast Function by Adenovirus Expressing Antisense Protein-tyrosine Kinase 2*", *J Biol. Chem.* 276:7484-7492 (2001).
Frame, "Src in Cancer: Deregulation and Consequences for Cell Behavior," *Biochemica et Biophysica Acta*, 1602:114-130 (2002).
Fretz et al., "Structure-based Design of Compounds Inhibiting Grb2-SH2 Mediated Protein-Protein Interactions in Signal Transduction Pathways," *Current Pharmaceutical Design*, 6(18):1777-1796 (2000) (Abstract).
Garcia-Echeverria et al., "ATP Site-Directed Competitive and Irreversible Inhibitors of Protein Kinases," *Med. Res. Rev.*, 20(1):28-57 (2000).
Garcia-Echeverria, "Antagonists of the Src Homology 2 (SH2) Domains of Grb2, Src, Lck and ZARP-70," *Current Medicinal Research*, 8(13):1589-1604 (2001) (Abstract).
Guo, et al., "Tyrosine Phosphorylation of the NR2B Subunit of the NMDA Receptor in the Spinal Cord during the Development and Maintenance of Inflammatory Hyperalgesia" *J. Neurosci.* 22:6208-6217 (2002).
Hadjeri, et al., "Antimitotic Activity of 5-Hydroxy-7-methoxy-2-phenyl-4-quinolones", *J. Med. Chem.* 47:4964-4970 (2004).
Haskell et al., "c-Src Tyrosine Phosphorylation of Epidermal Growth Factor Receptor, P190 RhoGAP, and Focal Adhesion Kinase Regulates Diverse Cellular Processes," *Chemical Reviews*, 101(8):2425-2440 (2001).
Hubbard et al., "Protein Tyrosine Kinase Structure and Function," *Annu. Rev. Biochem.*, 69:373-398 (2000).
Irby et al., "Role of Src Expression and Activation in Human Cancer," *Oncogene*, 19:5636-5642 (2000).
Johnson et al., "Protein Tyrosine Phosphatase 1B Inhibitors for Diabetes," *Nat. Rev. Drg. Discov.*, 1(9):696-709 (2002) (Abstract).
Kennedy, "Role of Protein Tyrosine Phosphatase-1B in Diabetes and Obesity," *Biomedicine & Pharmacotherapy*, 53(10):466-470 (1999).
Martin, "Timeline: The Hunting of the Src," *Nat. Rev. Mol. Cell Biol.*, 2:467-475 (2001).

Martin, et al., "Discovery of a human liver glycogen phosphorylase inhibitor that lowers blood glucose in vivo" *Proc. Natl. Acad. Sci. USA*, 95:1776-1781 (1998).

McCluskey et al., "Small Molecule Inhibitors of Serine/Theonine Protein Phosphatases,"*Mini-Reviews in Medicinal Chemistry*, 1(1):43-55 (2001) (Abstract).

Milkiewicz, "Design, Synthesis and Biological Testing of Non-ATP Competitive Inhibitors of the pp60$^{c\text{-}src}$ Protein Tyrosine Kinase," A dissertation submitted to the Faculty of the Graduate School of State University of New York at Buffalo in Partial Fulfillment of the Requirements for the Degree of Doctor of Philosophy, Department of Medicinal Chemistry (2001).

Miyazaki, et al., "Src Kinase Activity Is Essential for Osteoclast Function"*J. Biol. Chem.* 279:17660-17666 (2004).

Moller et al, "Protein Tyrosine Phosphatases (PTPs) as Drug Targets: Inhibitors of PTP-1B for the Treatment of Diabetes," *Current Opinion in Drug Discovery & Development*, 3(5):527-540 (2000) (Abstract).

Muller, "Peptidomimetic SH2 Domain Antagonists for Targeting Signal Transduction,"*Topics in Current Chemistry*, 211:17-59 (2001) (Abstract).

Parang, et al., "Recent advances in the discovery of Src kinase inhibitors"*Expert Opin. Ther. Patents* 15:1183-1207 (2005).

Park et al., "Metabolism of Fluorine-Containing Drugs,"*Annu. Rev. Pharmacol. Toxicol.*, 41:443-470 (2001).

Paul, et al., "Src deficiency or blockade of Src activity in mice provides cerebral protection following stroke" *Nat. Med.*, 7:222-227 (2001).

Ripka, "Chapter 21. Protein Tyrosine Phosphatase Inhibition,"Annual Reports in Medicinal Chemistry, 35:231-250 (2000) (Abstract).

Sedlacek, "Kinase Inhibitors in Cancer Therapy."*Drugs*, 59(3):435-476 (2000).

Sparks et al, "Identification and Characterization of Src SH3 Ligands from Phage-Displayed Random Peptide," *Journal of Biological Chemistry*, 269(39):23853-23856 (1994) (Abstract).

Sridhar et al., "Protein Kinases as Therapeutic Targets," *Pharmaceutical Research*, 17(11):1345-1353 (2000).

Stein, "SH2 and SH3 Domains. Unraveling Signaling Networks with Peptide Antagonists,"*Methods in Molecular Biology*, 88:187-195 (1998) (Abstract).

Susa et al., "Tyrosine Kinase Src Inhibitors: Potential Therapeutic Applications," *Drug News Perspect.*, 13(3):169-175 (2000).

Tegge et al., "Analysis of protein kinase substrate specificity by the use of peptide libraries on cellulose paper (SPOT-Method)", *Meth. Mol. Biol.*, 87:99-106 (1998).

Vu, "Recent Advances in the Design and Synthesis of SH2 Inhibitors of Src, Grb2 and ZAP-70," *Current Medicinal Chemistry*, 7(10):1081-1100 (2000) (Abstract).

Yu, et al., "Src, a molecular switch governing gain control of synaptic transmission mediated by*N*-methyl-D-aspartate receptors" *Proc. Natl. Acad. Sci* USA. 96:7697-7704 (1999).

Zhang, "Protein Tyrosine Phosphatases: Prospects for Therapeutics," *Current Opinion in Chemical Biology*, 5(4):416-423 (2001) (Abstract).

Wright, W.B. et al, Central Nervous System Depressants, IV, Nov. 1968, p. 1164-67.

Prasit, Accession No. 2002:695723, Document No. 137:232908, "Preparation of N-cyanomethyl amides as cathepsin cysteine protease inhibitors".

Strobel, Accession No. 2002:637636, Document No. 137:185515, "Preparation of acylated indanyl amines and their use as remedies in upregulation of endothelial nitric oxide synthase."

Takahashi, Accession No. 1999:271331, Document No. 130:311803, "Preparation of aminobutanoic acid derivatives as inhibitors of matrix metalloproteinases."

* cited by examiner

Binding interactions of src substrate Ac-Ile-Tyr-Gly-Glu-Phe-NH₂ in model src active site.

KINASE INHIBITORS

This patent application claims the benefit under 35 U.S.C. 120 and is a continuation of U.S. Ser. No. 09/482,585 filed Jan. 13, 2000, now U.S. Pat. No. 7,070,936, which claims the benefit under 35 U.S.C. 119(e) of U.S. Provisional Patent Application Ser. No. 60/115,643, filed Jan. 13, 1999. The entire contents of each of the above identified applications is hereby incorporated by reference.

BACKGROUND OF THE INVENTION

Protein kinases are a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation and proliferation. There are estimated to be about 2,000 distinct protein kinases in the human body (Hunter, 1987, 1994, Hanks & Hunter, 1995), and although each of these phosphorylate particular protein/peptide substrates, they all bind the same second substrate ATP in a highly conserved pocket.

Inhibitors of various known protein kinases could have a variety of therapeutic applications provided sufficient selectivity, and acceptable in vivo pharmacological properties, can be incorporated into such inhibitors (Levitzki, 1996a). Perhaps the most promising potential therapeutic use for protein kinase inhibitors is as anti-cancer agents. This potential application for protein tyrosine kinase ("PTK") inhibitors has been highlighted in many recent reviews (e.g. Lawrence & Hiu, 1998, Kolibaba & Druker, 1997, Showalter & Kraker, 1997, Patrick & Heimbrook, 1996, Groundwater et al., 1996, Levitzki, 1995). The foundation for this application is based partly upon the fact that about 50% of the known oncogene products are PTKs and their kinase activity has been shown to lead to cell transformation (Yamamoto, 1993).

The PTKs can be classified into two categories (Courtneidge, 1994), the membrane receptor PTKs (e.g. growth factor receptor PTKs) and the non-receptor PTKs (e.g. the src family of proto-oncogene products). There are at least 9 members of the src family of non-receptor PTKs with pp60$^{c\text{-}}$$_{src}$ (hereafter referred to simply as "src") being the prototype PTK of the family wherein the approximately 300 amino acid catalytic domains are highly conserved (Rudd et al., 1993, Courtneidge, 1994). The hyperactivation of src has been reported in a number of human cancers, including those of the colon (Mao et al., 1997, Talamonti et al., 1993), breast (Luttrell et al., 1994), lung (Mazurenko et a, 1992), bladder (Fanning et al., 1992) and skin (Barnekow et al., 1987) as well as in gastric cancer (Takeshima et al., 1991), hairy cell leukemia (Lynch et al., 1993) and neuroblastoma (Bjelfman et al., 1990). Overstimulated cell proliferation signals from transmembrane receptors (e.g. EGFR and p185HER2/Neu) to the cell interior also appears to pass through src (Mao et al., 1997, Parsons & Parsons, 1997, Bjorge et al., 1996, Taylor & Shalloway, 1996). Consequently, it has recently been proposed that src is a universal target for cancer therapy (Levitzki, 1996) because its hyperactivation (without mutation) is involved in tumor initiation, progression, and metastasis for many important human tumor types.

In view of the large and growing potential for inhibitors of various protein kinases, a variety of approaches to obtaining useful inhibitors is needed. The status of the discovery of PTK inhibitors (Lawrence & Niu, 1988, Showalter & Kraker, 1997, Patrick & Heimbrook, 1996, Groundwater et al., 1996, Budde et al., 1995, Levitzki & Gazit, 1995) has been extensively reviewed. Random screening efforts have been successful in identifying non-peptide protein kinase inhibitors but the vast majority of these inhibitors bind in the highly conserved ATP binding site. A notable recent example of such non-peptide, ATP-competitive, inhibitors are the 4-anilinoquinazolines and analogs, which were shown to be effective against the epidermal growth factor receptor PTK (EGFRTK) (e.g. Rewcastle et al., 1996). Although this class of inhibitors was reported to be selective for the EGFR PTK vs. six other PTKs (including src, Fry et al., 1994) it is unknown what their effect is on most of the remaining 2,000 protein kinases that all bind ATP as well as a large number of other ATP, ADP, GTP, GDP, etc. utilizing proteins in the body. Therefore, potential side effects from PTK inhibitor drugs that mimic ATP, which might only be discovered after expensive animal toxicity studies or human clinical trials, are still a serious concern. Also, although this class of compounds was a nice discovery and is undergoing further exploration, these compounds do not provide a rational and general solution to obtaining non-peptide inhibitors for any desired PTK, e.g. in this case src. The risk of insufficient specificity in vivo with ATP-competitive PTK inhibitors has also been noted by others, along with the inherent three order of magnitude reduction in potency these inhibitors display when competing with the mM levels of intracellular ATP rather than the μM levels used in the isolated enzyme assays (e.g. see Lawrence & Niu, 1998, Hanke et al., 1996, Kelloff et al., 1996).

An older, and more extensively studied, class of non-peptide PTK inhibitors is erbstatin and the related tyrphostins (see reviews). This class of inhibitors is active against the receptor PTKs and their mode of inhibition is complex but does not appear to involve binding in the peptide substrate specificity site regions of the active site (Hsu et al., 1992, Posner et al., 1994). Furthermore, this class of inhibitorsis inactive against the isolated PTK when the unnatural assay metal $Mn^{2+}$ is replaced with the natural $Mg^{2+}$ (Hsu et al., 1992), is chemically unstable (Budde et al., 1995, Ramdas et al., 1995 & 1994), and is known to be cytotoxic to normal and neoplastic cells by crosslinking proteins (Stanwell et al., 1995 & 1996) as well as to inhibit cell growth by disrupting mitochondria rather than PTK inhibition (Burger et al., 1995).

An important contribution to the protein kinase field has been the x-ray structural work with the serine kinase cAMP-dependent protein kinase ("PKA") bound to the 20-residue peptide derived from the heat stable inhibitor protein, PKI(5-24), and $Mg_2ATP$ (Taylor et al., 1993). This structural work is particularly valuable because PKA is considered to be a prototype for the entire family of protein kinases since protein kinases have evolved from a single ancestral protein kinase. Sequence alignments of PKA with other serine and tyrosine kinases have identified a conserved catalytic core of about 260 residues and 11 highly conserved residues within this core (Taylor et al., 1993). Two highly conserved residues of particular note for the work proposed herein are the general base Asp-166, which is proposed to interact with the substrate OH and the positively charged residue, Lys-168 for serine kinases and an Arg for tyrosine kinases (Knighton et al., 1993), which is proposed to interact with the γ-phosphate of ATP to help catalyze transfer of this phosphate. Two additional important PKA crystal structures have been reported (Madhusudan et al., 1994), one for the ternary PKA:ADP: PKI(5-24) complex wherein the PKI Ala 21 has been replaced with Ser (thereby becoming a substrate), and one for the binary PKA:PKI(5-24) complex wherein the PKI Ala 21 has been replaced with phosphoserine (an end product inhibitor). The ternary complex shows the serine OH donating a H-bond to Asp-166 and accepting a H-bond from the side chain of Lys 168. The binary complex shows the phosphate group of phosphoserine forming a salt bridge with the Lys-168 side chain and within H-bonding distance of the Asp-166 carboxyl group. These structures support the earlier proposed roles for Asp-166 and Lys-168 in the catalytic mechanism.

The x-ray structures of PKA show that the enzyme consists of two lobes where the smaller lobe binds ATP and the larger lobe binds the peptide substrate. Catalysis occurs at the cleft between the lobes. The crystallographic and solution structural studies with PKA have indicated that the enzyme undergoes major conformational changes from an "open" form to the "closed" catalytically active form as it binds the substrates (Cox et al., 1994). These conformational changes are presumed to involve the closing of the cleft between the two lobes as the substrates bind and bring the γ-phosphate of ATP and the Ser OH in closer proximity for direct transfer of the phosphate.

However, the inhibitors of protein kinases still lack the specificity and potency desired for therapeutic use. Due to the key roles played by protein kinases in a number of different diseases, including cancer, psoriasis, atherosclerosis, and their role in regulating immune system activity, inhibitors of specific protein kinases are needed. The present invention provides a novel approach for designing protein kinase inhibitors, which are more potent as well as being more specific for the targeted pathways.

SUMMARY OF THE INVENTION

The present invention provides a method for identifying inhibitors of protein kinases. A first module having a one or more functional groups for binding to catalytic residues of the protein kinase is combined with a second module which provides a non-peptide scaffold. Combinations of the first and second modules which inhibit protein kinase activity are selected.

The present invention also provides a method of inhibiting a protein kinase. The protein kinase is contacted by a compound comprising a first module having a functionality for binding to catalytic residues of the protein kinase and a second module which provides a non-peptide scaffold. The combination of the first and second modules inhibits the protein kinase activity.

In a further embodiment, the invention provides a non-peptide protein tyrosine kinase inhibitor having the formula I:

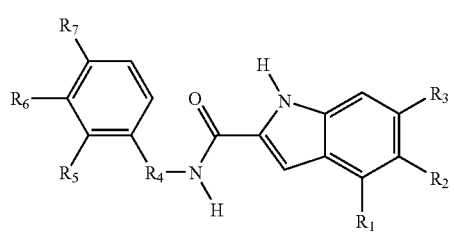

(I)

wherein $R_1$ is H or OH, $R_2$ is H or OH, $R_3$ is OH or H, and $R_4$ is $CH_2$, $CH(CH_3)$(R-configuration), or $CH(CH_3)$(S-configuration), $R_5$ is $OCH_3$, H, or OH, $R_6$ is $OCH_3$, F, H, or OH, and $R_7$ is $OCH_3$, H, OH, $CO_2H$, $CO_2CH_3$, $CH_2CO_2H$, or $CH_2CO_2CH_3$.

The present invention also provides a non-peptide protein tyrosine kinase inhibitor having the formula II:

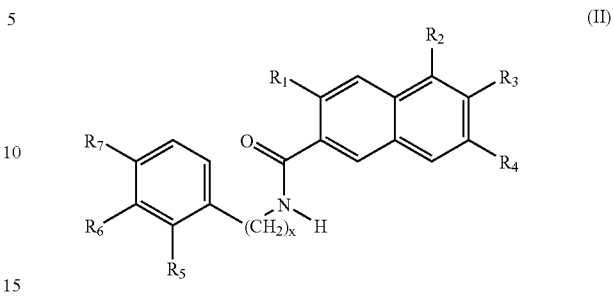

(II)

wherein $R_1$ is OH or H, $R_2$ is OH or H, $R_3$ is OH or H, $R_4$ is OH or H, $R_5$ is OH, OMe, or H, $R_6$ is OH, $OCH_3$, or H, $R_7$ is OH, $OCH_3$, or H, and X is 0 or 1.

In yet another embodiment, the present invention provides a method of treating a condition, responsive to a protein kinase inhibitor, in a patient. A protein kinase inhibitor is administered to a patient. The protein kinase inhibitor has a first module having a functionality for binding to catalytic residues of the protein kinase and a second module which provides a non-peptide scaffold. The combination of the first and second modules inhibits protein kinase activity in the patient.

DETAILED DESCRIPTION OF THE INVENTION

Figure 1:
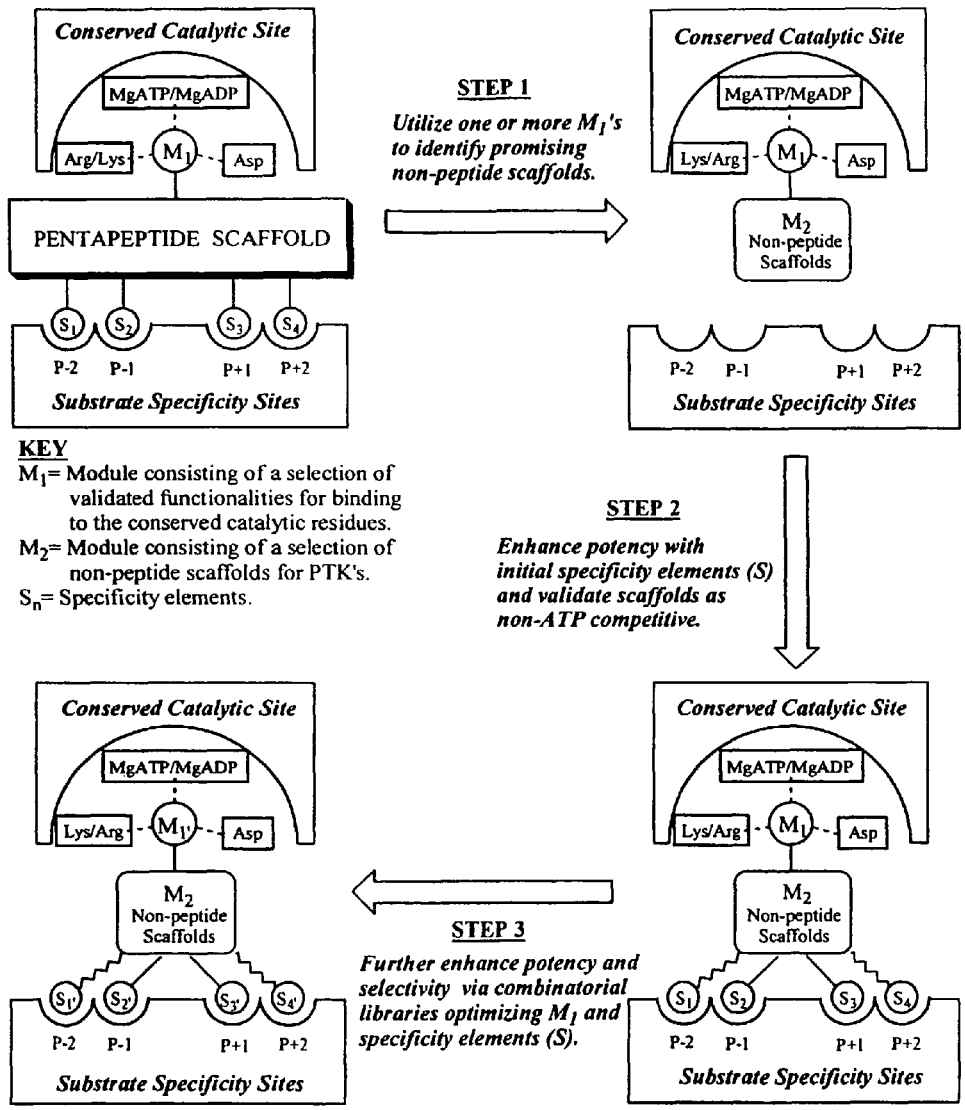
FIG. 1 depicts the modular strategy for developing non-peptide protein kinase inhibitors. Step 1 utilizes one or more first modules ("$M_1$" modules) to identify promising non-peptide scaffolds. Step 2 enhances the potency by adding specificity elements. During this step the scaffolds are validated. Whether the inhibitor is non-ATP competitive can also be determined. In step 3, the potency and selectivity are further enhanced using combinatorial libraries to optimize $M_1$ and specificity elements.

The present invention provides a method for identifying inhibitors of protein kinases. The general modular strategy for the development of non-peptide PTK inhibitors is outlined in FIG. 1. Basically, a first module having a one or more functional groups for binding to catalytic residues of the protein kinase is combined with a second module which provides a non-peptide scaffold. Combinations of the first and second modules which inhibit protein kinase activity are then selected. Step 1 uses scaffolds generated from protein kinase inhibitor information i.e. pentapeptide scaffolds which bind in the substrate specificity sites of PKA or src and position various rationally designed functional groups (i.e. module "$M_1$" or "first module") to interact with the conserved catalytic residues, MgATP or MgADP. A selection of preferred functional groups have been identified in this fashion to serve as the initial $M_1$ module for Step 1. These $M_1$ functional groups have been utilized to identify promising non-peptide scaffolds for src inhibitors in Step 1. It was anticipated that these initial non-peptide scaffolds, with only an $M_1$ appendage, would have a low binding affinity and be relatively non-selective among the PTKs. A lack of selectivity at the level of Step 1 is viewed as an advantage for the development of a general strategy which can be reapplied to develop inhibitors for other PTKs. Therefore the non-peptide scaffolds identified in Step 1 can be recycled for the development of additional inhibitors against other PTKs by re-screening and carrying the better inhibitors through Steps 2 and 3, against other PTK targets. The potency of these initial non-peptide scaffolds identified in Step 1 may be increased by the attachment of one or two initial specificity elements ($S_n$) to allow for the validation of the scaffold as non-ATP competitive and amenable to further potency enhancements using combinatorial chemistry in a rationally guided fashion. Promising src non-peptide $M_2$ (second module) scaffolds identified in Step 1 have undergone Step 2 and displayed a one to two order-of-magnitude increase in potency against src as well as non-competitive binding relative to ATP.

Validation of the scaffolds at the level of Step 2 before undertaking the resource intensive combinatorial library synthesis and testing of Step 3 is important for three reasons: 1) to develop the chemistry for appending the specificity element ($S_n$) side chains; 2) to determine that these inhibitors are not ATP-competitive; and 3) to determine that the potency is a result of the side chain $S_n$ properties and attachment points as would be expected based upon the working model for the src:inhibitor complex (this provides some confidence that rationally guided choices can be made for the ranges of individual selectivity elements $S_n$ to include in the focused libraries of Step 3).

It is in Step 3 that high potency and specificity for a particular PTK is anticipated because numerous combinations of $M_1$ functional groups (and close analogs $M_1$ modules) with selectivity elements ($S_n$) will be evaluated experimentally via combinatorial chemistry and high-throughput screening. Potency and selectivity may be further increased if necessary by appending additional specificity elements (see optional selectivity elements ($S_n$) in FIG. 1). One of the selected src inhibitor scaffolds from Step 2 has already been attached to a solid phase resin and is currently being developed into a combinatorial library following Step 3.

In each of the Steps 1-3, molecular modeling studies with the IRTK:peptide:AMP-PNP crystal structure, the model of the src:peptide complex and the models for the src complex with the individual families of inhibitors based upon a particular scaffold will be used as qualitative guides. These modeling studies have been remarkably helpful thus far in guiding the inhibitor design efforts as detailed later. Combining structure-based design and combinatorial chemistry technologies in this fashion provides a synergy where the major individual deficiencies of these technologies used in isolation are addressed by the strengths of the other. The major deficiency of structure-based design is the difficulty in quantitatively predicting ligand binding affinities, which is particularly challenging due to the complex effects of solvation and entropy (Ajay & Murcko, 1995). The major strength of structure-based design is its capability to predict what types of molecules are likely to be good ligands. Structure-based design can determine the rough boundaries (proteins have some flexibility which need to be taken into account) for molecular size and shape as well as indicate where hydrophobic, hydrogen-bonding and ionic interactions are likely to occur. On the other hand, the major deficiency of combinatorial chemistry is that "molecular space" for drug-sized molecules (i.e. MW approximately 500 or less) is so large that one could not hope to sample all of this molecular space with a high density of coverage in a reasonable sized combinatorial library. A recent estimate (Bohacek et al., 1996) of the number of possible compounds containing up to 30 atoms chosen only from carbon, nitrogen, oxygen and sulfur (in addition to hydrogen) is $10^{60}$ compounds. This includes compounds in the molecular weight range of typical drug molecules and still does not include additional diversity provided by other atoms, e.g. halogens. Consequently, additional constraints need to be used to identify regions of molecular space where particular drug candidates are likely to be located. Structure-based design can drastically reduce the volume of molecular space that needs to be explored by identifying the types of molecules which have a higher probability of being good ligands. The inability to quantitatively predict which of these "focused" combinatorial library members will in fact be the tightest binding ligands (i.e. the quantitation problem) is then resolved by employing an efficient combinatorial synthesis and high-throughput testing of the library.

In the earlier efforts to design peptide based serine and tyrosine kinase inhibitors, PKA was used as a convenient qualitative model for designing the protein kinase inhibitor module $M_1$ for interaction with the conserved catalytic residues. There is much more structural and kinetic information available for PKA than any other protein kinase.

Figure 2:
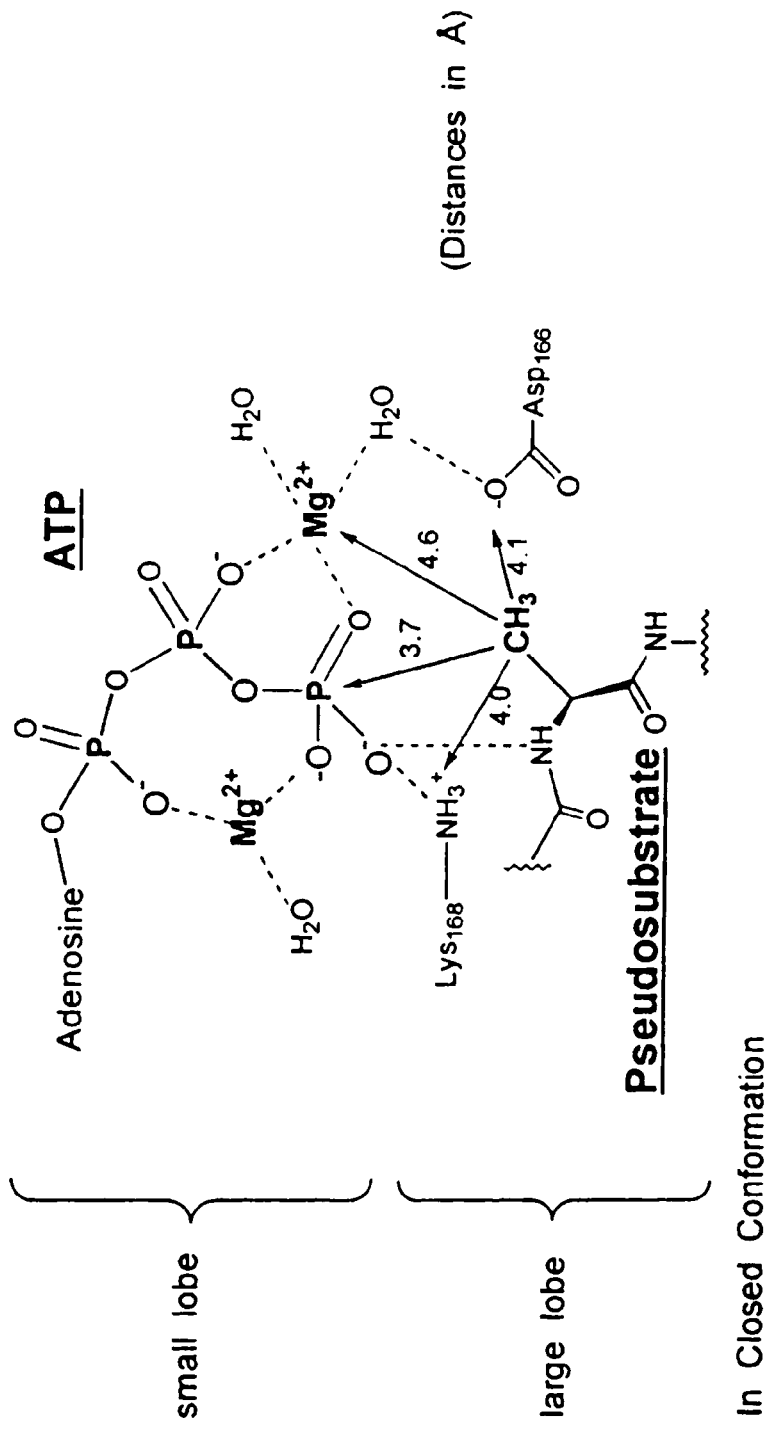
FIG. 2 provides a depiction of the x-ray structure of (PKA): $Mg_2ATP$:pseudosubstrate inhibitor.

The crystal structure of PKA complexed with $Mg_2ATP$ and a pseudosubstrate (i.e. OH replaced with H) peptide inhibitor (PKI 5-24 amide) has been solved (Zheng et al., 1993) and the active site interactions near the P 0 Ala of this inhibitor are shown in FIG. 2.

This crystal structure shows $Mg_2ATP$ bound to the small lobe of PKA and a 20-residue pseudosubstrate peptide inhibitor bound to the large lobe with the overall conformation of the enzyme in the closed (i.e. the two lobes are touching) and activated state. The distances between the P 0 Ala side chain carbon and the nearby heavy atoms in the complex are shown in $A^O$ in FIG. 2. These distances show that the Ala side chain is within van der Waals contact distance of the surrounding atoms and indicates that there is little space for appending bulky $M_1$ functional groups to the Ala side chain. However, PKA is a flexible enzyme with open, closed and intermediate conformations (Cox et al., 1994) and the more open conformations would result in a retraction back of the ATP γ-phosphate from the inhibitor Ala thereby creating a binding cavity for appended $M_1$ functional groups. Furthermore, PKA binds MgADP with the same affinity as MgATP (Whitehouse et al., 1983) and the ratio of ATP/ADP in cells is typically 10/1 (Alberts, et al. 1994). Therefore, at equilibrium, approximately 10% of the cellular protein kinase is in the MgADP bound state and this form of the enzyme can also be targeted with an inhibitor to drain all of the enzyme from the catalytic cycle into a PKA:MgADP:inhibitor inactive complex.

Since the PKA catalytic residues Asp-166 and Lys-168 are completely conserved in all serine kinases, and the tyrosine kinases only differ by the substitution of Arg for Lys-168 (Taylor et al., 1993), this region of the active site was chosen, along with the adjoining MgATP or MgADP, to target a selection of inhibitor functional groups which could serve as $M_1$ and be broadly useful for developing inhibitors for the entire protein kinase family. By targeting $M_1$ to the region of the active site adjacent to the nucleotide, an orientation point is provided for the non-peptide inhibitors which can extend into the peptide binding specificity sites without always competing with ATP/ADP binding.

A selection of functional groups which could be utilized as $M_1$ was identified first because, although this region of the active site is very highly conserved, it was expected that each particular protein kinase will still display some differing preferences across this selection due to small variations in the active site conformations and adjoining residues. Furthermore, the rank order preference among this selection of $M_1$ modules may change somewhat as the $M_1$ module is appended to different non-peptide scaffolds. This expectation is based upon the potential for each non-peptide scaffold to bind in somewhat different orientations with each individual protein kinase and with each particular set of selectivity element ($S_n$) side chains. Pentapeptide scaffolds were chosen for the initial screening of functional groups for $M_1$ because the binding orientation of these larger peptide scaffolds is likely to be very consistent and predictable (i.e. closely resembling that observed by x-ray) throughout the series and could be more confidently assumed to position each tested $M_1$ functionality adjacent to the conserved catalytic residues as intended. Consequently, the goal of this earlier peptide-based work was to identify a collection of $M_1$ functional groups which can be used, not only for the initial screening of non-scaffolds (Step 1), but also as an initial set of $M_1$ side chains which can be further expanded via close analogs and thereby optimized simultaneously with the other side chains in the final non-peptide combinatorial libraries (Step 3).

Figure 3:
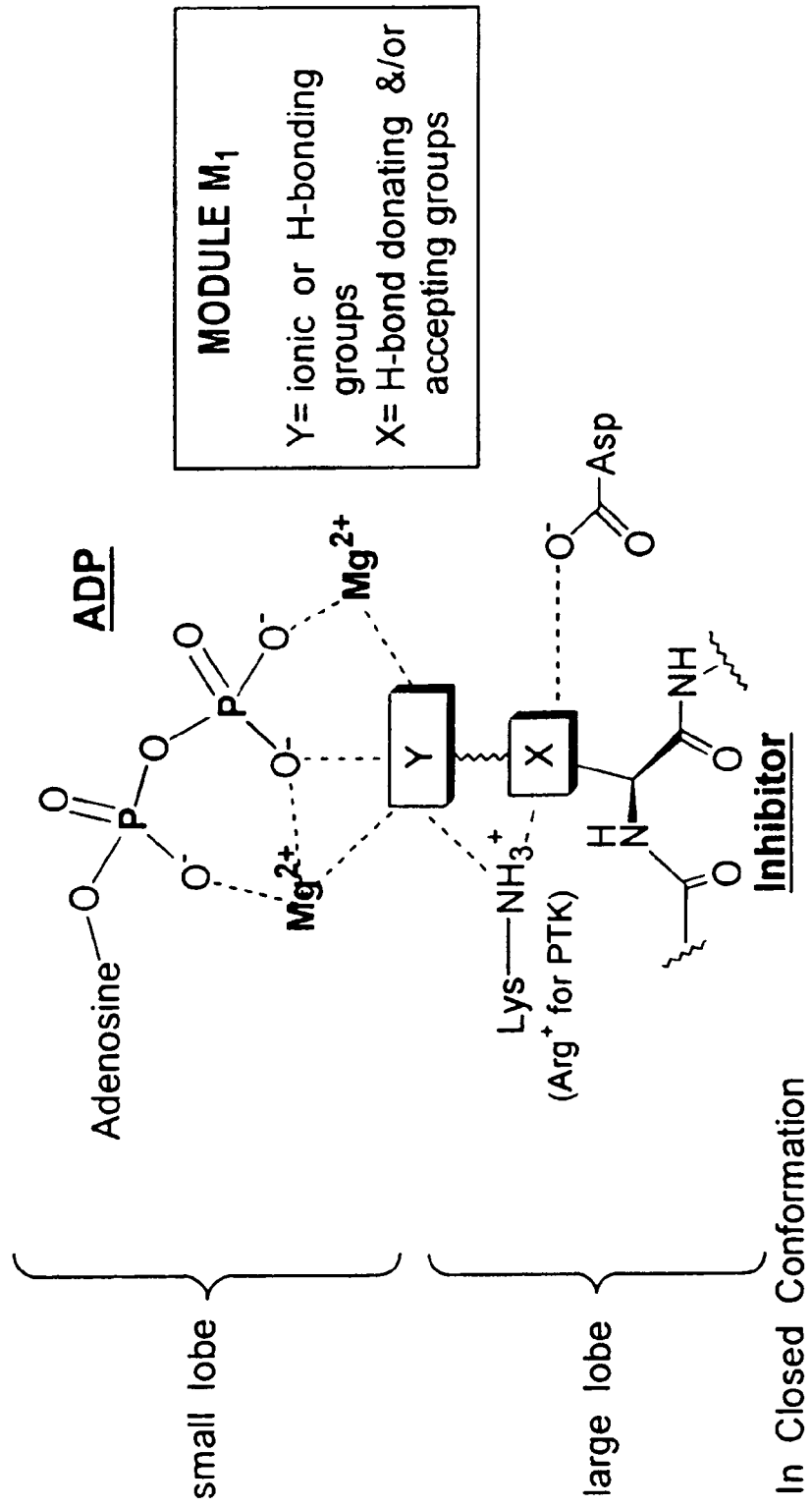
FIG. 3 provides a general module $M_1$ design features for binding to the conserved protein kinase catalytic region.

In order to model the candidate $M_1$ functional groups in this conserved catalytic region of the PKA active site, they were built onto the P 0 Ala position in the PKA ternary structure using the SYBYL molecular modeling package (Tripos) on a Silicone Graphics workstation as indicated in FIG. 3.

A crystal structure of PKA with MgATP and an inhibitor bound in a more "open" conformation was not available, so initial modeling studies were carried out on the MgADP bound form of PKA derived from the ternary complex illustrated in FIG. 2 by simply deleting the ATP γ-phosphate. Initial modeling studies were used to provide qualitative guidance for identifying interesting potential $M_1$ functional groups for the protein kinase family before synthesis and testing. The most advanced computational algorithms for quantitatively predicting the free energy of binding, such as Free Energy Perturbation methods, are computationally intensive methods which are not practical at this point in time for routine use by the non-specialist. Even the most advanced methods can be inaccurate due to difficulties in sampling, inadequacies in the molecular mechanics force fields/parameters, and an incomplete understanding of electrostatics in water (Ajay & Murcko, 1995). Less rigorous (and easier to use) computational methods tend to be unreliable in making quantitative predictions of binding affinities, especially when dealing with multiple polar and ionic interactions such as those involved in $M_1$ binding.

In order to allow molecular mechanics calculations to be done with the Silicone Graphics workstation in a reasonable amount of time, two layers of residues were carved out from the PKA ternary structure which are surrounding the PKA active site, along with the peptide inhibitor and $Mg_2ADP$. The $M_1$ functional groups were then appended to the P 0 Ala side chain and the entire PKA active site:$Mg_2ADP$:modified peptide inhibitor complex was then subjected to 300 iterations of molecular mechanics minimization using the Tripos force field with a distance dependent dielectric constant after assigning appropriate formal charges and calculating Gasteiger Marsili point charges using SYBYL. Setting the maximum number of iterations at 300 was sufficient to remove any serious strain in the complexes and yet not allow the overall structure to "drift" significantly from the starting x-ray structure if convergence is not reached. These minimized complexes were then visually evaluated to determine if the appended individual $M_1$ functional groups were able to engage in favorable interactions with the conserved catalytic residues and/or $Mg_2ADP$. This visual evaluation involved, among other standard interaction evaluations, measuring atom-atom distances to determine if hydrogen bonds and ionic interactions were being favorably formed.

Favorable intermolecular interactions between an individual $M_1$ functionality and the conserved catalytic residues or $Mg_2ADP$ does not necessarily mean an enhanced binding affinity will be observed for the new inhibitor. Unfavorable desolvation of both the polar $M_1$ functionality and the polar PKA active site residues (as well as complex entropy effects) are not included in this analysis and may reduce the net binding affinity to the point that the modified inhibitor may even be less potent that the corresponding P 0 Ala inhibitor, even though the appended $M_1$ functionality is interacting with the conserved catalytic residues and/or MgADP (or MgATP)

as intended. Even in cases where this desolvation penalty results in no net increase in binding affinity, these $M_1$ functional groups are still useful as an orienting groups for correctly positioning the non-peptide inhibitor analogs in the protein kinase active site. Positioning these polar functional groups elsewhere within the active site (assuming the groups are tethered so as not to be able to extend into bulk solvent while the scaffold is favorably bound in the active site) is likely to result in a reduced binding affinity because the groups were specifically designed and selected based upon their demonstrated ability (while appropriately tethered to pentapeptide scaffolds) to be accepted adjacent to the conserved catalytic residues and MgADP/MgATP. If a particular $M_1$ functionality does not correctly position a non-peptide scaffold in Step 1 then attempts to improve the potency by rationally appending initial specificity elements in Step 2 would likely fail.

None of the literature protein kinase assay procedures contain added ADP. A typical PKA literature assay procedure (Glass et al., 1989) was modified by adding 10% as much ADP as the ATP concentration used to reflect the natural 1/10 ratio in the cell. This protein kinase assay is hereinafter referred to as the "Literature Mimetic" assay. It has been used for PKA as well as for the cyclic AMP dependent kinase src. An examination of the literature, and commercially available protein kinase assays, showed that there is poor consistency from lab to lab and company to company and that all of these assays use physical chemical conditions which differ considerably from those known to exist inside cells. Since inhibition of intracellular protein kinases is the ultimate goal for drug discovery, new protein kinase assays have been developed which come much closer to mimicking the overall cytosolic physical chemical conditions known to exist inside cells. The development of these "Cellular Mimetic" protein kinase assays, is described herein, along with a novel method for determining which form of a protein kinase a given inhibitor binds to best (the STAIRe method). Data was collected correlating the activity of the new non-peptide src inhibitors in the Cellular Mimetic assay with that obtained in the LA25 src transformed cell line (see below).

When these two assay conditions were applied to some of the pentapeptide-based PKA inhibitors, which were designed as illustrated in FIG. 3, the results shown in Table I were obtained. The same assay conditions were also applied to the analogously designed pentapeptide-based src inhibitors and the results are shown in Table II.

The standard pentapeptide sequence chosen for the majority of PKA inhibitors in Table I was derived from the pseudosubstrate sequence of the peptide inhibitor which was bound to PKA, when the crystal structure illustrated in FIG. 2 was solved. The standard pentapeptide sequence used for src in Table II, Ac-Ile-Xaa-Gly-Glu-Phe-NH$_2$ (SEQ. ID. No. 2), was described in Nair, Kim et al., 1995. Some of the chemistry used to prepare the PKA inhibitors is described in Nair, Lee & Hangauer 1995. The synthetic methodology used to develop a number of the src inhibitors is described in Lai et al., 1998.

The collective results in Tables I and II show that both the serine kinase PKA and the PTK src can accommodate a variety of large polar $M_1$ functional groups at the P 0 phosphorylation position. Furthermore, using the STAIRe methodology (see Choi et al. 1996), the sulfamic acid inhibitor 8, and related inhibitors, were shown to actually bind best when MgATP (not MgADP or no nucleotide) is also bound. This was a somewhat surprising result since these inhibitors are analogs of the "end product inhibitors" 1 and 12 which must bind simultaneously with MgADP, following phosphate transfer in the generally accepted reaction mechanism for protein kinases.

These results also demonstrate that both PKA and src can show a large difference in binding affinity for structurally very similar inhibitors. For example, the sulfamic acid PKA inhibitor 8 (Table I) has a $K_i$ of 0.16 µM under Literature Mimetic assay conditions (L) whereas the isosteric sulfonamide 7 is 1,875 times less potent ($K_i$=300 µM). The sulfamic acid inhibitor 8 is also isosteric with the end product phosphate inhibitor 1, yet it binds much more tightly under both Literature Mimetic assay conditions (31 times) and Cellular Mimetic (C) assay conditions (108 times). The beneficial effect of an oxygen atom positioned analogously to the oxygen in the substrate Ser is illustrated by comparison of phosphonate 2 to phosphate 1 and also ether 6 to phosphate 1. The oxygen atom can also be positioned as a serine-like OH side chain and enhance binding (compare 2 to 3A and 4A) wherein the closer serine mimic 4A is the more active. The difference in activity of the diasteromeric inhibitors 3A or B and 4A or B suggests that a specific interaction with the active site catalytic residue Asp-166 may in fact be occurring as intended in the $M_1$ design (FIG. 3).

TABLE I

INITIAL $M_1$ SCREENING RESULTS WHILE APPENDED TO THE PKA PENTAPEPTDE SCAFFOLD

Ac-Arg-Arg-Gly-NH—[$M_1$]—Ile-NH$_2$ (with C=O)

$K_i$ (µM), (Conditions*)

1 $M_1$ = O=P(OH)(OH)—O— (End Product Inhibitor)
 5 (L)
 542 (L) ⎫ 108 X

2 $M_1$ = O=P(OH)(OH)—
 76 (L)
 NT (C)

3 $M_1$ = O=P(OH)(OH)— with (R or S) CH(OH)
 18 (L)-Diastereomer A
 72 (L)-Diastereomer B
 NT (C)

4 $M_1$ = HO—P(=O)(OH)—O— with (R or S) CH(OH)
 4 (L)-Diastereomer A
 20 (L)-Diastereomer B ⎫ 43 X
 171 (C)-Diastereomer A
 1510 (C)-Diastereomer B

TABLE I-continued

INITIAL $M_1$ SCREENING RESULTS WHILE APPENDED TO THE PKA PENTAPEPTDE SCAFFOLD

Ac-Arg-Arg-Gly-NH—*CH(M_1)*—C(O)—Ile-NH$_2$ $K_i$ (µM), (Conditions*)

| $M_1$ structure | Values |
|---|---|
| $M_1 =$ HO$_2$C—CH(X)—O—CH$_2$— ; 5 X = H | 28 (L) / 780 (C) ) 29 X |
| 6 X = CO$_2$H | 6 (L) / 450 (C) ) 75 X |
| 7 $M_1 =$ —CH$_2$—CH$_2$—S(=O)$_2$—NH$_2$ | 300 (L) / 2400 (C) ) 8 X |
| 8 $M_1 =$ —CH$_2$—NH—S(=O)$_2$—OH | 0.16 (L) / 5 (C) ) 31 X |
| 9 $M_1 =$ —CH$_2$—S(=O)(=O)—NH$_2$ | 250 (L) / 2100 (C) ) 8 X |
| 10 $M_1 =$ —CH$_2$—NH$_2$ | 38 (L) / 115 (C) ) 3 X |
| 11 $M_1 =$ —CH$_2$—NH—CH(CO$_2$H)—CH$_2$—CO$_2$H | 45 (L) / NT (C) |

- - - - = Attachment Point

*L = Literature Mimetic
C = Cellular Mimetic

The structure identified in Table I as Ac-Arg-Arg-Gly-Ala bonded to $M_1$-Ile-NH$_2$ is SEQ. ID. No. 3.

The src inhibition results (Table II) show that the end product inhibitor 12 drops in activity upon going from Literature Mimetic assay conditions to the higher ionic strength Cellular Mimetic assay conditions analogous to the PKA end product inhibitor 1. However, whereas all of the PKA inhibitors with polar $M_1$ functional groups were less active under Cellular Mimetic assay conditions than three of the src inhibitors 14, 15, and 17 which held their activity under these higher ionic strength assay conditions. Also, the hydroxyphosphonate src inhibitor 13 (a mixture of the R and S diastereomers) is analogous to the PKA inhibitor 3A and both are roughly in the same activity range as their corresponding end product inhibitors, 12 and 1 respectively, under Literature Mimetic assay conditions. Shortening the side chain length in the phosphonate src inhibitor 13 by one carbon atom (and necessarily removing the attached OH at the same time) to give 14 improved the activity (analogous to the PKA inhibitor comparison 3 to 4) and, more importantly, resulted in equivalent activity under Cellular Mimetic assay conditions. The src results with 16-19 (particularly 17, see later for an analogous α-tricarbonyl acid $M_1$ analog appended to non-peptide src inhibitors) also suggests that similar amides may be useful $M_1$ functional groups to explore with non-peptide src inhibitors.

Non-peptide src inhibitors are preferred to peptide scaffold based compounds, partly because some of these inhibitors have a dual effect on src. For example, phosphonate inhibitor 14 not only inhibits src by competitively binding in the active site but it also activates src by binding to the SH2 site thereby releasing the intramolecular autoinhibition mechanism (Xu et al., 1997). This opposing effect gives an unusual IC$_{50}$ curve for 14 wherein at low inhibitor concentrations src is stimulated (to a maximum of 70%) in a smooth dose-response fashion (due to initial tighter SH2 binding) followed by a typical IC$_{50}$ inhibition curve at higher inhibition or concentration (due to lower affinity blockade of the active site). This opposing activation effect of the pentapeptide inhibitors makes the inhibitors appear to be less potent active site inhibitors than they in fact are, and makes it difficult to accurately rank $M_1$ groups while appended to this pentapeptide scaffold. However, the better $M_1$ groups identified with the src pentapeptide scaffold must still be accommodated in the catalytic region of the active site and hence are useful orienting groups for the ongoing non-peptide src inhibitor studies as intended. Since PKA does not have an SH2 domain, this complication is not a factor in interpreting the PKA pentapeptide inhibitor $M_1$ testing data.

TABLE II

INITIAL $M_1$ SCREENING RESULTS WHILE APPENDED TO THE SRC PENTAPEPTIDE SCAFFOLD

Ac-Ile-NH—CH(CH$_2$-C$_6$H$_4$-$M_1$)—C(O)—Gly-Phe-NH$_2$

% Inhibition of 2 mM RR-src phosphorylation by src Assay Conditions

| Inhibitor (1 mM) | Literature Mimetic | Cellular Mimetic |
|---|---|---|
| 12 $M_1 =$ —P(=O)(OH)$_2$ | 36 | 0 |

TABLE II-continued

INITIAL $M_1$ SCREENING RESULTS WHILE
APPENDED TO THE SRC PENTAPEPTIDE SCAFFOLD

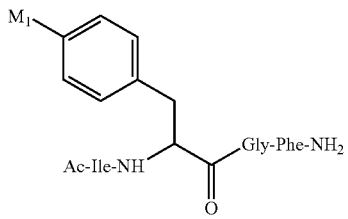

| Inhibitor (1 mM) | % Inhibition of 2 mM RR-src phosphorylation by src Assay Conditions | |
|---|---|---|
| | Literature Mimetic | Cellular Mimetic |
| 13 $M_1$ = 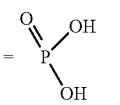 | 51 | 0 |
| 14 $M_1$ = 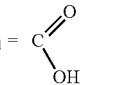 | 83 | 88 |
| 15 $M_1$ = 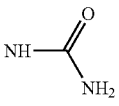 | 68 | 59 |
| 16 $M_1$ = 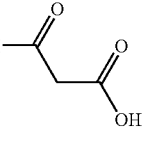 | 60 | 8 |
| 17 $M_1$ = 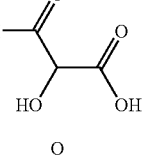 | 20 | 28 |
| 18 $M_1$ = 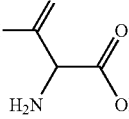 | 64 | 5 |
| 19 $M_1$ = | 24 | 0 |

The structure identified in Table II as Ac-Ile-Tyr bonded to $M_1$-Gly-Glu-Phe-NH$_2$ is SEQ. ID. No. 2.

The results in Tables I and II also show how much effect the assay conditions can have on both inhibitor potencies and the rank order of activity. For example, as shown in Table I, switching from the Literature Mimetic (L) assay conditions to the Cellular Mimetic (C) assay conditions can change the potency from as little as 3-fold (inhibitor 10) to as much as 108-fold (inhibitor 1). Also, whereas inhibitor 10 is less potent than 1 under Literature Mimetic conditions, it is more potent under Cellular Mimetic conditions. The src inhibitor data presented in Table II shows that many of the inhibitors lose their potency upon going from Literature Mimetic assay conditions to Cellular Mimetic assay conditions. The rank order of potency against src is also sensitive to the assay conditions. Whereas inhibitor 18 is more potent than inhibitor 17 under Literature Mimetic conditions, the opposite is true under Cellular Mimetic conditions. Since activity within cells is the goal, the Cellular Mimetic src assay was selected as the standard assay for testing potential non-peptide src inhibitors. Activity within the Cellular Mimetic assay is a necessary, but not sufficient, condition for activity within cells. As will be described later, the Cellular Mimetic src assay will be followed up with cell culture assays wherein cell penetration, metabolism, and binding to other cellular components are also factors in the measured potency.

The next class of $M_1$ functionality which was explored was the boronic acid group. This functional group is an intriguing candidate for $M_1$ for a number of reasons: 1) It can exist in a non-ionic state so that it should not prevent passive absorption of non-peptide inhibitors across cell membranes. 2) The planar, trigonal, boron acids might form reversible tetrahedral covalent borate complexes (a well known property of boronic acids, see Loomis & Durst, 1992) through their vacant 2p orbitals with anions present in the protein kinase active site such as the catalytic Asp carboxyl group or the ATP/ADP terminal phosphate oxygen atoms. This ability to form borate complexes with active site nucleophiles has been extensively utilized to develop slow binding inhibitors of serine proteases (e.g. see Kettner & Shenvi, 1984), where the nucleophilic serine OH forms a covalent bond with the vacant 2p orbital in the boronic acid resulting in a tetrahedral borate complex (e.g. see Skordalakes et al., 1997). Also, an intramolecular complex of a boronic acid with a urea $NH_2$ was used to prepare transition state analogs inhibitors of dihydroorotase (Kinder et al., 1990). 3) Boronic acids act as Lewis acids and are converted to tetrahedral hydrates in water by forming borate complexes with water or hydroxide ions. Therefore, it is also possible that these boronic acid hydrates may function as phosphate mimics and $M_1$ modules as proposed in FIG. 2. This hydration property was utilized by Baggio et al. (1997) where a hydrated boronic acid functioned as a transition state analog inhibitor functionality for arginase. These researchers evaluated the inhibited complex by x-ray and showed that the hydrated boronic acid functionality formed two hydrogen bonds with the active site catalytic Glu-277 carboxyl side chain and one of the other hydrated boronic acid OH groups interacted with two catalytic metals, $Mn^{2+}$, in the active site. These binding interactions are closely analogous to those proposed in protein kinase active sites, i.e. hydrogen-bonds to the catalytic Asp side chain carboxyl group and interactions with the active site $Mg^{2+}$ metals (see FIGS. 2 and 4). The use of boronic acids for protein kinase inhibitors has not been explored previously.

In the area of pentapeptide-based PKA inhibitors, the boronic acid functionality has been prepared and tested as a potential $M_1$ module utilizing the four inhibitors 21-24 shown in Table III (see Hsiao & Hangauer, 1998, for some of the chemistry used to prepare these compounds).

TABLE III

PKA INHIBITION RESULTS WITH BORONIC ACID-CONTAINING PEPTIDE INHIBITORS

| Ac-RRGXI-NH$_2$, X = | IC$_{50}$ μM (cond. L, 0 h preincubation) | IC$_{50}$ μM (cond. L, 4 h preincubation) | IC$_{50}$ μM (cond. C, 0 h preincubation) | IC$_{50}$ μM (cond. C, 4 h preincubation) |
|---|---|---|---|---|
| 20 Ala | 278 (K$_i$ = 9 μM) | 417 | 41 (K$_i$ = 25 μM) | 50 |
| 21 (L-boronic acid, short chain) | 249 | *500 μM 34% inh | 764 | *2000 μM 19% sti |
| 22 (D-boronic acid, short chain) | 81 | *65 | *1753 | *2000 μM 71% sti |
| 23 (boronic acid, longer chain) | 398 | 133 | 2000 μM 16% inh | *2000 μM 5% inh |
| 24 (boronic acid, longest chain) | 1000 μM 33% inh | 1000 μM 44% inh | 2000 μM 6% sti | 1734 μM |

*Very distorted IC$_{50}$ curve: Suggests Inhibitor is also a substrate.
L = Literature Mimetic Assay Conditions.
Inh = Inhibition.
C = Cellular Mimetic Assay Conditions.
Sti = Stimulation.

The structure identified in Table III as Ac-RRGXI-NH$_2$ is SEQ. ID. No. 4. While testing these boronic acid-containing PKA inhibitors, the corresponding pentapeptide pseudosubstrate inhibitor 20 was included as an internal control while investigating time-dependent inhibition as shown in Table III. Under Literature Mimetic assay conditions, and no preincubation, the initial results suggested that the shortest chain L-amino acid 21 was binding with the same affinity as the pseudosubstrate inhibitor 20 (i.e. K$_i$ approximately 9 μM). As this side chain was increased in length (to 23 and then 24) binding affinity appeared to decrease. When the stereochemistry of the unnatural amino acid was inverted from L in 21 to D in 22, binding affinity appeared to increase 3-fold. This improvement in binding may occur as a result that the boronic acid OH in 21 which is positioned at the same chain length as L-homoserine, whereas the natural substrate, L-serine, has a one carbon shorter side chain. Modeling results with the PKA ternary structure indicated that the boronic acid OH can be retracted back somewhat by inverting the α-carbon stereochemistry from L in 21 to D in 22 and then repositioning the side chain to more closely mimic the positioning of the natural substrate L-serine OH adjacent to the catalytic residues (Asp-166 and Arg-168). The modeling results were subsequently supported by the finding that, upon incubation of PKA with these inhibitors for up to 4 hours without adding the competing peptide substrate (Kemptamide: LRRASLG-NH$_2$) (SEQ. ID. No. 5), both 21 and 22 function as substrates with the D-diastereomer 22 being phosphorylated faster.

The fact that these boronic acid inhibitors are also substrates, became much more obvious by the greatly distorted IC$_{50}$ curves obtained under the Cellular Mimetic conditions, both with and without preincubation (both PKA and src are more active enzymes under the Cellular Mimetic conditions than under Literature Mimetic conditions). In the assay used to obtain these results, the $P^{32}$ phosphorylated Kemptamide product (25 generated from γ-$P^{32}$ ATP) was isolated at the end of the substrate incubation period by binding to phosphocellulose filter paper via the three cationic groups (two Arg residues and the N-terminus) and the level of phosphorylated product isolated on the paper is then measured by liquid scintillation counting (cpm units). The boronic acid inhibitors 21-24 have two Arg residues in their sequence and therefore will bind to the phosphocellulose paper in addition to Kemptamide (although not as consistently or completely due to one less positive charge). Consequently, when analyzed as inhibitors, the amount of phosphorylated Kemptamide produced was not only counted, but also the amount of phosphorylated inhibitor simultaneously produced (e.g. see 26 below). The net result is that distorted $IC_{50}$ curves are obtained which show net "stimulation" at higher inhibitor concentrations in some cases. The D diastereomer 22 gives the greatest apparent "stimulation" (71%) when preincubated with PKA for 4 hours under Cellular Mimetic conditions followed by the L diastereomer 21 (19%) and then the one carbon homolog 23 (5%) indicating that all three compounds are substrates for PKA (Table III). The underlying substrate behavior of these "inhibitors" makes an accurate measurement of their inhibition potency impossible with the current assay. However, it does appear from the data that homologating/extending the boronic acid functionality with $CH_2$ groups (homologations/extensions with boronic acid non-peptide src inhibitors may also be carried out) decreases the binding affinity and ability of the compound to function as a substrate.

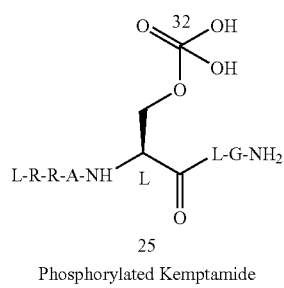

25
Phosphorylated Kemptamide
Compare with

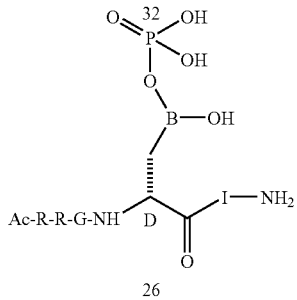

26
Phosphorylated 22

Figure 4:
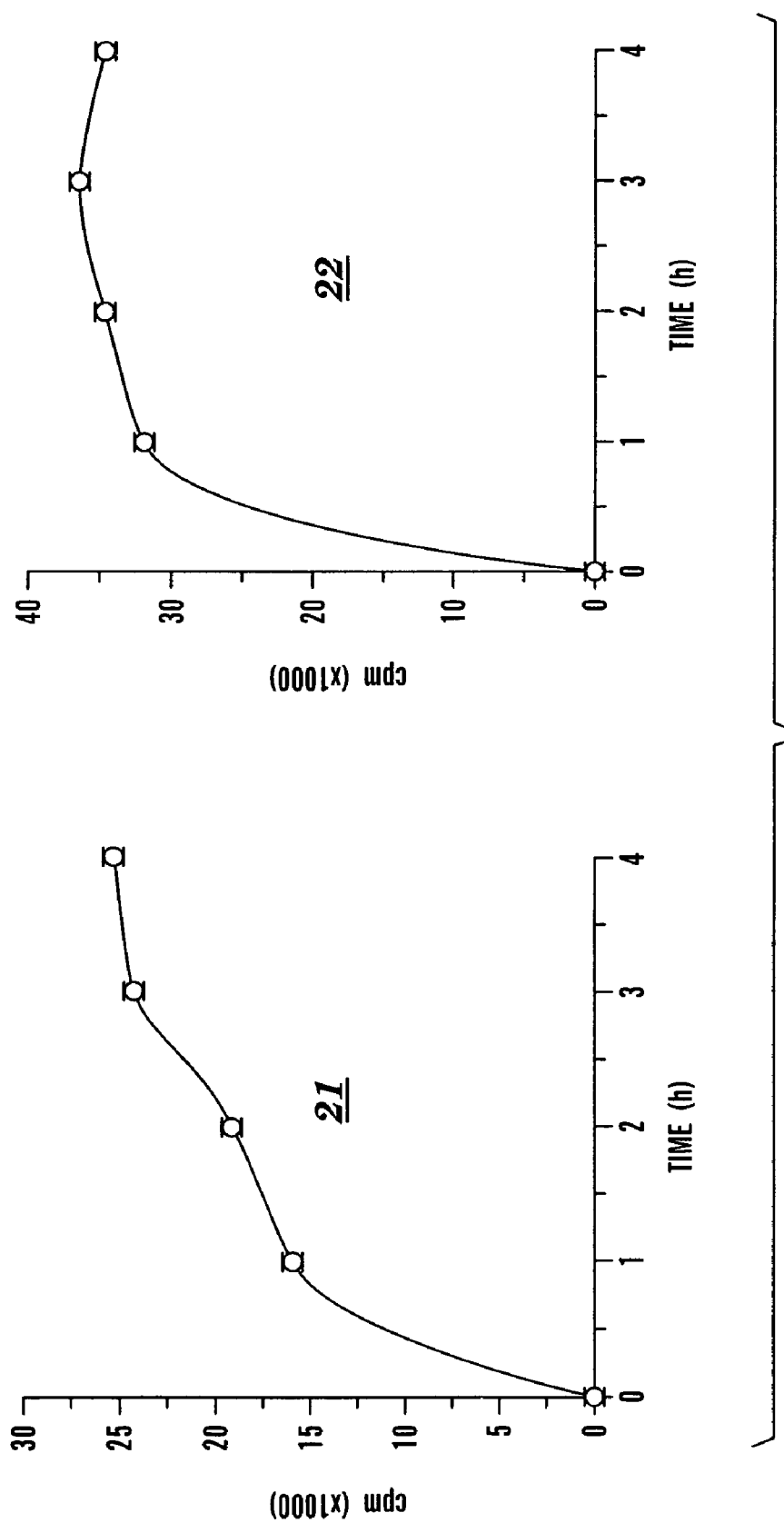
FIG. 4 shows that the boronic acid "inhibitors" 21 and 22 were shown to be substrates for PKA.

Phosphorylated Kemptamide is SEQ. ID. No. 6. The boronic acid "inhibitors" 21 and 22 were shown to be substrates for PKA by running the same assay, but without adding Kemptamide, and stopping the reaction at various time points as shown in FIG. 4. The graphs show their respective rates and levels of phosphorylation with the typical loss of initial velocity kinetics with time (due to substrate depletion and end product inhibition), analogous to a standard L-Ser substrate such as Kemptamide. The comparison of 21 to 22 shown was done in the same assay run, at identical boronic acid substrate concentrations, and with identical Cellular Mimetic assay solutions so that the cpm units could be directly compared. The graphs show that initial velocity conditions were lost within one hour for D isomer 22 whereas the linearity appears to have been lost somewhat slower with the L isomer 21 suggesting a slower consumption of starting material. The fact that the boronic acid moiety would be phosphorylated by PKA was surprising, but it is even more surprising that the phosphonic-boronic acid mixed anhydride produced (e.g. 26) was stable enough to survive the pH 7.2/37° C. assay incubation and then be isolated by binding to phosphocellulose paper after acid quenching of the reaction with 10% TCA and washing the phosphocellulose paper with 25 mM phosphoric acid (3×). An STN substructure search was run on mixed anhydrides of phosphoric and boronic acids and found only three references to experiments and theoretical calculations for the analogous putative (but not proven) anhydride formed from boric acid and phosphoric acid as a solid surface impregnated catalyst for the partial oxidation of ethane to acetaldehyde at 823° K. (Zhanpeisov & Otsuka, 1992, Otsuka et al., 1992, Murakami et al., 1990). However, this highly unusual anhydride has never before been synthesized free of a solid surface, isolated or characterized. Thus, this is a novel enzymatic reaction and chemical entity with interesting possibilities for protein kinase inhibitor designs.

The src and PKA pentapeptide scaffold tethered $M_1$ evaluations described above have resulted in the identification of a variety of orienting $M_1$ groups which could be used for screening potential non-peptide scaffolds as indicated in Step 1 (FIG. 1). The boronic acid (from 22), the phosphonate (from 14), and the sulfamic acid (from 8) were initially chosen from the menu of potential $M_1$ modules for the src non-peptide scaffold screening. Among these choices, the boronic acid $M_1$ group has proven effective for Step 1 screening of non-peptide scaffolds.

The most useful crystal structures available for the design of non-peptide src inhibitors, which do not compete with ATP, are the native src structure and the IRTK:peptide:AMP-PNP ternary structure. For all of the modeling studies discussed below, the SYBYL molecular modeling software package is used on a Silicone Graphics Workstation.

Since the src and IRTK structures are only used as qualitative guides in designing the non-peptide scaffolds and combinatorial libraries, the active sites along with two layers of surrounding residues were carved out from the native src and IRTK ternary structures, analogous to the previous PKA modeling studies. The IRTK:peptide:AMP-PNP ternary structure active site region was used as the template structure to guide the building of the src residue sequence 424-418 back onto the src structure using the comparative homology modeling technique (see Hutchins & Greer, 1991). These residues were disordered in the native src crystal structure and therefore not visible by x-ray. The residues were reintroduced because they help form the P+1 to P+3 binding sites for peptide substrates which are important for some of the modeling studies. The analogous residues in the IRTK ternary structure are seen by x-ray and directly interact with the bound peptide substrate. In fact, it is probably the presence of the bound peptide substrate which induces order in the positioning of this sequence so that it is visible by x-ray. The src pentapeptide substrate Ac-Ile-Tyr-Gly-Glu-Phe-$NH_2$ (SEQ. ID. No. 1) (Nair et al., 1995) was then docked into the src active site again using the IRTK ternary structure as a template. Small adjustments were then manually made to partially clean up this complex, all of the hydrogen atoms were added, appropriate formal and partial charges (calculated via the Gasteiger Marsili method) were added, and then the entire complex was subjected to 300 iterations of molecular mechanics minimization using the Tripos force field, analogous to the previous PKA modeling procedure. A schematic representation of this modeled complex is given in FIG. 5. Any inaccuracies in this src:peptide and the src:inhibitor models are accommodated by experimentally evaluating a range of side chains, the number and diversity of which is scaled roughly to the level of uncertainty for the structure of their particular binding region in the src model active site (see later), in a combinatorial fashion.

Figure 5:
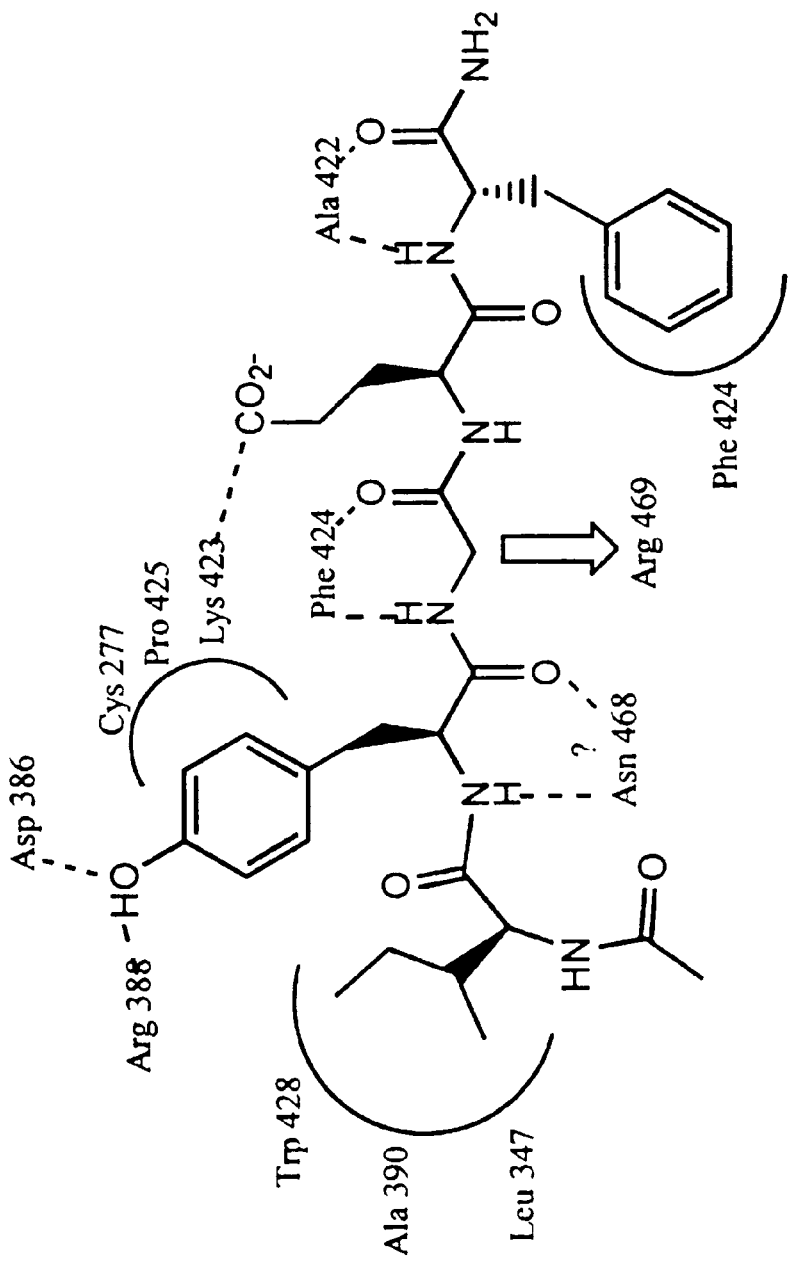
FIG. 5 demonstrates the binding interactions of src substrate Ac-Ile-Tyr-Gly-Glu-Phe-$NH_2$ (SEQ. ID. No. 1) in model src active site.

As shown in FIG. 5 the residues 424-418 built back into the src interact with the P+1 to P+3 substrate residues, Gly-Glu-Phe-$NH_2$ respectively, through beta sheet type hydrogen bonding interactions with the substrate main chain (analogous to the IRTK peptide substrate). Lys 423 engages in two important interactions: 1) the $\beta$ and $\gamma$ $CH_2$ groups fold over the top of the P 0 Tyr phenyl ring engaging in a hydrophobic binding interaction and then 2) the remaining $CH_2$—$CH_2$—$NH_3^+$ of this side chain extends away to form a salt bridge with the P+2 Glu side chain as indicated. The rest of the P 0 Tyr hydrophobic binding pocket is formed by Pro 425 under the phenyl ring and part of the Cys 277 side chain above the phenyl ring. Using a large combinatorial peptide src substrate library, Songyang et al. (1995) found that the most commonly chosen side chain for the P+1 position was Gly followed by Glu. The present model indicates that a P+1 Glu side chain may form a salt bridge with nearby Arg 469 as indicated in FIG. 5. Previously, researchers found that only Glu was chosen for the P+2 position and the present model indicates that this side chain forms a salt bridge with the Lys 423 side chain. At the P+3 position Phe was very strongly preferred and the model indicates that this side chain forms a stacking interaction with the Phe 424 side chain. At the P-1 position Songyang et al. found that Ile was the most preferred residue followed by Val and then Leu. The model shows a hydrophobic pocket for binding the P-1 side chain formed mainly by Trp 428, Ala 390 and Leu 347. One might expect that the P 0 Tyr side main chain will strongly interact (though hydrogen bonding) with the active site in a catalytically competent complex because enzymes often form more critical interactions in this region close to where the reaction will be occurring. The IRTK ternary complex does not show a good hydrogen bond to either the P 0 Tyr NH or carbonyl. The nearest candidate residue for this interaction in the IRTK structure is Asn 1215 wherein the side chain $NH_2$ is 3.71 A° from the Tyr carbonyl oxygen. When the IRTK ternary structure is overlaid onto the src native structure, using the four residues mentioned in the Background and Significance section, Asn 468 from the src structure was found to be positioned very close to the analogous IRTK Asn 1215. This suggests that this conserved residue is performing an important role and might move a little closer (i.e. about 1 A°) to the substrate P 0 NH and carbonyl in a catalytically active complex and form the hydrogen bonding interactions indicated in FIG. 5. Finally, the catalytic Arg 388 and Asp 386 are correctly positioned in the src model to catalyze the transfer of the $\gamma$-phosphate from ATP to the Tyr OH.

The src:peptide substrate complex can now be used to model potential non-peptide scaffolds and determine preferred substitution positions for the specificity elements, all with an appropriately attached $M_1$ functionality, before choosing new scaffolds to experimentally evaluate. The IRTK:peptide:AMP-PNP ternary structure can also be used to model these potential scaffolds and preferred substitution positions. These scaffolds have broad utility for the development of selective PTK inhibitors by further developing them with appropriate specificity elements following the strategy outlined in FIG. 1.

Figure 6:
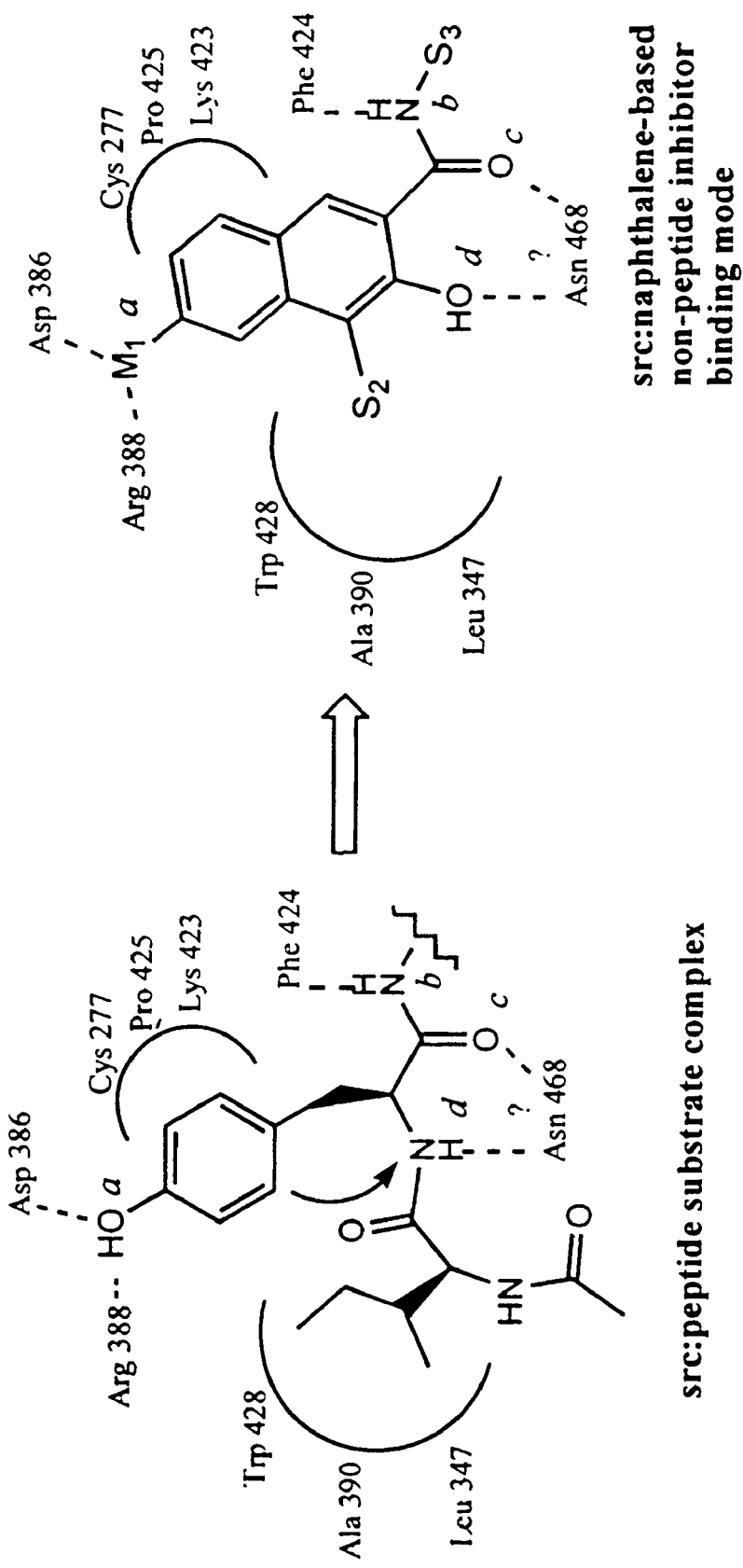
FIG. 6 shows the design of naphthalene-based src inhibitor scaffolds.
Figure 7:
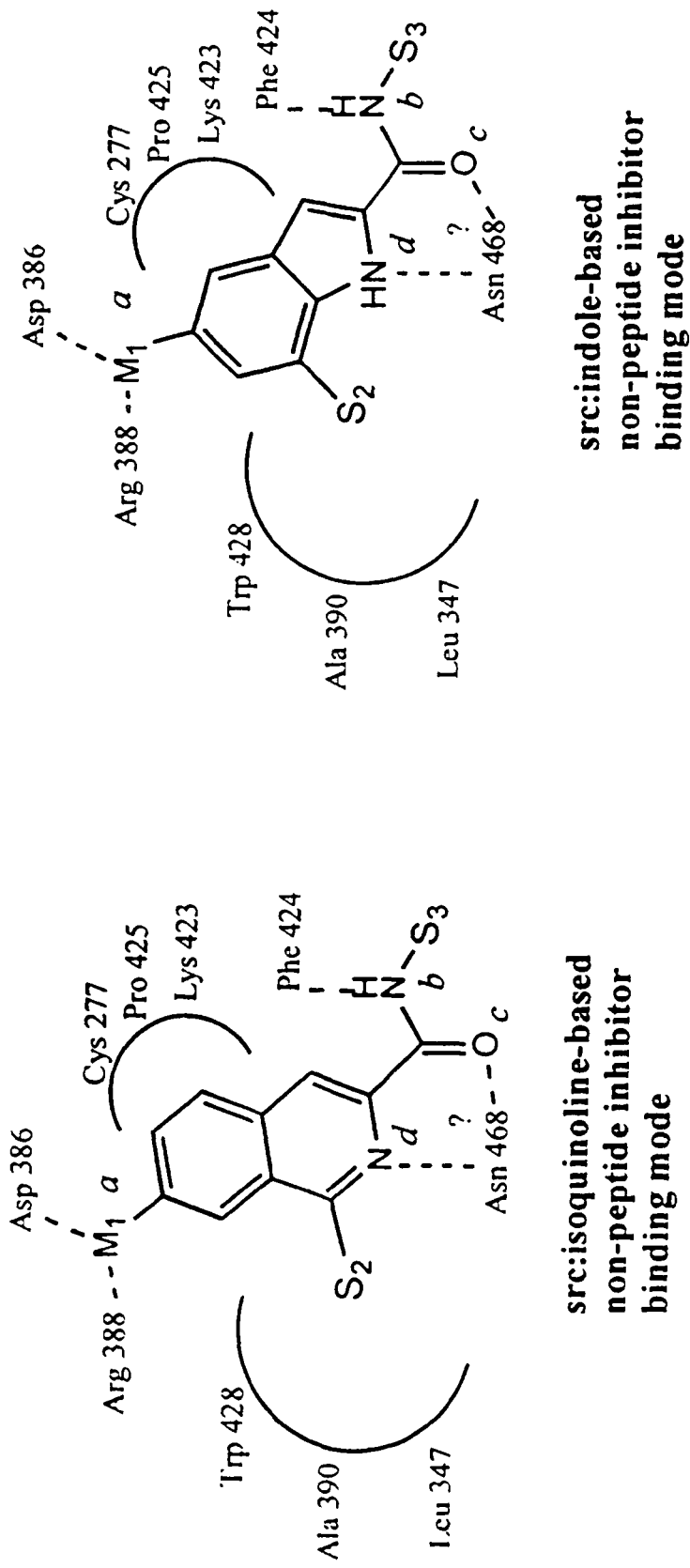
FIG. 7 shows the design of isoquinoline and indole-based src inhibitor scaffolds.

The first non-peptide scaffold evaluated with this src:peptide substrate model was the naphthalene scaffold. This is the first use of bicyclic aromatic scaffolds for non-peptide PTK inhibitors, which do not compete with ATP. The utility of a naphthalene scaffold for this purpose was demonstrated by developing a non-peptide inhibitor of the IRTK and EGF receptor PTK (Saperstein et al., 1989). The IRTK ternary complexes were subsequently used to adapt this scaffold for src inhibition (see Marsilje et al., 2000). The naphthalene scaffold was docked into the src active site by first carrying out a least squares fitting of atoms a-d onto the peptide substrate as indicated in FIG. 6. In this way the naphthalene scaffold is related to the peptide substrate by the cyclization shown by the arrow in FIG. 6 and an appended OH as a substitute for the substrate Tyr NH. This is essentially the same process used to dock this scaffold into the IRTK structure as described in Marsilje 2000. The peptide substrate was then deleted from the active site, various $M_1$ functional groups and specificity elements $S_2$ and $S_3$ were then added to the scaffold as indicated and the complexes were then individually minimized for 300 iterations. This same process was also used to design the isoquinoline and indole scaffolds whose binding modes are indicated in FIG. 7.

In all of these modeled complexes selectivity element $S_2$ consists of various hydrophobic side chains which can bind in the same pocket as the substrate P-1 Ile side chain and selectivity element $S_3$ consists of various molecular fragments which can bind in the P+1 to P+3 region of the peptide substrate binding sites (FIG. 5). Since the active site region where $M_1$ binds is highly conserved among all of the protein kinases, the small menu of $M_1$ functional groups previously identified using peptide scaffolds served as the initial $M_1$ groups for attachment to the scaffolds at the indicated positions. Of the two selectivity elements binding sites, the structure of the hydrophobic binding cavity for $S_2$ is known with greater confidence in the src model than is the P+1 to P+3 binding region for $S_3$. This is because the $S_3$ binding site was constructed partially by comparative homology modeling whereas the $S_2$ site is largely unchanged from the structure determined by x-ray for native src. In view of these varied levels of confidence in the modeled binding sites for $M_1$, $S_2$ and $S_3$, the combinatorial library diversity is scaled such that the greatest variety and number of side chains in the combinatorial libraries are at the $S_3$ site followed by the $S_2$ site and then $M_1$.

The src results using $M_1$ functional groups to experimentally identify promising non-peptide scaffolds are listed in Table IV. The data in Table IV allows a number of conclusions to be drawn: 1) Low, but measurable, inhibition potency can be obtained with an appropriate $M_1$ group attached to a scaffold (e.g. 27 and 38). 2). A 1 mM inhibitor concentration for this type of screening is higher than desirable but 100 μM is too low. Screening of compounds with scaffolds bearing an $M_1$ group would optimally be conducted at 500 μM. 3) The boronic acid, sulfamic acid and phosphonic acid $M_1$ functional groups, which had been identified using the PKA pentapeptide scaffold (22, Table III and 8, Table I) or the src pentapeptide scaffold (14, Table II), respectively, give measurable activity when placed at the 2-position of the naphthalene ring (27, 28 and 30, respectively), the preferred position for $M_1$ identified in the model naphthalene inhibitor:src complex (FIG. 6). Moving the boronic acid or phosphonic acid $M_1$ groups to the 1 position (32 or 33) reduced activity. 4) The related $M_1$ sulfonamide functionality, which was poor on the PKA pentapeptide scaffold (7 and 9, Table I) is also poor when appended to the 2 (31) or 1 (34) position of the naphthalene scaffold. The sulfonic acid analog at the naphthalene 2 position (29) is completely inactive, even at 1 mM. 5) The naphthalene scaffold can be replaced with a benzofuran (35) or a benzothiophene (36) scaffold without a noticeable reduction in activity when the boronic acid $M_1$ group is positioned analogous to the 2 position on a naphthalene. 6) The boronic acid $M_1$ group also provides active compounds when appended to the isoquinoline (37) or indole (38) scaffolds at the positions indicated by modeling results (FIG. 7). However, the indole scaffold is clearly favored over the isoquinoline scaffold suggesting that a hydrogen bond donating ability to Asn 468 (see FIG. 7) is important for higher activity (this would require the isoquinoline to be protonated which is disfavored by the adjacent electron withdrawing ester group). This conclusion is also supported by considering that a peptide substrate may position a hydrogen bond donating peptide bond NH at a similar position (FIG. 6) and by finding that an equivalently positioned phenolic OH (FIG. 6) improves potency (phenolic OH groups are much better hydrogen-bond donors than acceptors) 8) When directly compared to other $M_1$ groups the boronic acid group is superior (e.g. 27 vs. 28-31, 38 vs. 39). 9) A biphenyl scaffold modeled into the src and IRTK active sites and found promising binding modes for this scaffold. Combinatorial libraries were developed with the biphenyl scaffold (see Pavia et al., 1996), and the modeling results were encouraging. Therefore, the para (40) and meta (41) isomers were evaluated with the boronic acid $M_1$ group. Both biphenyl compounds showed potency equivalent to the best naphthalene boronic acid (27) and therefore provide another scaffold geometry (the two phenyl rings are not planar) for further evaluation and development.

Since the bare scaffolds, with only an $M_1$ group appended, often have low binding affinity, the $IC_{50}$ and $K_i$ values for the 2-naphthalene boronic acid and sulfamic acid inhibitors were determined to ensure that a typical dose/response $IC_{50}$ curve is obtained. This analysis provided the typical shape dose/response curves seen with more potent inhibitors. The $IC_{50}$ and $K_i$ values of these simple inhibitors also confirmed that the boronic acid inhibitor 27 is the more potent than the sulfamic acid analog 28 and has a $K_i$ of about 554 µM.

The next issue addressed with these simple inhibitors before proceeding to elaborate them further was their mode of inhibition, specifically whether they are ATP-competitive inhibitors. In the case of the naphthalene inhibitors 27 and 28, their $IC_{50}$ values were monitored as the ATP concentration was increased in three steps up to 1 mM. As a comparison, the $IC_{50}$ of the pentapeptide phosphonic acid src inhibitor 14 (Table II) was also monitored. If any of these inhibitors were competing with ATP, then their $IC_{50}$ values should have increased proportionally with the ATP concentration (i.e. the dashed line). As shown, the $IC_{50}$ values for all three inhibitors remained essentially constant as the ATP concentration was increased demonstrating that they are not ATP-competitive inhibitors. A very similar, but much less costly (commercial src is expensive), analysis was conducted with the indole boronic acid inhibitor 38. In this case, the % inhibition was monitored with 38 at a constant 500 µM inhibitor concentration but with increasing ATP concentrations of 200, 500 and 1,000 µM. Once again the inhibitor potency was not reduced by the increasing ATP concentration demonstrating that 38 is also non-ATP competitive.

The initial results obtained in Step 1 suggests that it is possible to identify promising scaffolds for further elaboration with this procedure. The biggest uncertainty with Step 1 is that some of the scaffolds identified in this way might not be binding in the fashion suggested by the prior modeling evaluations. This is essentially a "false positive" problem. These "false positives" will likely fail in Step 2, when they are evaluated for improved binding using the modeled complexes as a guide. Some false positive results can be accepted in Step 1 because the bare scaffolds with only the $M_1$ group attached are easily obtained. For further inhibitor development, one may return to Step 1 each time new scaffolds are needed to carry through Steps 2 and 3. The best $M_1$ generated can be used each time Step 1 is repeated. Currently, the boronic acid $M_1$ group is preferred since it has a proven ability to give measurable activity with bare scaffolds. Also the boronic acid $M_1$ group offers multiple interesting possibilities for covalent and non-covalent interactions with the conserved catalytic residues since it can: 1) hydrate, 2) form borate complexes with electron rich active site atoms, and/or 3) be phosphorylated and then react with active site nucleophiles or engage in additional non-covalent interactions. From the data in Table IV, the naphthalene and indole scaffolds were chosen as $M_2$ for the first efforts in Step 2 (the biphenyl scaffold is also a preferred scaffold). It is also worth mentioning that naphthylalanine and analogs can be successfully substituted for the P 0 tyrosine in src peptide substrates (e.g. see Alfaro-Lopez et al., 1998) further supporting the notion that naphthalene and related scaffolds can bind at the P 0 site.

TABLE IV

INITIAL STEP 1 RESULTS
% SRC INHIBITION IN CELLULAR MIMETIC ASSAY

| Inhibitor | % Inhibition of 2 mM RR-src at Inhibitor Concentration ( ) |
|---|---|
| 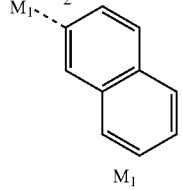 | |
| 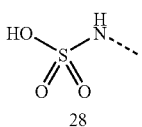 27 | 59 (1 mM)<br>13 (100 µM)<br>$IC_{50} = 950$ µM<br>$K_i = 554$ µM<br>NON-ATP<br>COMPETITIVE |
| 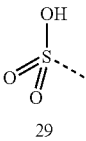 28 | 31 (1 mM)<br>$IC_{50} = 1.6$ mM<br>$K_i = 963$ µM<br>NON-ATP<br>COMPETITIVE |
| 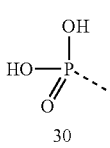 29 | 0 (1 mM) |
|  30 | 14 (1 mM) |

TABLE IV-continued

INITIAL STEP 1 RESULTS
% SRC INHIBITION IN CELLULAR MIMETIC ASSAY

| Inhibitor | % Inhibition of 2 mM RR-src at Inhibitor Concentration ( ) |
|---|---|
| 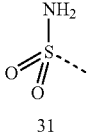 31 | 0 (100 μM) |
| 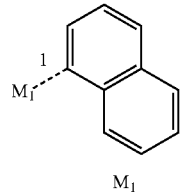 $M_1$ | |
| 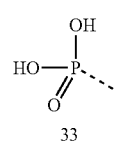 32 | 0 (100 μM) |
| 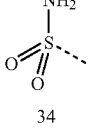 33 | 1 (1 mM) |
| 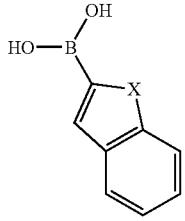 34 | 0 (100 μM) |
| 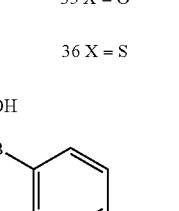 35 X = O | 10 (100 μM) |
| 36 X = S | 12 (100 μM) |
| 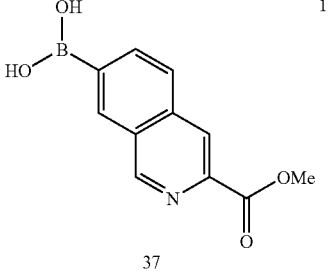 37 | 13 (500 μM) |
| 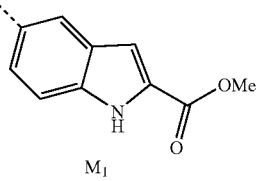 $M_1$ | |
| 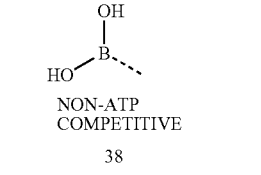 NON-ATP COMPETITIVE 38 | 62 (500 μM) |
| 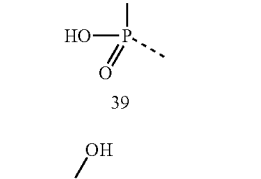 39 | 11 (500 μM) |
| 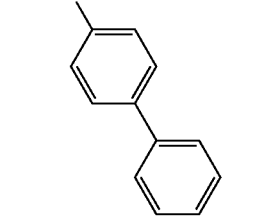 40 | 13 (100 μM) |
| 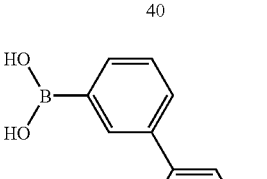 41 | 14 (100 μM) |

- - - - = Attaching bond.

In comparing the naphthalene vs. indole scaffold results with a boronic acid $M_1$ group (i.e. 27 vs. 38, Table IV) the indole hydrogen bond donating NH and/or the adjacent ester group appeared to be the reason for the enhanced potency. Consequently, for Step 2 one of the first attempts was to add a hydroxyl group and an amide (with $S_2$) to the naphthalene scaffold at the adjacent positions as suggested by the modeling results (FIG. 6). For the indole scaffold one priority was to prepare some amide analogs to see if potency can be increased with the $S_2$ specificity element (FIG. 7). In order to facilitate the synthesis of these initial analogs, an OH was temporarily substituted for the boronic acid $M_1$ group. The OH group is also known to interact with the catalytic residues, as required for an $M_1$ group, because it is the natural substrate M₁ whose phosphorylation rate is accelerated by interactions with the catalytic residues. The results obtained for some of the initial analogs are given in Table V along with a side by side comparison, in the Cellular Mimetic src assay, to two literature src inhibitors 50 and 51 which are reported be non-ATP competitive. Some of these results and additional analogs are described in Marsilje 2000.

Inhibitor 50 and analogs (Huang et al., 1995), were of particular interest because the iminochromene scaffold is closely related to the naphthalene scaffold and its binding mode would be expected to be very similar based upon the model (FIG. 6). Partly because of this close analogy, the amides of hydroxyanilines with the naphthalene and indole scaffolds were examined as shown in Table V. Also, the modeling studies with these hydroxyaniline amides derivatives in the src active site indicated that the hydroxyl group may be able to engage in a hydrogen bonding interactions with the src Phe 424-Ala 422 backbone peptide bonds analogous to peptide substrates (see FIG. 5). These modeling studies also indicated that the homologous hydroxybenzylamides should be active and, more importantly, provide a substitution position (i.e. the benzylic carbon) for appending side chains to bind in the P−1 side chain pocket (e.g. to Arg 469, FIG. 5).

The data in Table V allow the following conclusions to be drawn: 1) Adding an amide extension onto both the naphthalene and indole scaffolds can increase potency as predicted by the models for these scaffolds bound in the src active site (approximately 5-fold in the cases of 42 vs. 43-meta and 47 vs. 48). 2) Adding a hydroxyl group to the naphthalene scaffold adjacent to the amide increases potency (about 5-fold, 43-meta vs. 44) as predicted by the src model, and also suggests Asn 468 does hydrogen bond with this OH. 3) Moving the M₁ OH group from the position predicted to be best in the src model to the adjacent position reduces potency by one order of magnitude (43-meta to 45). 4) The indole scaffold is less responsive than the naphthalene scaffold to the regiochemistry of the hydroxyaniline extension (48 vs. 43). 5) The naphthalene and the indole scaffolds accept the one carbon homologation provide by using hydroxybenzylamides (46 vs. 43 and 49 vs. 48). 6) The two M₁ hydroxy regioisomers of the naphthalene scaffold are both non-ATP competitive (see Marsilje 2000). 7) All of the methyl hydroxyaniline and hydroxybenzylamide inhibitors were found to be less active suggesting that the hydroxyl group in the amide extension is functioning as a hydrogen bond donor. In this regard, it is worth mentioning that in another src peptide substrate combinatorial library study Ser and Thr were identified as two of the most preferred residues at the P+2 position (Alfaro-Lopez et al., 1998) suggesting that there are other binding opportunities for an amide extension OH other than to the Phe424-Ala 422 peptide bonds suggested by the modeling studies. 8) The most potent non-ATP competitive, non-peptide, src inhibitor previously disclosed in the literature (50) is not nearly as potent as reported when tested under the Cellular Mimetic assay conditions (IC₅₀=118 nM reported by Huang et al., 1995 vs only 30% inhibition at 100 μM) and is less potent than a number of the current inhibitors (e.g., 43-meta) including the most analogous inhibitor (50 vs. 45). The structure-activity-relationship (SAR) reported for hydroxy regioisomers of 50 in their assay (Huang et al., 1995) also does not correspond with the SAR which was obtained for the related naphthalene inhibitors. For example, the iminochromene analog of the most potent naphthalene inhibitor 43-meta is 230-fold less potent than 50 in their src assay. An important advantage of the naphthalene scaffold over the iminochromene scaffold is that it allows a highly desirable S₂ specificity element to be added for accessing the P−1 hydrophobic site (see FIG. 6) whereas the analogous position can not be substituted on the iminochromene scaffold because the position is occupied by the ring oxygen atom.

TABLE V

INITIAL STEP 2 RESULTS
% SRC INHIBITION IN CELLULAR MIMETIC ASSAY

| Inhibitor | % Inhibition of 2 mM RR-src at Inhibitor Concentration ( ) |
|---|---|
| (M₁) [structure: naphthalene with HO- substituent, -C(=O)OMe group, and OH, labeled 42] (M₁) | 47 (100 μM) |

TABLE V-continued

INITIAL STEP 2 RESULTS
% SRC INHIBITION IN CELLULAR MIMETIC ASSAY

| Inhibitor | % Inhibition of 2 mM RR-src at Inhibitor Concentration ( ) |
|---|---|
| (M₁) Compound 43, NON-ATP COMPETITIVE | Ortho: 39 (100 μM)<br>Meta: 89 (100 μM)<br>$IC_{50} = 18$ μM, $K_i = 10$ μM<br>Para: 23 (100 μM) |
| Compound 44 | 45 (100 μM) |
| (M₁) Compound 45, NON-ATP COMPETITIVE | 51 (100 μM)<br>$IC_{50} = 170$ μM |
| (M₁) Compound 46 | Ortho: 42 (100 μM)<br>Meta: In progress<br>Para: 42 (100 μM) |
| (M₁) Compound 47 | 40 (500 μM) |

TABLE V-continued
INITIAL STEP 2 RESULTS
% SRC INHIBITION IN CELLULAR MIMETIC ASSAY
| Inhibitor | % Inhibition of 2 mM RR-src at Inhibitor Concentration ( ) |
|---|---|
| (M$_1$) 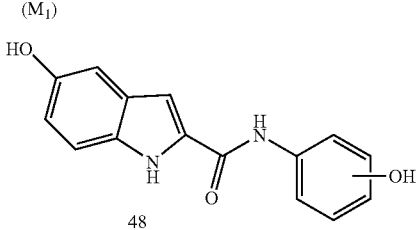 48 | Ortho: 43 (100 μM)<br>Meta: 30 (100 μM)<br>Para: 45 (100 μM) |
| (M$_1$) 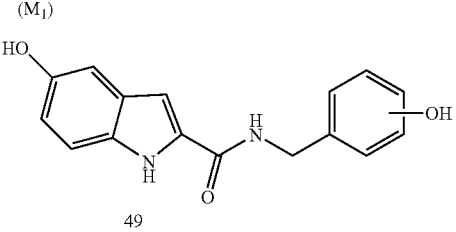 49 | Ortho: 24 (100 μM)<br>Meta: In progress<br>Para: 54 (100 μM) |
| (M$_1$?) 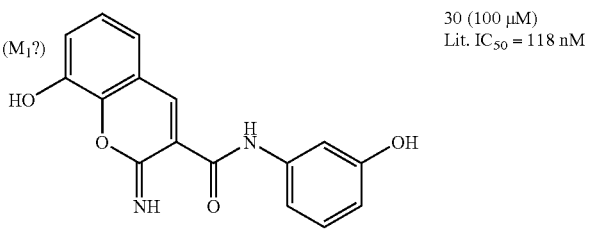 Huang et al 50 | 30 (100 μM)<br>Lit. IC$_{50}$ = 118 nM |
| (M$_1$?) 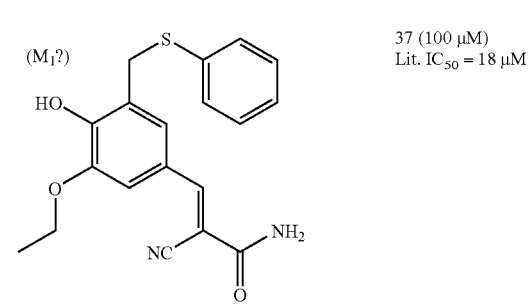 ST 638 51 | 37 (100 μM)<br>Lit. IC$_{50}$ = 18 μM |

TABLE V-continued

INITIAL STEP 2 RESULTS
% SRC INHIBITION IN CELLULAR MIMETIC ASSAY

| Inhibitor | % Inhibition of 2 mM RR-src at Inhibitor Concentration ( ) |
|---|---|
| 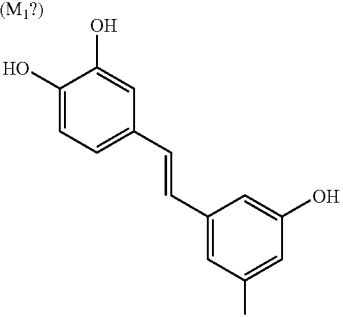<br>($M_1$?)<br>Piceatannol<br>52 | 41 (100 µM)<br>Lit. $IC_{50} = 66$ µM<br>for p56$^{lck}$ |

The inhibitor potencies in the src Cellular Mimetic assay can be further calibrated against other literature non-ATP, non-peptide src inhibitors. Two additional examples are 51 (ST 638, Shiraishi et al., 1989) which is a member of the "tyrphostin" family of erbstatin analogs (see Lawrence & Niu, 1998) and the natural product PTK inhibitor piceatannol 52 (Thakkar et al., 1993). In the Cellular Mimetic assay, all of these known inhibitors are less potent than had been reported suggesting that the assay is particularly demanding in terms of achieving high potency. The initial testing of src inhibitors is carried out using a single concentration (in triplicate) because commercial src is too expensive to do full $IC_{50}$ curves on every inhibitor. It should be mentioned, however, that an $IC_{50}$ dose response curve is not linear and the difference between approximately 50% inhibition at 100 µM and a approximately 90% inhibition at 100 µM is actually a factor of 10 and not a factor of 2 (e.g. 45 vs. 43-meta). Consequently, the literature src inhibitors 50-52 are greater than an order-of-magnitude less active than the currently most potent inhibitor 43-meta.

The discrepancies found within the literature reporting the potency of these inhibitors, the sensitivity to assay conditions described earlier with the PKA inhibitors, and the lack of consistency among numerous labs and commercial protein kinase assay kits highlights this overlooked, but crucial, problem in the field. Although the inhibitors produced by the present invention may be more potent under other assay conditions, the Cellular Mimetic assay should be used, which mimics the intracellular physical chemical conditions as closely as possible, as the primary potency and rank order guide for evaluating the inhibitors before choosing compounds to proceed to whole cell or tissue assays. As will be discussed in more detail later, the most potent naphthalene-based inhibitor thus far from the Cellular Mimetic assay (i.e. 43-meta, $IC_{50}$=18 µM and $K_i$=10 µM) is also effective in specifically blocking pp60$^{v-src}$ stimulated cell proliferation with a similar $IC_{50}$ of approximately 25 µM. This result suggests that not only is the Cellular Mimetic src assay predictive, but also that this class of naphthalene-based inhibitors can readily pass through cell membranes and inhibit intracellular src.

Analogs of a number of the naphthalene and indole inhibitors above can be prepared with the boronic acid $M_1$ group in place of the $M_1$ OH and/or with a $S_2$ hydrophobic specificity element attached for binding in the src P-1 site as illustrated in FIGS. 6 and 7. The naphthalene and indole scaffolds can then be taken through to Step 3 as described below. Each time Step 2 is repeated with new scaffolds from Step 1, the best selectivity elements $S_2$ and/or $S_3$ which have been discovered with previous scaffolds will be used in the combinatorial libraries of Step 3. Even though the optimal combination of $M_1$, $S_2$ an $S_3$ is likely to be different for each scaffold, those found optimal with the previous related scaffold (e.g. going from the naphthalene to the indole scaffold) should be suitable for utilization as better initial specificity elements in Step 2 with the new scaffold. The same process will be repeated each time there is a need to try another scaffold until sufficient potency, selectivity and suitable pharmaceutical properties are achieved for the src inhibitors or, subsequently, for inhibitors of additional therapeutically important PTKs.

Some of the chemistry used to prepare the naphthalene inhibitors is described in Marsilje 2000. For attaching a boronic acid functionality in place of a $M_1$ hydroxyl groups in the src inhibitors from Table V, the Pd (0)-catalyzed cross-coupling methodology was used wherein either an aryl triflate (Ishiyama et al., 1997) or an aryl halide (Ishiyama, 1995) can be coupled with the commercially available pinacol ester of diboron. An illustrative example was recently completed as shown in FIG. 8.

Figure 8:
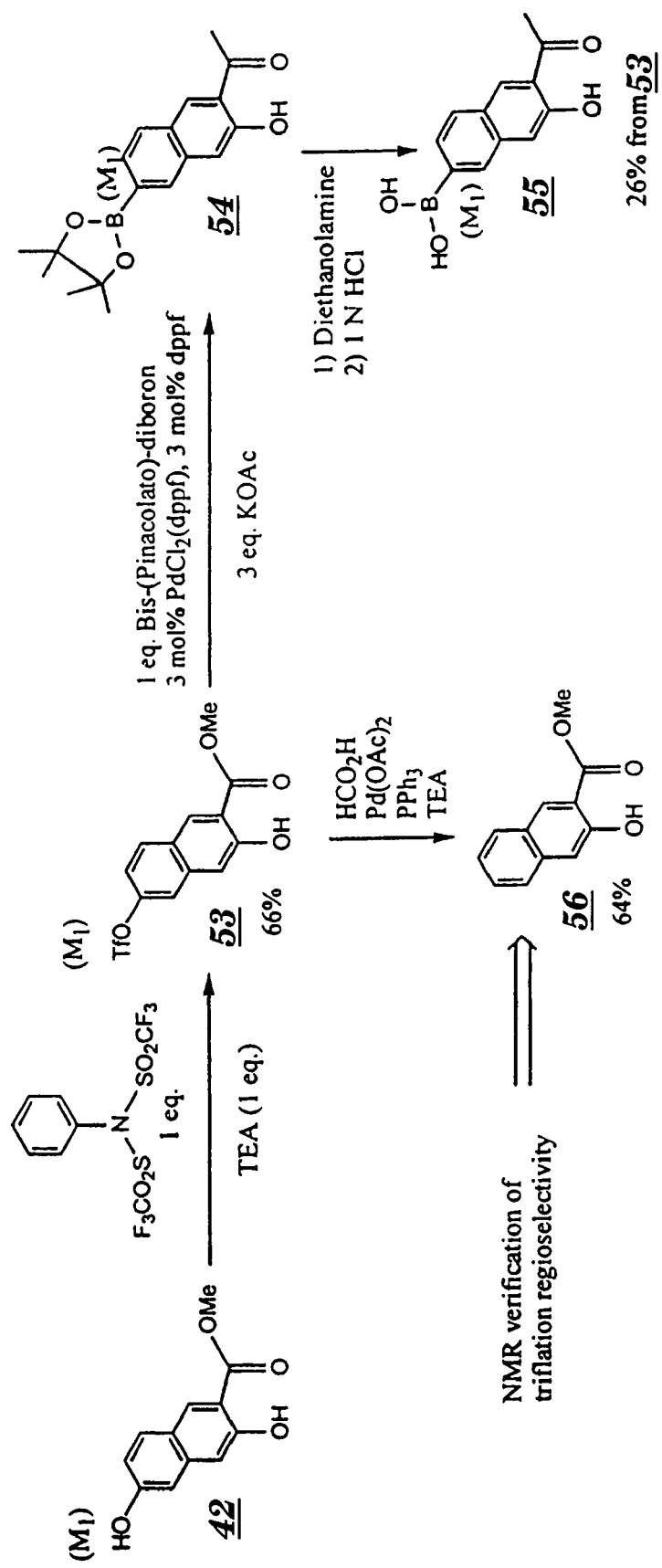
FIG. 8 provides an example of the chemistry used to prepare the naphthalene inhibitors, which is described in Marsilje 2000. A boronic acid functionality can be substituted in place of the $M_1$ hydroxyl group in the src inhibitors from Table V using the Pd (0)-catalyzed cross-coupling methodology, where either an aryl triflate (Ishiyama et al, 1997) or an aryl halide (Ishiyama, 1995) can be coupled with the commercially available pinacol ester of diboron.
Figure 9:
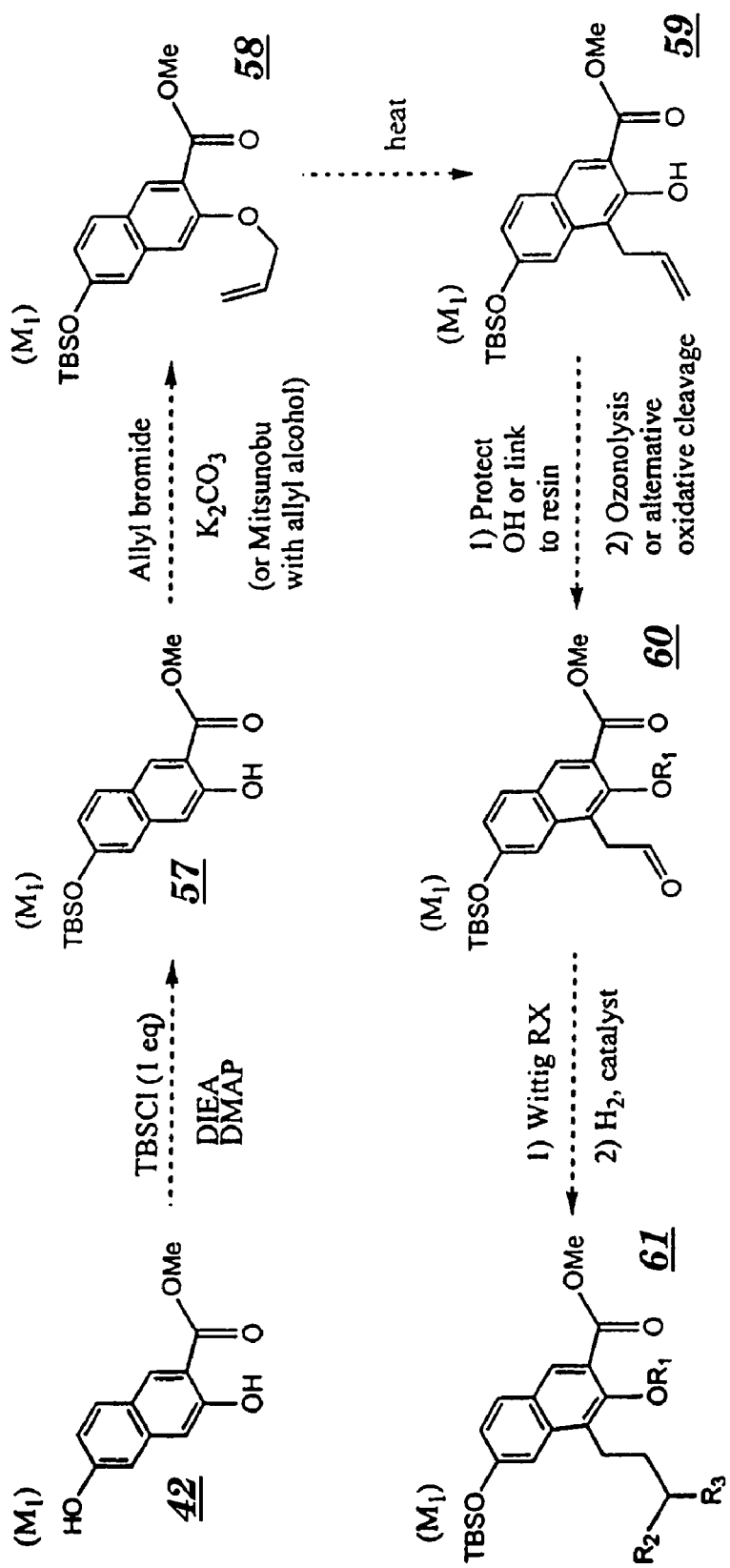
FIG. 9 shows a synthetic scheme that can be followed in order to attach hydrophobic $S_2$ selectivity elements to the naphthalene scaffold.

The example shown in FIG. 8 demonstrates that it is possible to selectively triflate the less hindered OH at the $M_1$ position which has been further proven by removal of the triflate to afford 56 with subsequent $^1$H NMR verification of the substitution pattern. The monotriflate 53 was then taken on to the desired boronic acid 55 as indicated. The same reaction sequence also works well for the regioisomer of 42 which corresponds to inhibitor 45 from Table V. The synthetic scheme shown in FIG. 9 can be followed, in order to attach hydrophobic $S_2$ selectivity elements to the naphthalene scaffold.

Figure 10:
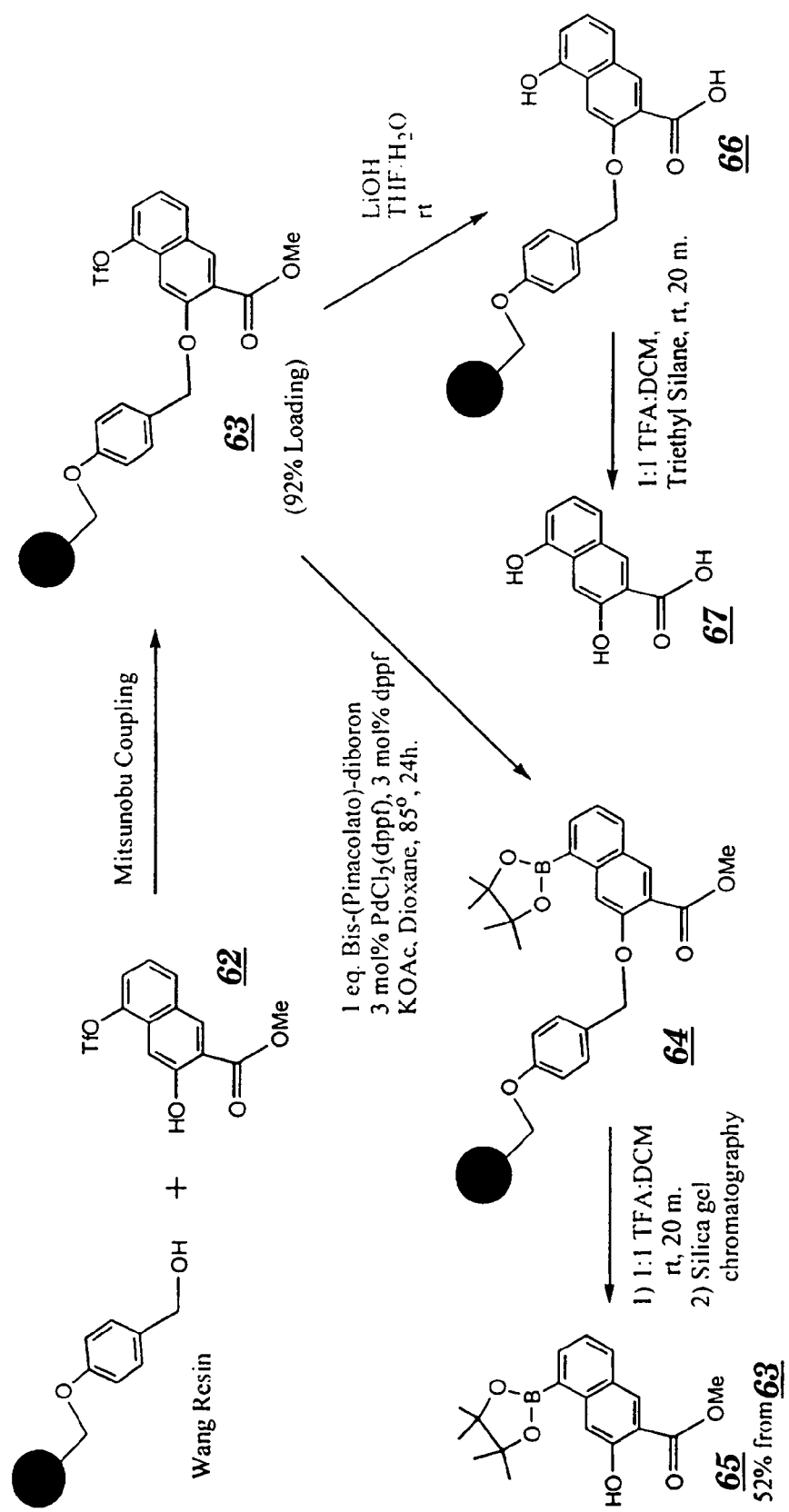
FIG. 10 shows successful model reactions with naphthalene chemistry, which can be converted to the solid phase in preparation for the synthesis of combinatorial libraries using this scaffold in a 96-well plate format. The chemistry has been carried out on the less active naphthalene regioisomer represented by 62 because this compound is readily obtained from commercially available 3,5-dihydroxy-2-naphthoic acid as described in Marsilje 2000.

The naphthalene chemistry can be converted to the solid phase in preparation for synthesizing combinatorial libraries of this scaffold in a 96-well plate format. Thus far, model chemistry has been carried out on the less active naphthalene regioisomer represented by 44 because this compound is readily obtained from commercially available 3,5-dihydroxy-2-naphthoic acid as describe in Marsilje 2000. The successful model reactions to date are shown in FIG. 10.

These model reactions demonstrate that it is possible to couple the naphthalene scaffold to the Wang resin (63) and then carry out chemistry on the triflate [e.g., in this case the Pd (0)-catalyzed cross-coupling to the boronic ester 64] followed by cleavage under mild conditions (65). The ester in 63 can also be saponified for subsequent coupling reactions to form amides containing the $S_3$ selectivity elements.

Figure 11:
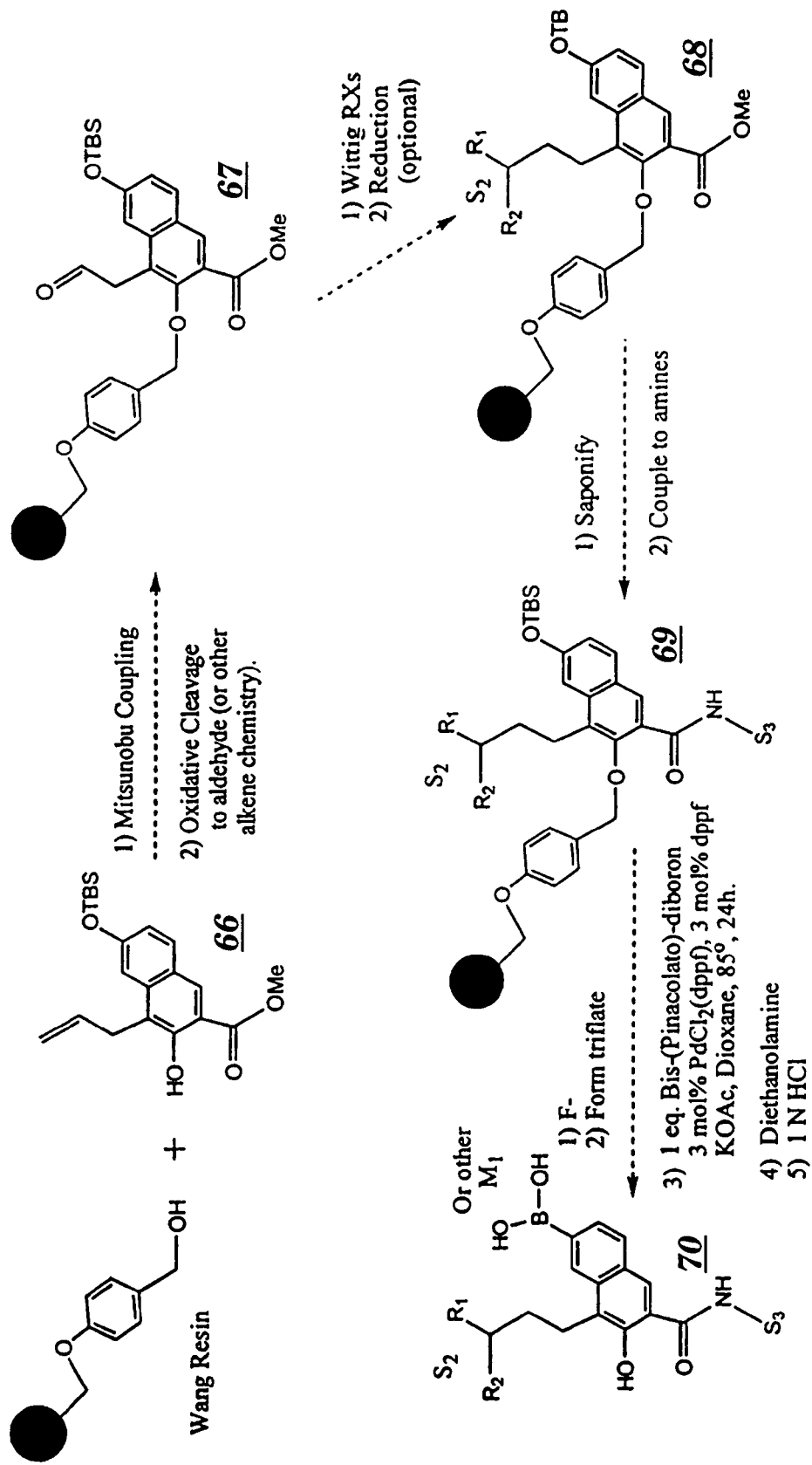
FIG. 11 provides a possible strategy for modifying the naphthalene scaffold in combinatorial libraries.

The naphthalene scaffold currently provides three diversity sites to be explored in the combinatorial libraries, $M_1$, $S_2$ and $S_3$. Solid phase combinatorial chemistry with 96-well plate reactors is similar to that used in previous studies (Pavia et al., 1996). The greatest number and diversity of side chains will be used for $S_3$ followed by $S_2$ and then $M_1$ for the reasons discussed earlier. One possible overall synthetic strategy, based upon the synthetic model studies above, for preparing these libraries is shown in FIG. 11.

Of course if problems arise with this route, there are many other possibilities. For example, if the Mitsunobu coupling to give 67 proceeds in too low a yield (due to the increased steric congestion of the added adjacent allyl group-but perhaps not a problem given the 92% loading obtained in FIG. 10) then the scaffold could be tethered to a resin through the carboxyl group, rather than the OH, using the acylsulfonamide "safety catch" linker (Backes et al., 1996) and form the amides last (the excess amines can be removed after cleavage by filtering through an acidic resin). Likewise, other linkers and/or resins can be used if the reduction of the alkene in the presence of benzylic ethers (67 to 68) is desired but problematic. The first use of the chemistry proposed in FIG. 11 will be to simply prepare a library of 96 amides, containing the boronic acid $M_1$ group, without having the allyl side chain in place so that these two potential complications will not be a problem initially and the most promising $S_3$ elements can be quickly identified.

At least 14 $S_2$ hydrophobic side chains (includes linear, branched and cyclic) are identified for further study (28 side chains, if the corresponding alkenes are also explored) based upon the modeling of candidate side chains into the P–1 site of the src model (FIG. 6) and on the commercial availability of the needed halides to prepare the corresponding Wittig reagents. At least 96 commercially available amines are available which will provide potential $S_3$ specificity elements including: 1) hydrocarbons (4), 2) alkyl groups containing hydrogen bond acceptors (4), 3) alkyl groups containing both hydrogen bond acceptors and donors (19), 4) alkyl/aryl groups containing hydrogen bond acceptors and donors (25), 5) aryl hydrogen bond acceptors and donors (10), 6) heterocyclic hydrogen bond acceptors and donors (20), 7) side chains containing cationic groups (4), 8) side chains containing anionic groups (9), and the 3-amino phenol side chain from inhibitor 43-meta as an internal control for src activity. A broad range of amines were included for $S_3$, in order not to overly bias the library here due to the higher level of uncertainty for this binding site in the src model.

The indole scaffold can be developed into a combinatorial library in much the same fashion. In this case, the indole NH would be used as the tether point for attachment to the Wang (or other) resin since the analogous Minsunobu reaction is known (Bhagwat & Gude, 1994). A large amount of synthetic methodology has been developed for the synthesis of substituted indoles and have designed a route to include the $S_2$ hydrophobic side chain (see FIG. 7) (Ezquerra et al., 1996).

Figure 12:
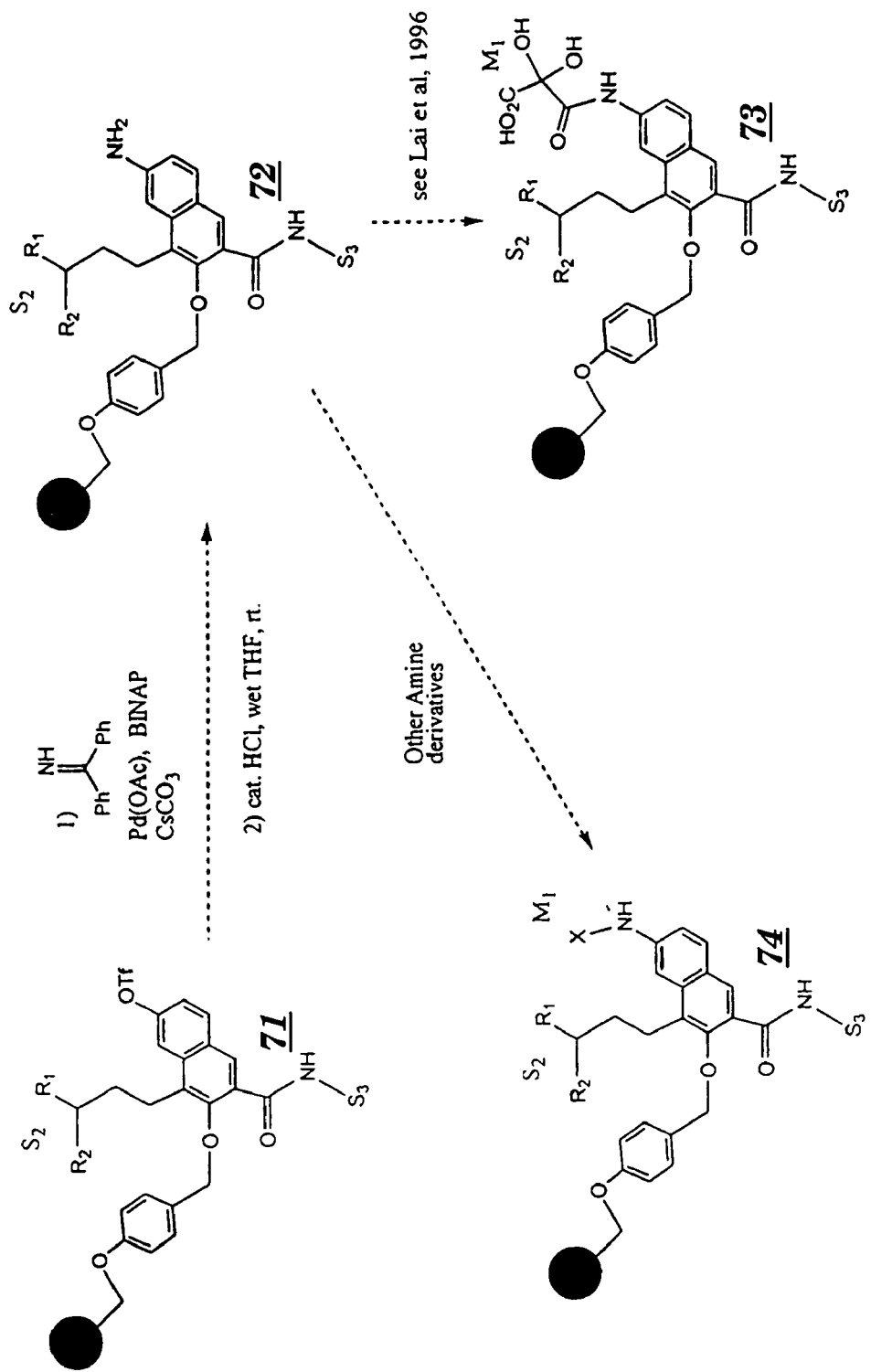
FIG. 12 shows the conversion of the triflate functionality (formed in reaction 2 from intermediate 69 (FIG. 11)) to an amine (Wolfe et al, 1997) followed by conversion to a series of amides or other amine derivatives.

The triflate functionality formed in reaction 2 from intermediate 69 (FIG. 11) can be converted to an amine (Wolfe et al., 1997) and then a series of amides or other amine derivatives following the reaction sequence shown in FIG. 12. In fact, the triflate is a versatile synthetic handle and could be converted into other functional groups as well.

When the amine 72 is available, the known $M_1$ modules (e.g. the sulfamic acid from src inhibitor 28 Table V and amide-acid 17 Table III) can be evaluated with this more developed scaffold and evaluate some new amine derivatives as potential $M_1$ modules. For example the hydrated tricarbonyl amide $M_1$ group shown in structure 73 (and its non-hydrated precursor) is accessible via the synthetic methodology (see Lai et al., 1996) and could form a variety of interesting interactions with the conserved catalytic residues.

Figure 13:
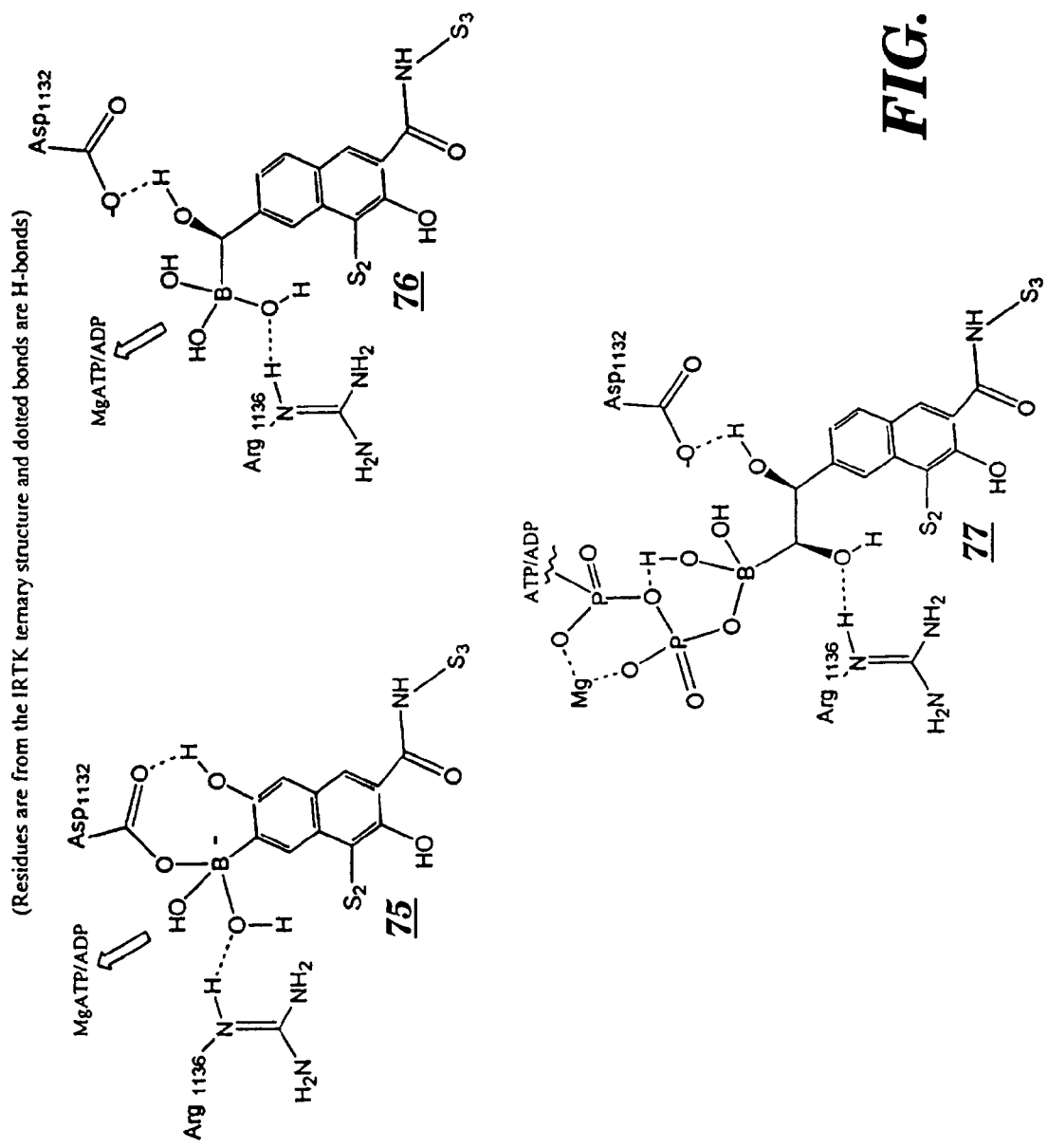
FIG. 13 shows a series of hydroxy-containing analogs with a boronic acid $M_1$ group modeled in the src and IRTK (insulin receptor protein tyrosine kinase) active sites and illustrates possible interactions/binding modes.

Following the modeling procedure described above, a the series of hydroxy-containing analogs of the boronic acid $M_1$ group shown in FIG. 13 were modeled in the src and IRTK active sites and found the illustrated interactions/binding modes as some of the interesting possibilities. Phosphorylation of the boronic acid provides additional interesting possibilities (e.g. suicide type inhibition via reaction of the resulting mixed anhydride with an active site nucleophile). The presence of additional hydroxyl groups on the Tyr-mimetic phenyl ring is necessary and common among many PTK inhibitors (e.g. Piceatannol 52, Table V) and was shown to be beneficial on the side chain with the PKA phosphonate inhibitors (e.g. 2 vs. 3 and 4, Table I). Consequently, adding one or more OH groups to the boronic acid inhibitor $M_1$ design as illustrated in FIG. 13 may considerably enhance potency. These OH groups would also extend the boronic acid side chain past the catalytic Asp and Arg residues without suffering a penalty for covering them with hydrocarbon as was probably the case with the PKA boronic acid homologs (23 and 24, Table III). One possible route to the hydroxyboronic acids 76 and 77 utilizes the chiral boronic ester homologation methodology of Matteson (e.g. see Matteson et al., 1987, 1988, and 1990).

In a preferred embodiment of the invention, the first module is produced by attaching the first module to a peptide scaffold. One or more functional groups are identified which preferentially bind to catalytic residues of the protein kinase. Further, the first module is combined with the second module so that the second module substitutes for the peptide scaffold.

Preferred first modules have a functional group such as boronic acid, a hydroxyl group, phosphonic acid, sulfamic acid, a guanidino group, carboxylic acid, an aldehyde, an amide, and hydroxymethylphosphonic acid. The compounds of the present invention may have two or more functional groups within the first module. More preferred modules are boronic acid groups, a hydroxyl group, or an amide group. An even more preferred amide group is a vicinal tricarbonyl amide.

Preferred second modules include indole, naphthalene, biphenyl, isoquinoline, benzofuran, and benzothiophene. More preferred second modules are an indole or naphthalene. In some embodiments of the invention more than one first module may be bound to the second module. In addition, the first module may have a linear chain comprising between one and three carbon atoms which links the first module to the second module. In alternative embodiments, one of the carbon atoms in the linear chain is substituted with a nitrogen, oxygen, or sulfur atom.

The methods and compounds of the invention are broadly applicable to any protein kinase. Preferred protein kinases are protein tyrosine kinases and protein serine kinases. Preferred protein tyrosine kinases are $pp60^{c-src}$, $p56^{lck}$, ZAP kinase, platelet derived growth factor receptor tyrosine kinase, Bcr-Abl, VEGF (vascular endothelial growth factor) receptor tyrosine kinase, and epidermal growth factor receptor tyrosine kinase, and epidermal growth factor receptor-like tyrosine kinases. A more preferred protein tyrosine kinase is $pp60^{c-src}$. Preferred serine protein kinases include MAP (mitogen activated protein) kinase, protein kinase C, and CDK (cyclin dependent protein kinase).

The method of the present invention may further consist of adding one or more specificity side chain elements to the combination of the first and second modules. Specificity side chains can increase potency and specificity of the inhibitor.

Once a promising second module is identified it is not necessary to repeat all the steps of the method. Rather, the first module, specificity side chains, or a combination of the two may be modified to improve the original inhibitor, i.e. an inhibitor which has an increased ability to inhibit protein kinase activity when compared to the unmodified first inhibitor.

The present method is designed to preferentially provide protein kinase inhibitors which do not act by inhibiting ATP binding to the protein kinase. Inhibitors of protein kinases may be potent but often lack specificity and are therefore often not good drug candidates. Therefore, protein kinase inhibitors which inhibit protein kinase activity but do not inhibit or only weakly inhibit ATP binding to the protein kinase are preferred.

The present invention also provides a method for testing compounds for an ability to inhibit protein kinase activity. Compounds are produced as described above. The activity of the protein kinase is measured in the presence of the inhibitor at the same temperature, pH, ionic strength, osmolarity, and free magnesium concentration as found in a cell which expresses the protein kinase. The level of protein kinase activity is compared to the level of activity from the protein kinase without the presence of the inhibitor. Such an assay system which mimics physiological conditions provides the most relevant inhibition data. The assay may be conducted in an automated assay system. Furthermore, the assay may be combined with a combinatorial chemistry method to rapidly screen numerous candidates.

The Pierce 96-well plate non-radioactive ELISA PTK assay method may be adapted to the Cellular Mimetic assay conditions for initial src screening of the 96-well plate combinatorial libraries. This high throughput assay utilizes the same RR-SRC peptide substrate, except that it is biotinylated so that it can be attached to the NeutrAvidin-coated wells in their commercial 96-well plates. This high throughput inhibition assay can be run by incubating src with the RR-SRC substrate pre-bound to the wells followed by adding their anti-phosphotyrosine antibody (PY20)-horseradish peroxidase (HRP) conjugate and their HRP substrate to quantitate the level of phospho-RR-SRC produced via measuring the level of HRP product with a 96-well plate UV reader. Standard low throughput $P^{32}$-ATP radioactive assays have been used, but a 96-well plate format is preferred, especially with a non-radioactive assay if possible. As very potent src inhibitors are developed, a panel of protein kinase assays could be set up with up to approximately 6 commercially available protein kinases (mostly PTKs), using the Cellular Mimetic protein kinase assay conditions, and test these inhibitors across the panel to obtain an initial assessment of specificity. A more complete specificity assessment, involving the full approximately 2,000 protein kinases, will need to be conducted in cell culture and in vivo through additional collaborations at the appropriate time.

Figure 14:
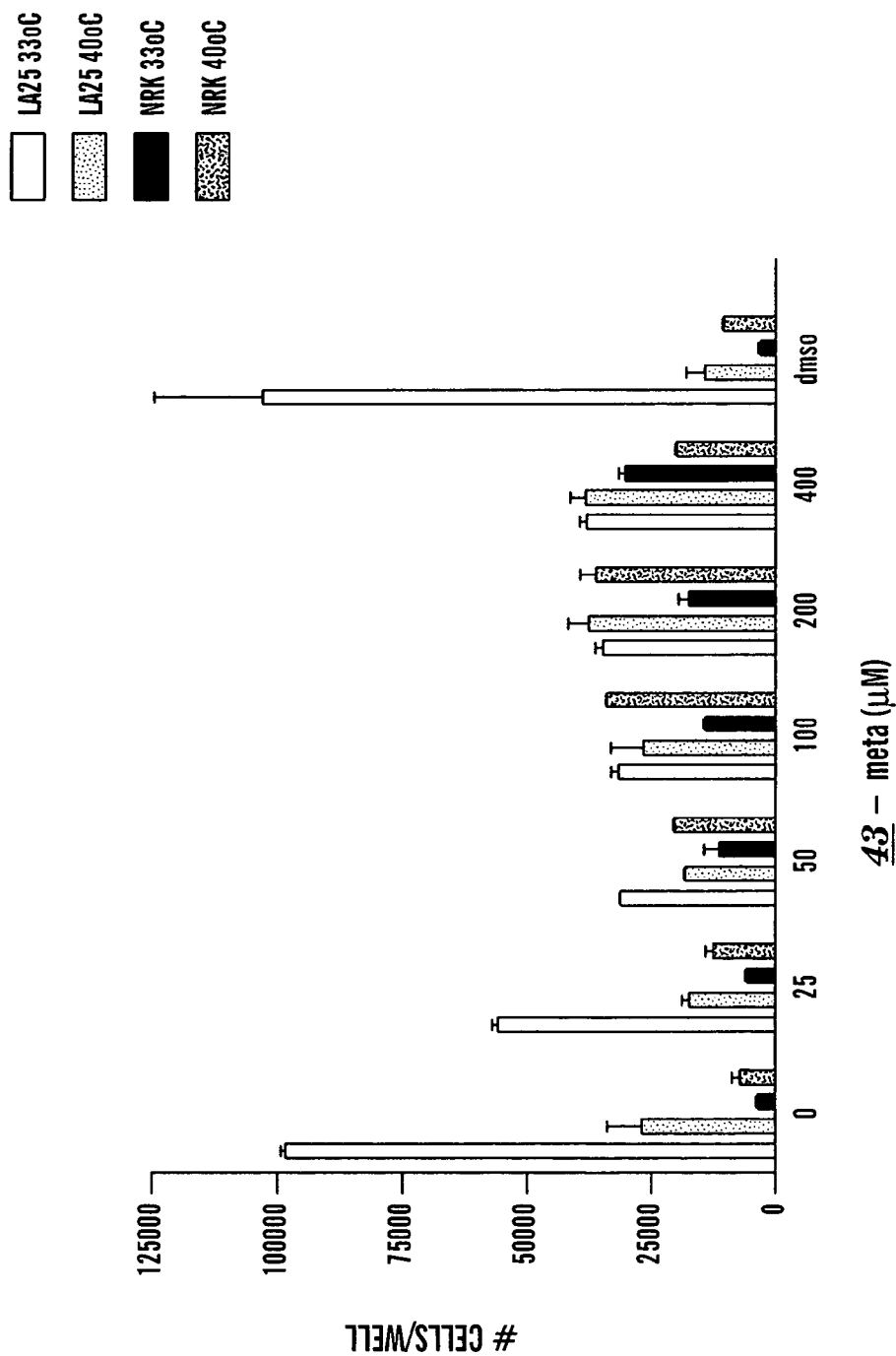
FIG. 14 shows results from testing of the non-peptide src inhibitor 43-meta (Table V) in the LA25 and NRK cell lines.

Active src inhibitors can be studied in a set of side-by-side cell-based assays using normal rat kidney (NRK) cells and a temperature-sensitive $pp60^{v-src}$ transformant of this cell line (LA25). The LA25 transformant engages in anchorage- and serum-independent growth at the "permissive" temperature of 33° C. due to activation of $pp60^{v-src}$ but not at the "non-permissive" temperature of 40° C. at which $pp60^{v-src}$ is not activated (Li et al., 1996). The use of this pair of closely related cell lines for testing the src inhibitors at both the permissive and non-permissive temperatures allows one to determine if a given src inhibitor is blocking cell growth due to specific blockade of the src signaling pathway, by a different mechanism or by a general cytotoxic effect. Results from initial testing of the non-peptide src inhibitor 43-meta (Table V) in this pair of cell lines are shown in FIG. 14.

As shown in this graph the growth of the LA25 cells at the permissive temperature of 33° C. is inhibited by approximately 50% at a 25 μM concentration of 43-meta relative to the LA25 cell growth at the non-permissive 40° C. as a control. The lack of cell toxicity of 43-meta is evidenced by the fact that as its concentration is increased up to 400 μM, the basal growth of the NRK non-transformed cells, the LA25 cells at the non-permissive 40° C. and the LA20 cells at the permissive temperature of 33° C. (but with $pp60^{v-src}$ fully inhibited by 43-meta) not only does not decrease but actually increases somewhat (presumably due to a non-src related activity of this compound). Since the 43-meta solutions were prepared with a low concentration of DMSO for solubilization, a DMSO control was also run at the same concentration. A more complete dose/response curve centered around 25 μM will be run.

In another embodiment, the present invention provides a method of inhibiting a protein kinase. The protein kinase is contacted with a compound having a first module which has a functionality for binding to catalytic residues of the protein kinase and a second module which provides a non-peptide scaffold. The combination of the first and second modules inhibits the protein kinase activity.

A preferred non-peptide protein tyrosine kinase inhibitor provided by the present invention has the following formula I:

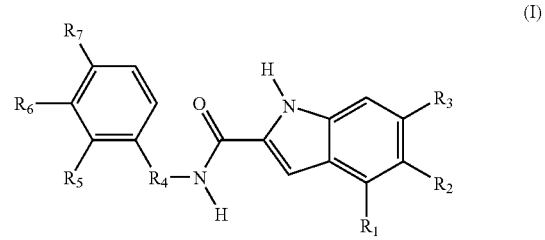

wherein $R_1$ is H or OH, $R_2$ is H or OH, $R_3$ is OH or H, and $R_4$ is $CH_2$, $CH(CH_3)$(R-configuration), or $CH(CH_3)$(S-configuration), $R_5$ is $OCH_3$, H, or OH, $R_6$ is $OCH_3$, F, H, or OH, and $R_7$ is $OCH_3$, H, OH, $CO_2H$, $CO_2CH_3$, $CH_2CO_2H$, or $CH_2CO_2CH_3$. In a more preferred embodiment, the non-peptide protein tyrosine kinase inhibitor inhibits the activity of $pp60^{c-src}$ tyrosine kinase.

Another preferred non-peptide protein tyrosine kinase inhibitor has the following formula II:

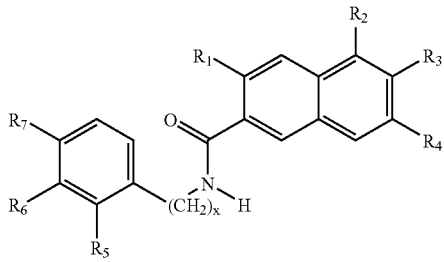

where $R_1$ is OH or H, $R_2$ is OH or H, $R_3$ is OH or H, $R_4$ is OH or H, $R_5$ is OH, OMe, or H, $R_6$ is OH, OMe, or H, $R_7$ is OH, OMe, or H, and X is 0 or 1. In a more preferred embodiment, the non-peptide protein tyrosine kinase inhibitor has the above structure and $R_1$ is OH, $R_2$ is OH, $R_3$ is H, $R_4$ is H, $R_5$ is OMe, $R_6$ is H, $R_7$ is H, and X is 1.

The present invention further provides a method of treating a condition, responsive to a protein kinase inhibitor, in a patient. An effective dose of a protein kinase inhibitor is administered to a patient. The protein kinase inhibitor has a first module having a functionality for binding to catalytic residues of the protein kinase and a second module which provides a non-peptide scaffold, where the combination of the first and second modules inhibits protein kinase activity.

Finally, promising src inhibitors can be screened in primary human tumor tissue assays, particularly to look for synergy with other known anti-cancer drugs.

EXAMPLES

Example 1

Design, Synthesis and Activity of Non-ATP Competitive Hydroxynaphthalene Derivative Inhibitors of pp60$^{c\text{-}Src}$ Tyrosine Kinase The crystal structure of the autoinhibited human IRTK catalytic domain (Hubbard et al., 1994) was used to carry out qualitative molecular modeling studies (SYBYL™, 6.4, Tripos Inc., St. Louis) wherein a naphthalene ring was superimposed upon the IRTK Tyr 1,162. The IRTK region containing Tyr 1,162 folds back into the active site, with Tyr 1,162 positioned analogous to a phosphorylated Tyr in a peptide substrate, thereby autoinhibiting the tyrosine kinase. This superimposition indicated that an amide carbonyl should be placed at the 2-position (Scheme 1) of the Scheme 1

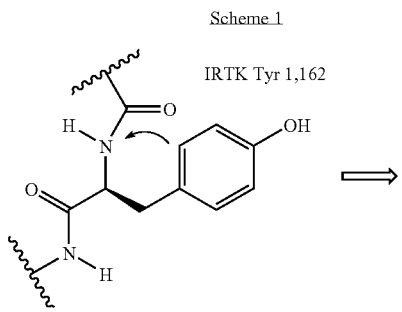

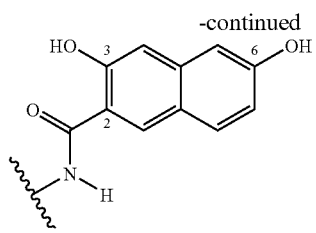

naphthalene ring to mimic the Tyr 1,162 carbonyl and a hydroxyl group should be positioned at the 6-position to mimic the Tyr 1,162 hydroxyl group. These modeling studies also indicated that a hydroxyl group at the 3-position could mimic the Tyr 1,162 NH.

In order to test these design concepts experimentally, the 2-position carbonyl group was appended as either a methyl ester or as a series of amides (Table VI). The hydroxy N-phenyl (X=0) and N-benzyl (X=1) amides were chosen based upon the increase in pp60$^{c\text{-}src}$ inhibitor potency observed with iminochromene analogs containing appended hydroxy N-phenyl amide side-chains (Huang et al., 1995). Analogs where the 6-hydroxyl group was either deleted or moved were also prepared to determine if a drop in potency occurs as predicted from the modeling studies.

The series of 2-carbonyl-3,5-dihydroxy naphthalene inhibitors (1a, 2a-2d, 2i-2l, 2o-2p) and 2-carbonyl-3,7-dihydroxy naphthalene inhibitors (1c, 2t-2u) were synthesized from commercially available (Aldrich) 3,5-dihydroxy-2-naphthoic acid and 3,7-dihydroxy-2-naphthoic acid, respectively. The methyl esters 1a and 1c were obtained by refluxing the respective acid starting materials for 48 h in methanol pre-saturated with HCl gas. The amides (2a-2d, 2i-2l, 2o-2p, 2t-2u) were synthesized by coupling the respective carboxylic acid with commercially available (Aldrich or Lancaster) amines using one of two methods. The first method utilized the NBS/PPh$_3$ methodology as described by Froyen (Froyen, 1997). The second method utilized IIDQ (Aldrich) as the coupling reagent. The carboxylic acid was first reacted with 1.0 eq. IIDQ in anhydrous DMF at room temperature for 24 h. The respective amine (2.0 eq.) was then added neat and the reaction was heated to 80° C. for 2-6 hours. After aqueous workup, purification was achieved by silica gel chromatography and precipitation from CH$_2$Cl$_2$/hexane, followed by preparative C-18 RP-HPLC (CH$_3$CN/H$_2$O), if necessary. The benzyl amines were commercially available only as their corresponding hydroxyl protected methyl ethers. Consequently, after amide formation, the hydroxyl groups were deprotected by treatment with 6 eq. BBr$_3$ in DCM for 1 minute at −78° C. followed by 1 hour at room temperature.

TABLE VI pp60$^{c\text{-}src}$ inhibitory activity of hydroxynaphthalene derivatives and select published inhibitors.[a,b,c]

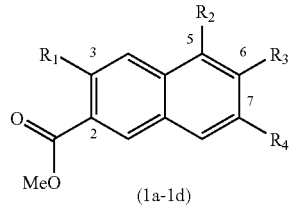

(1a-1d)

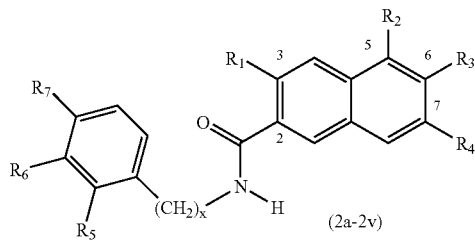

(2a-2v)

| Compd | R1 | R2 | R3 | R4 | R5 | R6 | R7 | X | % Inhibition at 100 μM (std. dev.) | IC50 (μM) |
|---|---|---|---|---|---|---|---|---|---|---|
| 1a | OH | OH | H | H | N/A | N/A | N/A | N/A | 5 (+/−2) | n.t. |
| 1b | OH | H | OH | H | N/A | N/A | N/A | N/A | 47 (+/−3) | n.t. |
| 1c | OH | H | H | OH | N/A | N/A | N/A | N/A | 19 (+/−6) | n.t. |
| 1d | NH$_2$ | H | H | H | N/A | N/A | N/A | N/A | inactive | n.t. |
| 2a | OH | OH | H | H | OH | H | H | 0 | 12 (+/−4) | n.t. |
| 2b | OH | OH | H | H | H | OH | H | 0 | 51 (+/−1) | 150 |
| 2c | OH | OH | H | H | H | H | OH | 0 | 60 (+/−7) | n.t. |
| 2d | OH | OH | H | H | OH | H | OH | 0 | 14 (+/−2) | n.t. |
| 2e | OH | H | OH | H | OH | H | H | 0 | 39 (+/−5) | n.t. |
| 2f | OH | H | OH | H | H | OH | H | 0 | 89 (+/−1) | 16 |
| 2g | OH | H | OH | H | H | H | OH | 0 | 23 (+/−5) | n.t. |
| 2h | OH | H | OH | H | OH | H | OH | 0 | 56 (+/−1) | n.t. |
| 2i | OH | OH | H | H | H | OMe | H | 0 | 33 (+/−5) | n.t. |
| 2j | OH | OH | H | H | H | H | OMe | 0 | 35 (+/−8) | n.t. |
| 2k | OH | OH | H | H | OMe | H | H | 1 | 13 (+/−3) | n.t. |
| 2l | OH | OH | H | H | H | H | OMe | 1 | 14 (+/−2) | n.t. |
| 2m | OH | H | OH | H | OMe | H | H | 1 | inactive | n.t. |
| 2n | OH | H | OH | H | H | H | OMe | 1 | 4 (+/−7) | n.t. |
| 2o | OH | OH | H | H | OH | H | H | 1 | 41 (+/−2) | n.t. |
| 2p | OH | OH | H | H | H | H | OH | 1 | 49 (+/−4) | n.t. |
| 2q | OH | H | OH | H | OH | H | H | 1 | 42 (+/−2) | n.t. |
| 2r | OH | H | OH | H | H | OH | H | 1 | 55 (+/−3) | n.t. |
| 2s | OH | H | OH | H | H | H | OH | 1 | 42 (+/−3) | n.t. |
| 2t | OH | H | H | OH | H | OH | H | 0 | 68 (+/−5) | n.t. |
| 2u | OH | H | H | OH | H | OH | H | 1 | 40 (+/−3) | n.t. |
| 2v | H | H | OH | H | H | OH | H | 0 | 45 (+/−5) | n.t. |
| Iminochromene 9TA | | | | | | | | | 30 (+/−15) | Lit[8]: 0.118 |
| Piceatannol | | | | | | | | | 41 (+/−2) | Lit[13]: 66 (lck) |
| ST-638 | | | | | | | | | 37 (+/−5) | Lit[14]: 18 |
| Emodin[d] | | | | | | | | | 22 (+/−3) | Lit[15]: 38 |
| Tyrophostin A47 | | | | | | | | | 43 (+/−3) | |

Table VI Footnotes:

[a] The previously described assay procedure (Lai et al., 1998) was used with the following assay components, final concentrations and conditions: 50.0 mM MOPS, 4.02 mM MgCl$_2$, 6.00 mM K$_3$citrate (used as a Mg$^{2+}$ buffer to stabilize the free Mg$^{2+}$ at 0.5 mM), 99.0 mM KCl, 10.0 mM 2-mercaptoethanol, 198 μM ATP, 19.8 μM ADP, 10 U full length human purified recombinant pp60$^{c\text{-}src}$ (Upstate BiotechnologyInc.), 2.00 mM RR-SRC, 4.0% DMSO, pH 7.2, 37° C. These overall assay conditions have been shown (Choi, 1999) to reproduce the intracellular conditions of pH, temp., free Mg$^{2+}$ (0.5 mM), ionic strength, osmolality, ATP/ADP and reduction potential.

[b] All new compounds were characterized by proton NMR, EI or FAB(+) MS and are pure by TLC.

[c] N/A = Not applicable, n.t. = Not tested.

[d] ATP-competitive.

The series of 2-carbonyl, 3,6-dihydroxy naphthalene inhibitors (1b, 2e-2h,

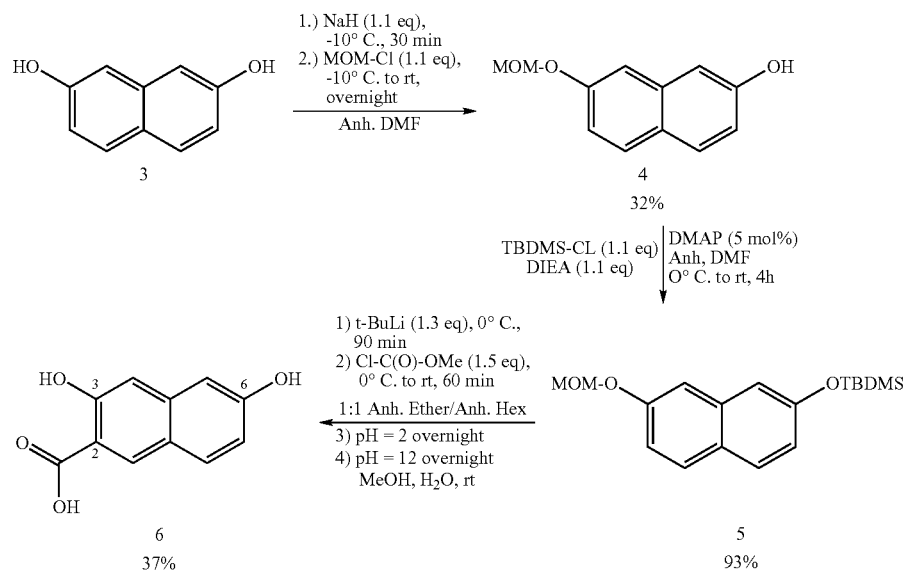

2m-2n, 2q-2s) were synthesized from 3,6-dihydroxy-2-naphthoic acid 6 using the methods described above. The synthesis of intermediate 6 that was developed is shown in Scheme 2 beginning with commercially available 2,7-dihydroxynaphthalene 3 (Aldrich).

Compound 1d was synthesized from 3-amino-2-naphthoic acid (Aldrich) by reaction with TMS-diazomethane in DCM at room temperature. Compound 2v was synthesized from 6-hydroxy-2-naphthoic acid (Aldrich) using the amidation method described by Froyen (Froyen, 1997).

Kinase assay conditions have been shown to influence the measured inhibitory activity (Lawrence et al., 1998). Consequently, in order to accurately determine the relative potency of the newly designed class of pp60$^{c-src}$ inhibitors, the inhibitory activity of four previously published, non-ATP competitive PTK inhibitors, was also tested. Piceatannol, ST-638, and Tyrphostin A47 were chosen because they are commercially available (Sigma or Calbiochem) and are representative of the spectrum of known non-ATP competitive PTK inhibitors. Emodin (Calbiochem) is ATP-competitive when analyzed with the tyrosine kinase p56$^{lck}$. Previously, iminochromene 9TA was the most potent non-ATP competitive pp60$^{c-src}$ inhibitor reported (Huang et al., 1995). Since iminochromene 9TA was not commercially available, it was synthesized using a novel route by converting 3-aminophenol to the corresponding TBDMS ether (1.1 eq. TBDMS-Cl, 1.1 eq. DIEA, 5 mol % DMAP, DMF, 24 h, rt, 71%). The resulting aniline was coupled using 2.0 eq. of cyanoacetic acid (1.1 eq. EDCI, 1.1 eq. TEA, DMF, 18 h, 75° C., 70%). Condensation of the resulting amide with 1.2 eq. of 2,3-dihydroxybenzaldehyde (cat. piperidine, abs. EtOH, 2 h, 60° C.) followed by deprotection (1.1 eq. TBAF, THF, 15 m, 43% overall) gave iminochromene 9TA with satisfactory elemental, FAB(+)MS and $^1$H NMR analysis after purification by flash chromatography (10:1, DCM:MeOH).

The inhibitory activities shown in Table VI for compounds 1a-d and 2a-2v were determined using purified, full length, human recombinant pp60$^{c-src}$. Due to the number of compounds tested, and the associated cost, their rank order potencies were first determined at a constant inhibitor concentration (100 μM). As predicted by the modeling studies, based upon analogy to the IRTK Tyr 1,162 hydroxyl group, a preference for positioning the naphthalene hydroxyl group on carbon 6 vs. 5 or 7 was observed in both the ester (1b, 47% vs. 1a, 5% & 1c, 19%) and amide (e.g. 2f, 89% vs. 2b, 51% & 2t, 68%) series. The prediction that attaching a hydroxyl group at naphthalene carbon 3 (mimicking the Tyr 1,162 NH) would improve potency was also confirmed (2f, 89% vs. 2v, 45%). Finally, the prediction that extending the inhibitor as an amide at the 2-position (mimicking the peptide bond) could further improve potency was confirmed as well (e.g. 2f, 89% vs. 1b, 47%).

The data provided in Table VI demonstrate that moving the hydroxyl group from the optimal 6-position to the adjacent naphthalene carbon 5 results in a different structure activity profile with regard to the optimal concurrent positioning of the hydroxyl group(s) in the amide side chain (e.g. 2f/2g vs. 2b/2c). Also of note is the replacement of the amide side chain hydroxyl group with a corresponding methoxy group in compounds 2i-2n. In the case of the N-phenyl amides (2i-2j), their activity, relative to the corresponding hydroxy amides (2b-2c), was not reduced as significantly as in the case of the N-benzyl amides (2k-2n vs. 2o-2q, 2s). This suggests that in the benzyl derivatives, the amide side chain hydroxyl groups either interact with the enzyme as hydrogen bond donors, or the methoxy groups are too large to fit in the binding site.

A more quantitative analysis of the selectivity for positioning a hydroxyl group on carbon 6 vs. 5 is provided by comparing the IC$_{50}$ values of 2f (16 μM) vs. 2b (150 μM), respectively. These results also confirm that a drop in % inhibition from approximately 90% to approximately 50% represents an order of magnitude difference in potency, as expected. Similarly, a drop in % inhibition from approximately 50% to 10% would represent another order of magnitude difference in potency.

A direct comparison of the most potent inhibitor from this series, compound 2f, with the five previously reported PTK inhibitors shown in Table VI demonstrates that, under these assay conditions, 2f is more potent by one to two orders of magnitude. Interestingly, iminochromene 9TA was previously reported (Huang et al., 1995) to have an $IC_{50}$ of 118 nM against $pp60^{c\text{-}src}$ and was the most potent known non-ATP competitive $pp60^{c\text{-}src}$ inhibitor, but under the current assay conditions only a 30% inhibition at 100 μM was observed. These results re-emphasize (Lawrence et al., 1998) the importance of comparing protein kinase inhibitors under identical assay conditions.

A goal of these studies was to obtain non-peptide $pp60^{c\text{-}src}$ inhibitors which do not compete with ATP. Consequently the % inhibition of $pp60^{c\text{-}src}$ by 2f and 2b at constant inhibitor concentrations was monitored as a function of increasing [ATP] up to a cellular mimetic 1 mM level. Since the [ATP] had little effect on the % inhibition, both 2f and 2b are non-competitive inhibitors with respect to ATP. The % inhibition was measured using ATP concentrations of 200, 500 and 1,000 μM while holding the inhibitor concentration constant. If the inhibitor is directly competing with ATP, then this 5-fold overall increase in [ATP] is equivalent to decreasing the inhibitor concentration 5-fold in terms of the effect on % inhibition. Consequently, the % inhibition should decrease to the value observed in the $IC_{50}$ dose-response curve (obtained with 200 μM ATP) for 1/5 of the set inhibitor concentration used in this experiment if direct competition with ATP is occurring. For inhibitor 2f (set at 25 μM) a 62% (±5), 54% (±3) and 50% (±1) inhibition at 200 μM, 500 μM and 1,000 μM ATP, respectively, was obtained whereas the level of inhibition should have dropped to approximately 20% at 1,000 μM ATP if direct competition with ATP were occurring. Similarly, for inhibitor 2b (set at 300 μM) an 84% (±1), 81% (±1) and 77% (≅2) inhibition at 200 μM, 500 μM and 1,000 μM ATP, respectively, was obtained. The high cost of many kinases has stimulated other researchers to monitor inhibitor potency as a function of increasing [ATP] for the same purpose (Saperstein et al., 1989; Burke et al., 1993; Davis et al., 1989; Davis et al., 1992; Faltynek et al., 1995; and Sawutz et al., 1996).

In summary, structure-based design has produced a series of hydroxynaphthalene $pp60^{c\text{-}src}$ non-peptide inhibitors that do not compete with ATP. An extension of these design concepts from the naphthalene scaffold to an indole scaffold is reported in the following Example.

Example 2

Design, Synthesis and Activity of Non-ATP Competitive Hydroxyindole Derivative Inhibitors of $pp60^{c\text{-}Src}$ Tyrosine Kinase In the preceding example, the structure-based design of a series of $pp60^{c\text{-}src}$ inhibitors utilizing a naphthalene scaffold is described. These compounds were designed to bind in the peptide substrate site because of the potential for greater selectivity and efficacy in a cellular environment relative to the alternative ATP

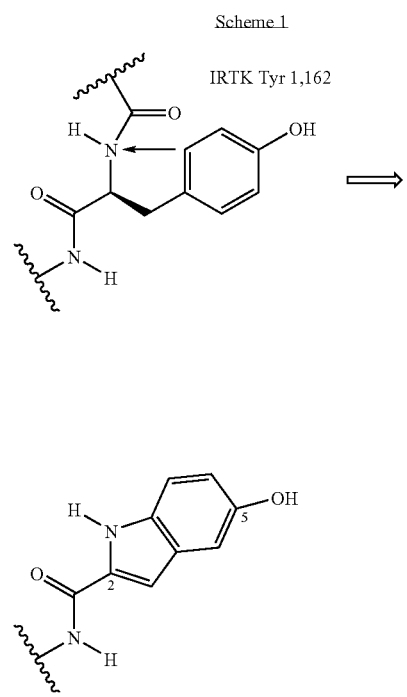

Scheme 1 substrate site. This example presents an extension of these design concepts to a series of $pp60^{c\text{-}src}$ inhibitors based upon an indole scaffold. Once again the crystal structure of the autoinhibited insulin receptor PTK (IRTK) was used to carry out qualitative molecular modeling studies, except in this case an indole ring was superimposed upon the IRTK Tyr 1,162. This superimposition indicated that the indole NH can mimic the Tyr 1,162 NH, a carbonyl should be placed at the 2-position, and a hydroxyl group should be placed at the 5 position to mimic the Tyr 1,162 carbonyl and OH, respectively (Scheme 1). The conceptual cyclization of Tyr 1,162 to the smaller 5-membered ring of an indole illustrated in Scheme 1, relative to a 6-membered ring in the case of the naphthalene scaffold (Karni et al., 1999), results in a movement of the optimal positioning of the OH from carbon 6 in the naphthalene scaffold to carbon 5 in the indole scaffold.

The indole amide derivatives containing hydroxy phenyl/benzyl side chains 2d-f, 2j-l (Table VII), respectively, were selected based upon the increase in $pp60^{c\text{-}src}$ inhibitor potency observed for the analogous naphthalene-based hydroxy phenyl amides reported in the previous example. The corresponding methyl ethers 2a-c,g-i,v are precursors in the synthesis. The additional analogs shown in Table VII were prepared to begin expanding the range of side chains beyond the hydroxy/methoxy groups that have now been extensively probed with both the indole and naphthalene scaffolds.

The indole amides containing only hydroxy or methoxy side chains were synthesized as illustrated:

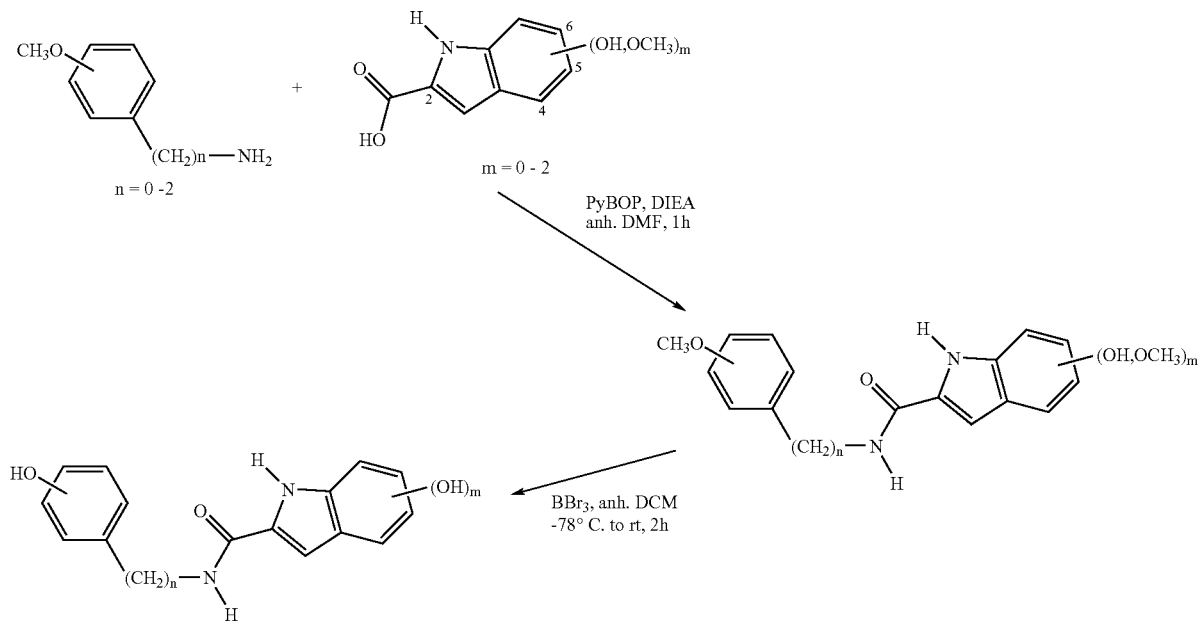

Scheme 2

The 2-indolecarboxylic acid derivative, the methoxyphenyl amine (1.1 eq, Aldrich, Lancaster or Fluka), and the coupling reagent PyBOP (benzotriazol-1-yloxy)tripyrrolidino-phosphonium-hexafluorophosphate) (1 eq, Fluka) were dissolved in anhydrous DMF. The solution was cooled to 0° C. under argon and then diisopropylethylamine (DIEA, 3 eq) was added. The reaction was stirred at 0° C. for 1 min followed by 1 hour at room temperature. After workup the residue was purified by silica gel chromatography.

The methyl ethers were cleaved with boron tribromide (1 M in DCM, Aldrich) when desired. The indole amide methyl ether was suspended in dry DCM and cooled to −78° C. under argon. One equivalent of $BBr_3$ was added for each heteroatom in the starting material plus one excess equivalent. The resulting dark red solution was stirred at −78° C. for 30 min and then at room temperature for 1-2 hours. The reaction was quenched with water (10 min) before workup.

TABLE VII pp60[c-src] inhibitory activity of hydroxyindole derivatives.[a,b,c]

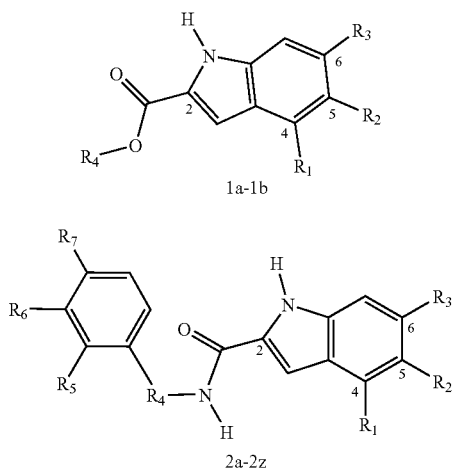

| Compd | R1 | R2 | R3 | R4 | R5 | R6 | R7 | % Inhibition at 100 μM (std. dev.) |
|---|---|---|---|---|---|---|---|---|
| 1a | H | OH | H | $CH_3$ | N/A | N/A | N/A | 40 (+/−5) [at 500 μM] |

TABLE VII-continued pp60[c-src] inhibitory activity of hydroxyindole derivatives.[a,b,c]

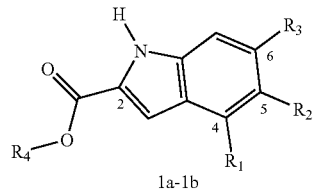

1a-1b

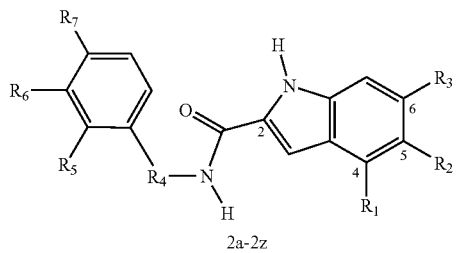

2a-2z

| Compd | R1 | R2 | R3 | R4 | R5 | R6 | R7 | % Inhibition at 100 μM (std. dev.) |
|---|---|---|---|---|---|---|---|---|
| 1b | H | OH | OH | CH$_2$CH$_3$ | N/A | N/A | N/A | 28 (+/−3) |
| 2a | H | OH | H | — | OCH$_3$ | H | H | 3 (+/−1) |
| 2b | H | OH | H | — | H | OCH$_3$ | H | 21 (+/−2) |
| 2c | H | OH | H | — | H | H | OCH$_3$ | 39 (+/−9) |
| 2d | H | OH | H | — | OH | H | H | 43 (+/−1) |
| 2e | H | OH | H | — | H | OH | H | 30 (+/−6) |
| 2f | H | OH | H | — | H | H | OH | 45 (+/−3) |
| 2g | H | OH | H | CH$_2$ | OCH$_3$ | H | H | 21 (+/−5) |
| 2h | H | OH | H | CH$_2$ | H | OCH$_3$ | H | 7 (+/−6) |
| 2i | H | OH | H | CH$_2$ | H | H | OCH$_3$ | 18 (+/−4) |
| 2j | H | OH | H | CH$_2$ | OH | H | H | 24 (+/−3) |
| 2k | H | OH | H | CH$_2$ | H | OH | H | 74 (+/−2) [IC$_{50}$ = 38 μM] |
| 2l | H | OH | H | CH$_2$ | H | H | OH | 54 (+/−2) |
| 2m | H | OH | H | CH$_2$CH$_2$ | H | H | OH | 21 (+/−7) |
| 2n | H | OH | H | CH$_2$ | H | H | CO$_2$H | not active |
| 2o | H | OH | H | CH$_2$ | H | H | CO$_2$CH$_3$ | 11 (+/−4) |
| 2p | H | OH | H | — | H | H | CH$_2$CO$_2$H | 7 (+/−6) |
| 2q | H | OH | H | — | H | H | CH$_2$CO$_2$CH$_3$ | 32 (+/−7) |
| 2r | H | OH | H | — | H | F | H | 21 (+/−2) |
| 2s | H | OH | H | CH$_2$ | H | F | H | 57 (+/−6) |
| 2t | H | OH | OH | CH$_2$ | H | OH | H | 26 (+/−2) |
| 2u | H | H | OH | CH$_2$ | H | OH | H | 56 (+/−6) |
| 2v | H | H | H | CH$_2$ | H | H | OCH$_3$ | 4 (+/−4) |
| 2w | H | H | H | CH$_2$ | H | H | OH | 36 (+/−4) |
| 2x | OH | H | H | CH$_2$ | H | OH | H | 60 (+/−3) |
| 2y | H | OH | H | CH(CH$_3$)R | H | OH | H | 15 (+/−3) |
| 2z | H | OH | H | CH(CH$_3$)S | H | OH | H | 13 (+/−7) |

[a] All compounds were tested as described in the preceding Example.
[b] All compounds were characterized by proton NMR, FAB(+) MS and are pure by TLC.
[c] N/A = Not applicable.

Using this synthetic route, the series of 5-hydroxyindole amide inhibitors 2a-m,y,z were prepared from 5-hydroxy-2-indolecarboxylic acid. The 4- and 6-hydroxyindole amides (2x,u, respectively) were synthesized from methyl 4-methoxy-2-indolecarboxylate and methyl 6-methoxy-2-indolecarboxylate, respectively. The 5,6-dihydroxyindole amide 2t was prepared from ethyl 5,6-dimethoxyindole-2-carboxylate. Sonication of the esters in 1 N NaOH for 1 h provided the corresponding carboxylic acids for coupling. The des-hydroxy indole amides 2v,w were synthesized from indole-2-carboxylic acid. All of the indole starting materials were commercially available (Aldrich or Lancaster).

The fluoro inhibitors 2r,s were likewise prepared from the corresponding fluorophenyl amines (Aldrich). The inhibitors containing esters or carboxylic acids on the amide side chain, 2n-q, were prepared from the corresponding amino carboxylic acids (Aldrich). The side chain carboxylic acid was first protected as a methyl ester (anh. MeOH pre-saturated with HCl, reflux, 1d), followed by PyBOP coupling (as above), then saponification back to the carboxylic acid when desired.

The methyl ester 1a was prepared by refluxing a solution of the carboxylic acid overnight in anhydrous methanol pre-saturated with HCl gas. The ethyl ester 1b was prepared by BBr$_3$ deprotection of ethyl 5,6-dimethoxyindole-2-carboxylate as above. All of the inhibitors listed in Table VII were purified by silica gel chromatography.

As in Marsilje 2000, the rank order activity of this series of pp60[c-src] inhibitors was first determined at a constant inhibitor concentration (Table VII). The same inhibitor concentration (100 μM) was used for the current indole series of inhibitors, the previous naphthalene series of inhibitors, and five non-ATP competitive literature PTK inhibitors. This allowed an efficient rank order comparison of 59 compounds in total under identical assay conditions.

The modeling studies predicted that a hydroxy group at carbon 5 of the indole scaffold would be optimal. Comparison of the 5-hydroxy indole inhibitor 2k (74%) with the analogous 6-hydroxy indole inhibitor 2u (56%) and 4-hydroxy indole inhibitor 2x (60%) confirms this prediction, although the preference is not strong. The prediction that a hydroxy group at carbon 5 will improve the activity (relative to no hydroxy group) is confirmed by comparing the 5-hydroxy indole inhibitor 2l (54%) with the corresponding des-hydroxy inhibitor 2w (36%).

Extending the indole inhibitors as aryl amides at carbon 2 improved potency, as expected based upon the previous naphthalene inhibitors. For example, the meta-hydroxybenzyl amide indole 2k gives 74% inhibition at 100 μM whereas the analogous methyl ester 1a gives only 40% inhibition at 500 μM. Interestingly, comparing the 5,6-dihydroxy ethyl ester 1b (28%) to the corresponding aryl amide 2t (26%) shows that the simultaneous presence of the second hydroxy at carbon 6 prevents the potency enhancement normally provided by the otherwise preferred meta-hydroxybenzyl amide side chain. This amide side chain was the best of the current series when the 5-hydroxyl group is present alone (2k, 74%) and still gave good inhibition when a 6-hydroxy group was present alone (2u, 56%). Also, the simultaneous presence of two hydroxy groups at carbons 5 and 6 seems well tolerated in the absence of an amide side chain (1b vs. 1a and 2e). This data suggests that a change in the binding orientation of the indole scaffold may have occurred due to the presence of the second hydroxy group and that a different amide side chain may now be preferred. The optimal combination of side chains at carbons 4-7 (including functional group replacements for hydroxy groups (Lai et al., 1999)) and amide side chains is currently under investigation.

In general, the indole scaffold structure-activity-relationships ("SARs") revealed by the data in Table VII parallels that reported in the preceding paper for the naphthalene scaffold. In both cases positioning a hydroxy group on the scaffold analogous to the Tyr 1,162 OH, as identified by modeling studies, provided the highest potency. Moving this hydroxy group to one of the adjacent carbons reduced the potency, but not dramatically, in both cases. Extending both scaffolds with aryl amides at the position identified by the modeling studies to mimic the Tyr 1,162 peptide bond improved the potency. With both scaffolds, substitution of a methoxy group for the hydroxy groups on the amide side chain usually reduced potency, and did so to a greater extent with the longer benzylamide side chain (e.g. 2k, 74% vs. 2h, 7% compared to 2e, 30% vs. 2b, 21%). The major difference in the SARs for these two scaffolds is that the 5-hydroxyindole scaffold prefers the longer m-hydroxybenzyl amide side chain (2k, 74% vs. 2e, 30%) whereas the analogous 3,6-dihydroxynaphthalene scaffold prefers the shorter amide side chain derived from m-hydroxyaniline. The 5-hydroxyindole scaffold showed essentially no preference for the position of the hydroxyl group on the shorter amide side chain (2d-f) whereas with the longer hydroxybenzyl amide side chain a significant preference for the meta position was observed (2j-l). In the case of the 3,6-dihydroxynaphthalene scaffold the opposite was observed.

Additional molecular modeling studies were carried out to further probe the preference for a longer amide side chain with the indole scaffold. The most active naphthalene inhibitor 3 from the previous report was used as a template upon which the analogous indole inhibitor 2e and the homologated indole inhibitor 2k were superimposed. The three most important side chain functional groups in naphthalene inhibitor 3 are considered to be the 6-hydroxy group (hydrogen-bond donor and

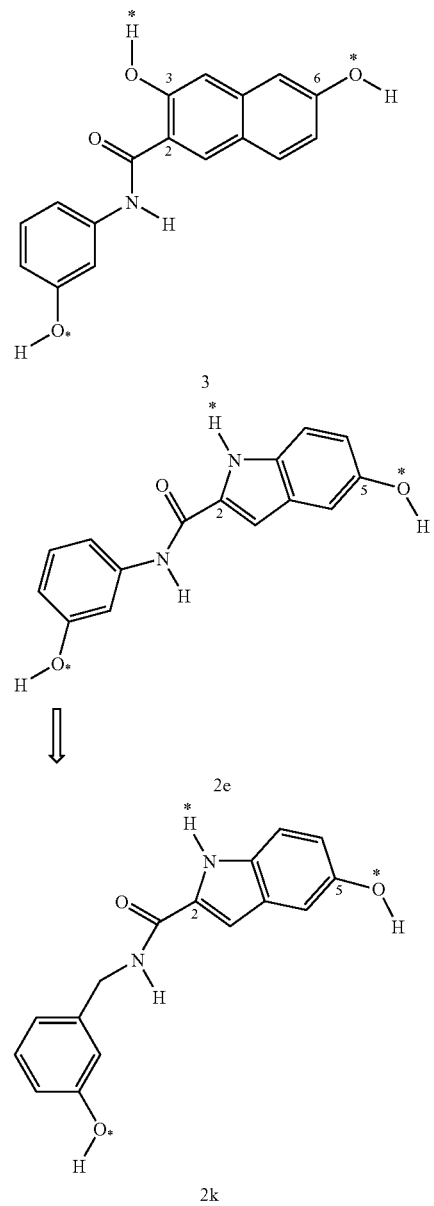

acceptor), the hydrogen from the 3-hydroxy group (hydrogen-bond donor), and the side chain hydroxy group (hydrogen-bond acceptor) based upon the rational design and SAR for both series of inhibitors. This three point pharmacophore model is identified in both series by asterisks in Scheme 3.

The "multifit", energy minimization and "fit atoms" facilities within SYBYL™ (6.4, Tripos, St. Louis) were used in sequence to superimpose 2e and 2k onto 3. This overall fitting process was carried out with spring constants (multifit) and weights (fit atoms) chosen such that the highest emphasis was on optimally superimposing the scaffold pharmacophore oxygen and hydrogen atoms (100), followed by the side chain oxygen atoms (10) and then the intervening amide bond (1). The "multifit" process adjusted the conformations for maximum pharmacophore fit, the subsequent minimization produced the nearest local minimum energy conformations and finally the "fit atoms" process produced the best pharmacophore superimposition of these minimized conformations. As expected, the scaffold pharmacophore oxygen and hydrogen atoms of both 2e and 2k superimposed closely and similarly upon the corresponding atoms in 3 (all within approximately 0.50 A°). However, the side chain pharmacophore oxygen atoms of 2e and 2k differed significantly in their superimposition on the corresponding oxygen atom of 3, with displacements of 1.8 A° vs. only 0.08 A° respectively. This close fit of the three key pharmacophore sites between 2k and 3 provides a rationalization for their potency differing by only a factor of 2.4 ($IC_{50}$ values of 38 μM vs. 16 μM, respectively).

Extending the amide side chain by another carbon atom reduced the activity (2m, 21% vs. 2l, 54%). Adding a methyl group to the benzylic carbon of 2k, in either stereochemistry, greatly reduced the activity (2y, 15% & 2z, 13% vs. 2k, 74%). Replacing the side chain hydroxy group (in the para position) with a carboxylate anion (2n, 0% vs. 2l, 54% and 2p, 7% vs. 2f, 45%) reduced the activity, whereas the corresponding methyl esters (2o, 11% & 2q, 32%, respectively) showed a smaller loss of potency. Importantly, replacing the side chain hydroxy group with a fluorine maintained much of the potency (2s, 57% vs. 2k, 74% and 2r, 21% vs. 2e, 30%). Consequently, the fluoro analog 2s has only one hydroxy group left for potential Phase II metabolism (e.g. glucuronide formation), and this remaining hydroxy group is a current target for replacement (Lai et al., 1998).

Using the same method as in the preceding example (Marsilje2000), the most potent inhibitor from the current indole series (2k) was analyzed for ATP competition by monitoring the % inhibition at increasing [ATP] while holding the inhibitor concentration constant. Since the [ATP] had little effect on the % inhibition (The % inhibition was 46% and 41% with 2k at 45 μM and [ATP] at 200 μM or 1,000 μM, respectively.), 2k is non-competitive with respect to ATP under these assay conditions.

In summary, an indole scaffold has been designed, and an initial SAR carried out, for the development of non-ATP competitive $pp60^{c-src}$ inhibitors. The potency of the best indole-based inhibitor from the current series was found to be close to that of the best naphthalene-based inhibitor. The % inhibition was 46% and 41% with 2k at 45 μM and [ATP] at 200 μM or 1,000 μM, respectively.

Example 3

Synthesis of Indole Derivative Protein Kinase Inhibitors

The following results show the synthesis and testing of indole derived protein kinase inhibitors. Four reaction schemes are provided and separately followed by experimental details for the preparation of the final product of each of these reaction schemes. These final products are examples of indole-base tyrosine kinase inhibitors wherein the synthesis with certain groups on the aryl ring of the indole moiety is illustrated (boronic acid, Scheme 1; OH, Scheme 2; an aliphatic amide extension, Scheme 3; and a phosphonic acid Scheme 4).

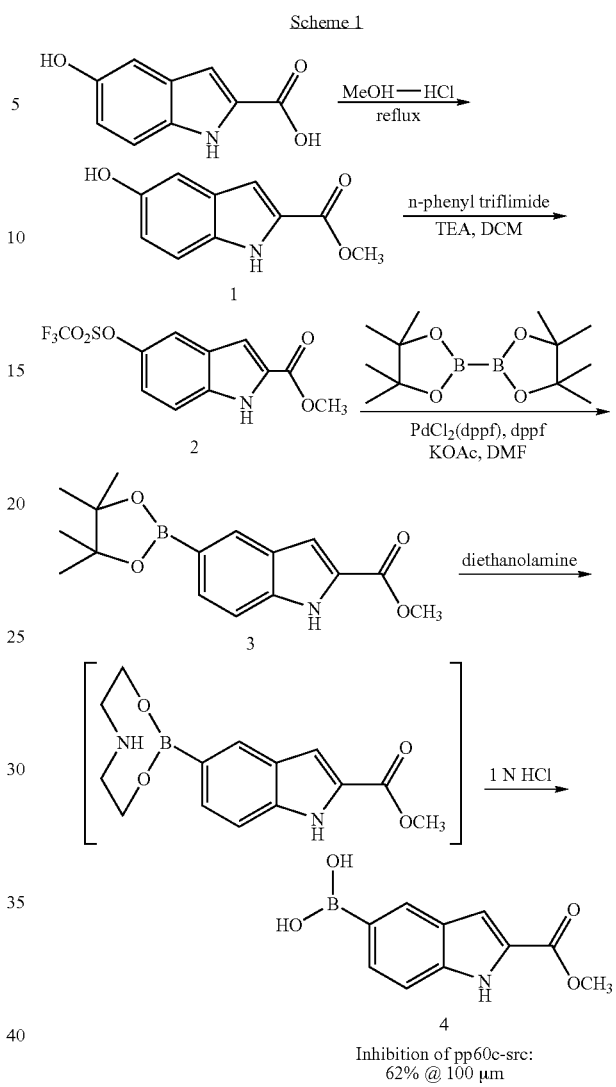

Scheme 1

Inhibition of pp60c-src: 62% @ 100 μm

Methyl 5-hydroxy-2-indolecarboxylate (1)

Dissolved 3.50 g 5-hydroxy-2-indolecarboxylic acid in anh. MeOH pre-saturated with HCl gas. Refluxed for 48 hours. Concentrated in vacuo and triturated with AcCN×3 to remove residual acid. Filtered through silica plug with EtOAc to remove baseline contamination. Recovered 4.32 g (quant. yield) TLC $R_f$=0.78 (EtOAc) 1H NMR (DMSO-$d_6$): 3.82 (s, 3H), 6.78 (d, J=8.8 Hz, 1H), 6.88 (s, 1H), 6.93 (s, 1H), 7.23 (d, J=8.8 Hz, 1H), 8.90 (s, 1H) 11.62 (s, 1H) FAB(+) MS m/e 191.9 (M+1)

Methyl 5-[(trifluoromethyl)sulfonyloxy]indole-2-carboxylate (2)

Added 150 ml anh. DCM to 3.24 g (17 mmol) methyl 5-hydroxy-2-indolecarboxylate (1) and 6.67 g (18.7 mm) n-phenyl trifluoromethane sulfonamide at 0° C. Added 2.6 ml triethylamine dropwise at which point clear yellow solution formed. Stirred at 0° C. for 1 hour. Warmed to room temperature and stirred for 2 hours. Concentrated in vacuo and purified through silica gel column (1/1 EtOAc/hexanes). Recovered 4.69 g (86%). TLC $R_f$=0.63 (1/1 EtOAc/hexanes). HPLC $R_f$=20.879 1H NMR (DMSO-$d_6$): 3.87 (s, 3H), 7.25 (s, 1H), 7.31 (d, J=9.2 Hz, 1H), 7.55 (d, J=9.2 Hz, 1H), 7.80 (s, 1H), 12.34 s, 1H) FAB(+) MS m/e 323.1 (M+1).

Methyl 5-methylindole-2-carboxylate, 4,4,5,5-tetramethyl-1,3,2-dioxaborolanemethyl (3)

500 mg 1.55 mmol methyl 5-[(trifluoromethyl)sulfonyloxy]indole-2-carboxylate (2), 37.9 mg (0.05 mmol) $PdCl_2$ (dppf), 432 mg (1.7 mmol) bispinacolatodiboron, 454.8 mg (4.65 mmol) potassium acetate, and 25.7 mg (0.05 mmol) dppf were added to a flask and vacuum dried at 40° C. for 2 hours. Added 20 ml anh dioxane and heated to 80° C. overnight. Reaction turned black as Pd black precipitated out. Filtered off catalyst and ran silica plug to remove baseline impurities. TLC $R_f$=0.51 (1/4 EtOAc/Hexane) Crude product was taken through to next reaction.

Methyl 5-boronyl indole-2-carboxylate (4)

391.2 mg (1.3 mmol) methyl 5-methylindole-2-carboxylate, 4,4,5,5-tetramethyl-1,3,2-dioxaborolanemethyl (3) was dissolved in EtOAc. 0.25 ml (2.6 mmol) diethanolamine was added, and the reaction was stirred at room temperature overnight. The white precipitate which formed was filtered and sonicated in 1 N HCl. The resulting white precipitate was filtered, dissolved in MeOH, and concentrated in vacuo. Recovered 36.6 mg (13%). HPLC $R_f$=13.912, 1H NMR (DMSO-$d_6$): 3.85 (s, 3H), 7.15 s, (1H), 7.36 (d, J=8.4 Hz, 1H), 7.67 (d, J=8.4 Hz, 1H), 7.87 (s, 1H), 8.14 (s, 1H), 11.91 (s, 1H).

(5-hydroxyindol-2-yl)-N-[(3-methoxyphenyl)methyl]carboxyamide (5)

Dissolved 2.00 g (11.3 mmol) 5-hydroxy-2-indolecarboxylic acid, 1.6 ml (12.4 mmol) 3 methoxybenzylamine, and 5.87 g (11.3 mmol) PyBOP in 10 ml anh. DMF. Cooled to 0° C. and added 5.9 ml (33.9 mmol) DIEA. Stirred for 5 min at 0° C. and allowed to warm to room temperature for 1 hour. Recovered 2.83 g (85% yield) TLC $R_f$=0.34 (1/1 EtOAc/hexanes) 1H NMR (DMSO-$d_6$): 3.70 (s, 3H), 4.43 (d, J=4.4 Hz, 2H) 6.69 (d, J=8.8 Hz, 1H), 6.78 (d, J=7.7 Hz, 1H), 6.83 (s, 1H), 6.86 (s, 1H), 6.94 (s, 1H), 7.20 (m, 3H), 8.92 (t, J=4.4 Hz, 1H), 11.36 (s, 1H) FAB(+) MS m/e 297.3 (M+1)

(5-hydroxyindol-2-yl)-N-[(3-hydroxyphenyl)methyl]carboxyamide (6)

Added 20 ml anh. DCM to 200 mg (0.67 mmol) (5-hydroxyindol-2-yl)-N-[(3-methoxyphenyl)methyl]carboxyamide(5) and cooled to –78° C. under argon. Added 4.0 ml (4.0 mmol, 6 eq) $BBr_3$. Held at –78° C. for 5 min and warmed to rt. After 90 min at rt, quenched with $H_2O$ and stirred for 10 min. Diluted rxn mix with EtOAc and washed with $NaHCO_3$ and brine. Dried organic layer over $MgSO_4$ and concentrated in vacuo. Ran through silica plug to remove baseline contamination. Recovered X mg. (80% yield.) TLC $R_f$=0.21 (1/1 EtOAc/hexanes). $^1$H NMR (DMSO-$d_6$): 4.38 (d, J=4.8 Hz, 2H), 6.59 (d, J=8.8 Hz, 1H), 6.71 (m, 3H) 6.83 (d, J=1.8 Hz, 1H), 6.94 (s, 1H), 7.08 (dd, J=7.7 Hz, 1H), 7.19 (d, J=8.8 Hz, 1H), 8.84 (t, J=5.9 Hz), 11.28, (s, 1H). FAB(+) MS m/e 283.2 (M+1)

Scheme 2

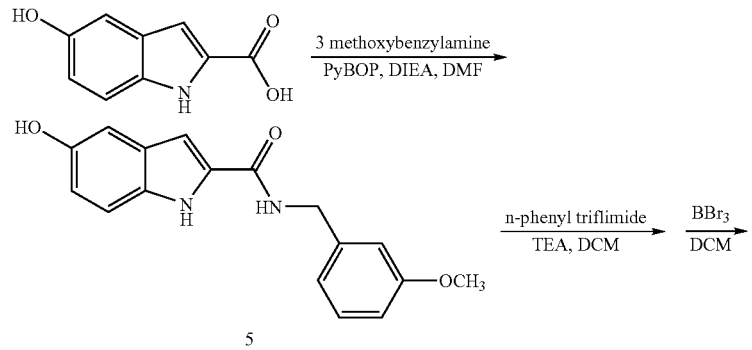

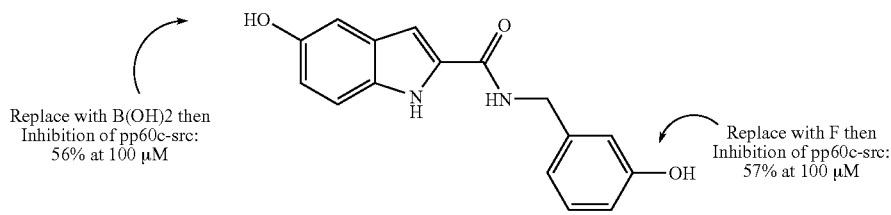

Replace with B(OH)2 then
Inhibition of pp60c-src:
56% at 100 µM

6
Inhibition of pp60c-src:
74% at 100 µM
IC50 = 38 µM
(Included in Manuscript)

Replace with F then
Inhibition of pp60c-src:
57% at 100 µM

55

Scheme 3

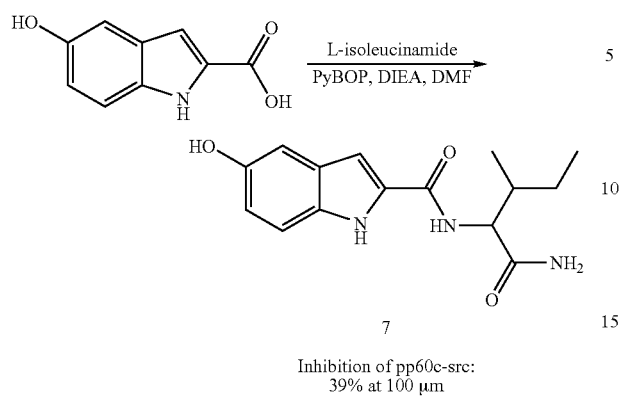

Inhibition of pp60c-src:
39% at 100 μm

N-(1-carbamoyl-2-methylbutyl)(5-hydroxyindol-2-yl)carboxyamide (7)

100 mg (0.56 mmol) 5-hydroxy-2-indolecarboxylic acid, 103.4 mg (0.62 mmol, 1.1 eq) L-isoleucinamide, and 291 mg (0.56 mmol, 1 eq) PyBOP were all dissolved in 1 ml anh DMF. The solution was cooled to 0° C. and 0.3 ml (1.68 mmol, 3 eq) DIEA was added. The reaction mixture was stirred for 1 min at 0° C. and at room temperature for 1 hour. The reaction was then diluted with EtOAc and washed with 1 N HCl×3 and saturated NaHCO3×3. The organic layer was dried over MgSO$_4$, and concentrated in vacuo to give 166.7 mg (91% yield.) TLC R$_f$=0.08 (1/1 EtOAc/hexanes). $^1$H NMR (DMSO-d$_6$): 0.83 (m, 6H), 1.15 (m, 2H), 1.68 (m, 1H), 1.83 (m, 1H), 4.29 (t, J=8.8 Hz, 1H), 6.69 (d, J=8.5 Hz, 1H), 6.83 (s, 1H), 7.01 (s, 1H), 7.06 (s, 1H), 7.19 (d, J=8.4 Hz, 1H), 7.48, (s, 1H), 8.00 (d, 9.2 Hz, 1H), 8.76 (s, 1H), 11.3, (s, 1H). FAB(+) MS m/e 290.1 (M+1)

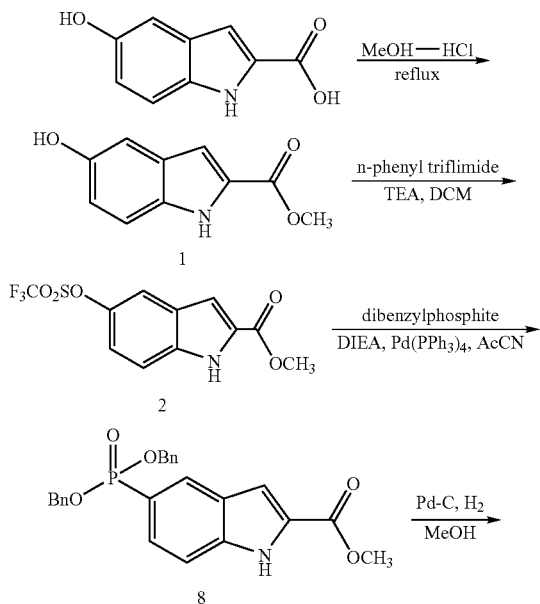

56

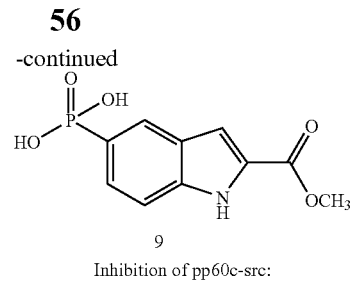

Inhibition of pp60c-src:
11% at 500 μM

Methyl 5-dibenzylphosphorylindole-2-carboxylate (8)

200 mg (0.62 mmol) methyl 5-[(trifluoromethyl)sulfonyloxy]indole-2-carboxylate (2), 195.8 mg (0.74 mmol, 1.2 eq) dibenzylphosphite, 0.14 ml (0.81 mmol, 1.3 eq) DIEA, and 35.7 mg (0.03 mmol, 5 mol %) Pd(PPh$_3$)$_4$ were all dissolved in anh AcCN under argon. The reaction mix was heated to 80° C. overnight. The solvent was removed under reduced pressure, and the title compound was isolated by silica gel chromatography. 130 mg (50% yield). TLC R$_f$=0.28 (1/1 EtOAc/hexanes) $^1$H NMR (DMSO-d$_6$): 3.85 (s, 3H), 4.98-5.01 (m, 4H), 7.28-7.32 (m, 11H), 7.53-7.55 (m, 2H), 8.17 (d, J=14.6 Hz, 1H) $^{31}$P NMR (DMSO-d$_6$): 23.89.

Methyl 5-phosphonoindole-2-carboxylate

Methyl 5-dibenzylphosphorylindole-2-carboxylate (8) (125 mg) was dissolved in 10 ml MeOH. 20 mg Pd—C was added and the mixture was hydrogenated in a Parr apparatus overnight. Filtered off catalyst and removed solvent under reduced pressure. Obtained 72.5 mg (73% yield). TLC R$_f$=baseline in EtOAc. $^1$H NMR (DMSO-d$_6$): 3.84 (s, 3H), 7.24 (s, 1H), 7.44-7.49 (m, 2H), 8.01 (d, J=14.3 Hz, 1H) 12.11 (s, 1H) $^{31}$P NMR (DMSO-d$_6$): 17.22.

The ester compounds in this example could be increased in potency by converting the ester to an amide and/or adding additional specificity elements.

Example 4

Synthesis of Further Indole Derivative Protein Kinase Inhibitors

The synthesis of some further elaborated indole inhibitors is illustrated below. These syntheses should result in compounds with greater potency against pp60c-src and other tyrosine kinases. The methyl ester group can be subsequently converted into various amide derivatives to increase potency.

Scheme 1:

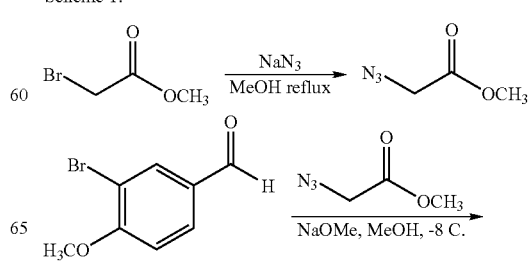

57 58
-continued  -continued
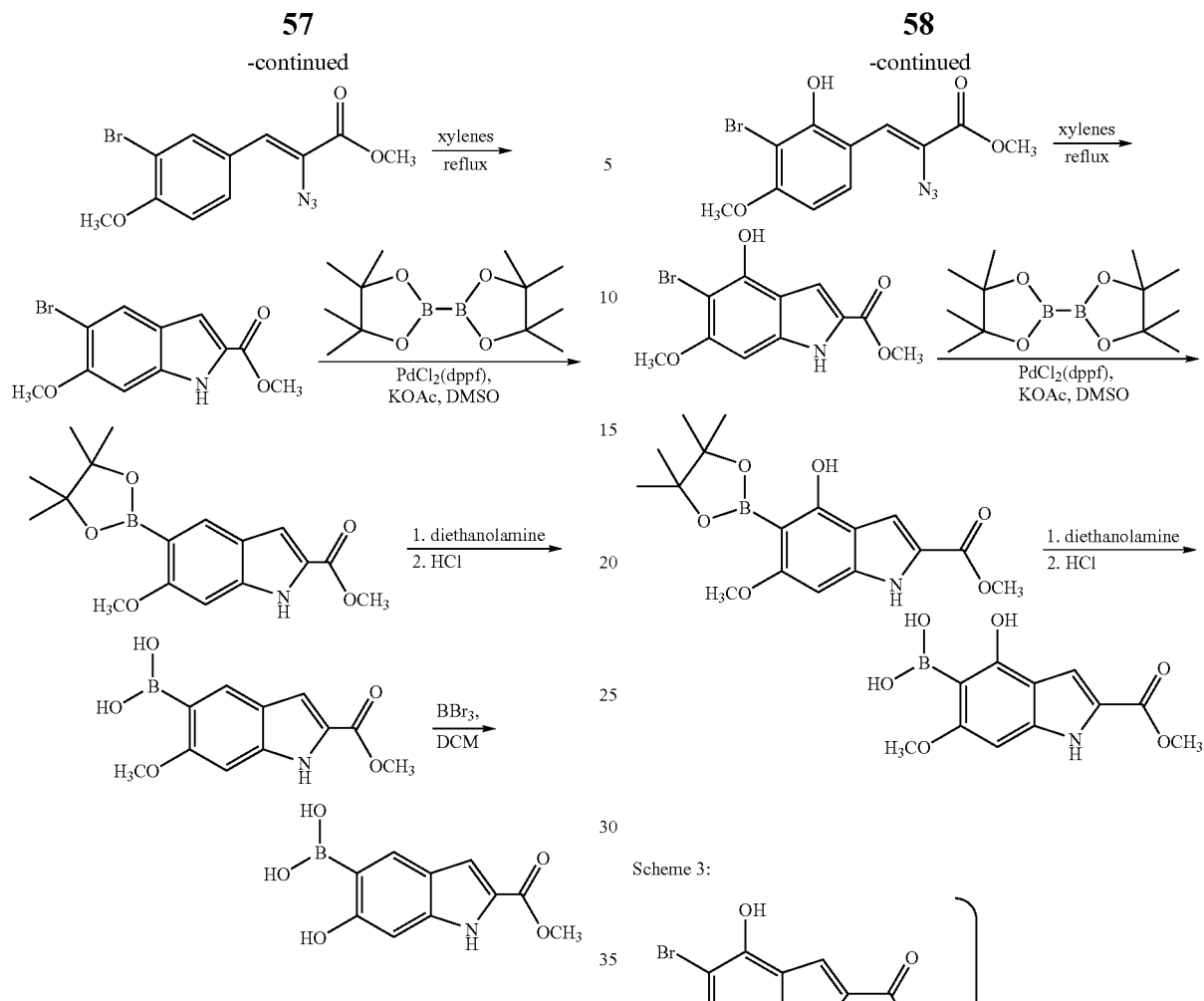
Scheme 2:
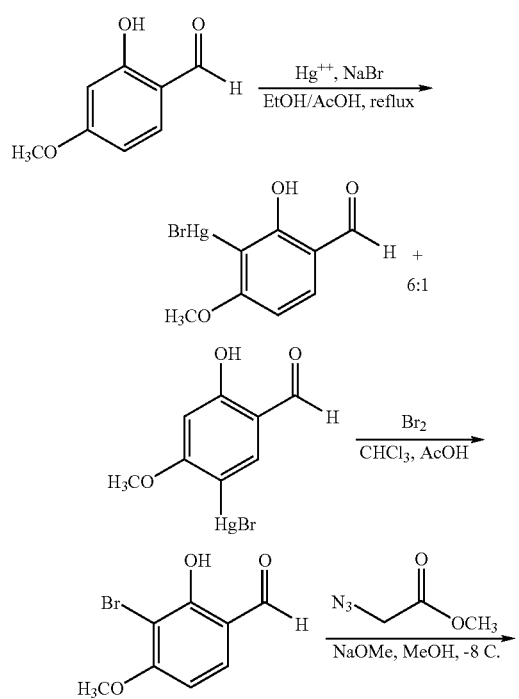
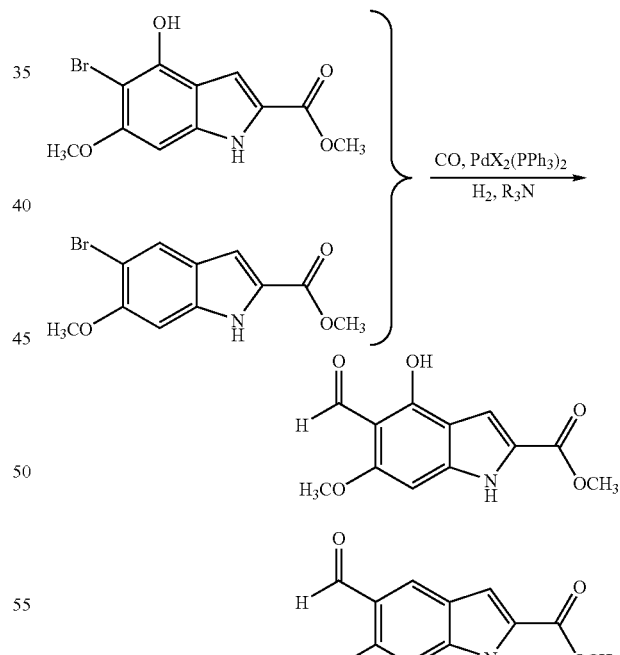
Example 5
Toxicity of Src Inhibitors
There is considerable recent literature support for targeting pp60[c-src] (Src) as a broadly useful approach to cancer therapy without resulting in serious toxicity. For example, tumors that display enhanced EGF receptor PTK signaling, or overexpress the related Her-2/neu receptor, have constitutively activated Src and enhanced tumor invasiveness. Inhibition of Src in these cells induces growth arrest, triggers apoptosis, and reverses the transformed phenotype (Karni et al., 1999). It is known that abnormally elevated Src activity allows transformed cells to grow in an anchorage-independent fashion. This is apparently caused by the fact that extracellular matrix signaling elevates Src activity in the FAK/Src pathway, in a coordinated fashion with mitogenic signaling, and thereby blocks an apoptotic mechanism which would normally have been activated. Consequently FAK/Src inhibition in tumor cells may induce apoptosis because the apoptotic mechanism which would have normally become activated upon breaking free from the extracellular matrix would be induced (Hisano et al., 1997). Additionally, reduced VEGF mRNA expression was noted upon Src inhibition and tumors derived from these Src-inhibited cell lines showed reduced angiogenic development (Ellis et al., 1998).

The issue of potential toxicity of Src inhibition has been addressed with very promising results. For example, a knockout of the Src gene in mice led to only one defect, namely osteoclasts that fail to form ruffled borders and consequently do not resorb bone. However, the osteoclast bone resorb function was rescued in these mice by inserting a kinase defective Src gene (Schwartzberg et al., 1997). This suggested that Src kinase activity can be inhibited in vivo without triggering the only known toxicity because the presence of the Src protein is apparently sufficient to recruit and activate other PTKs (which are essential for maintaining osteoclast function) in an osteoclast essential signaling complex.

Src has been proposed to be a "universal" target for cancer therapy since it has been found to be over activated in a growing number of human tumors, in addition those noted above (Levitzki, 1996). The potential benefits of Src inhibition for cancer therapy appear to be four-fold based upon the cited, and additional, literature. They are: 1) inhibition of uncontrolled cell growth caused by autocrine growth factor loop effects, etc.; 2) inhibition of metastasis due to triggering apoptosis upon breaking free from the cell matrix; 3) inhibition of tumor angiogenesis via reduced VEGF levels; and 4) low toxicity.

Figure 15B:
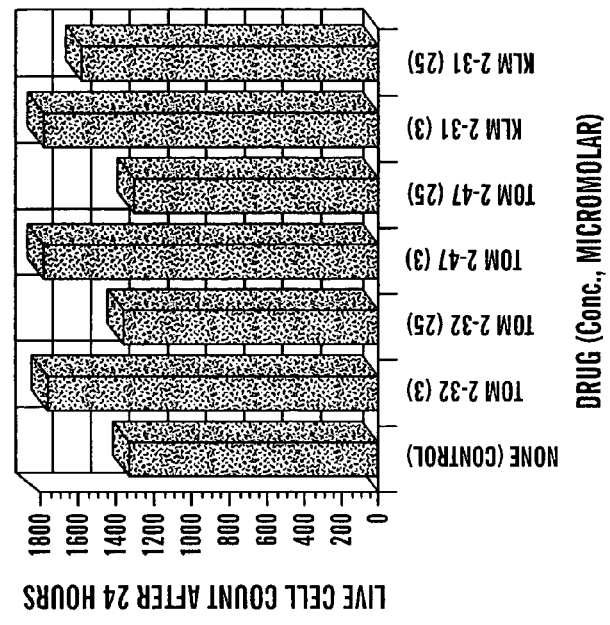
FIG. 15B shows the results from tests of the src inhibitors for inhibition of normal human fibroblast cell growth. No inhibition of normal cell growth was observed (both subconfluent and confluent; however, some enhanced growth was observed instead), thus indicating that these inhibitors are not toxic to normal cells even at a 10-fold higher concentration.
Figure 15A:
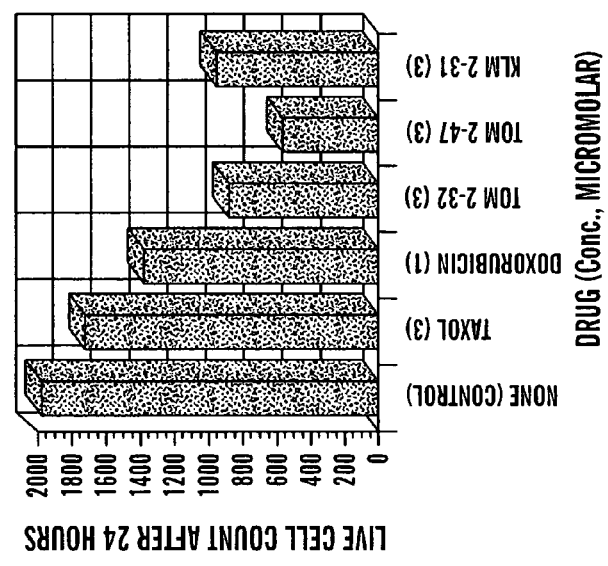
FIG. 15A shows a comparison of taxol and doxorubicin (both were more effective than etoposide & cisplatin in the tumor cell culture) with the three Src inhibitors mentioned above using ovarian tumor cells from tumor N015.
Figure 15C:
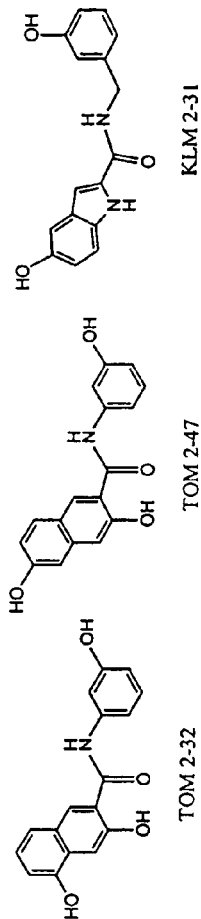
FIG. 15C provides the structures of the src inhibitors TOM 2-32, TOM 2-47, and KLM 2-31.

The initial non-peptide Src inhibitors have also shown very encouraging results in four different series of cell culture assays. 1) In the NIH 60-tumor cell panel assay, broad activity (as one would expect for a Src inhibitor) was seen against the tumor cell lines, including the prostate lines. For example, three of the inhibitors gave the following growth inhibition $IC_{50}$ values against the NIH prostate cancer cell lines: TOM 2-32 (PC-3, 15 μM; DU-145, 38 μM), TOM 2-47 (PC-3, 19 μM), KLM 2-31 (PC-3, 39 μM; DU-145, >100 μM). 2) In the v-Src transformed normal rat kidney cell line (LA25) TOM 2-47 & TOM 2-32 specifically blocked the v-Src induced cell growth without inhibiting the normal growth of the parent non-transformed cells. This result showed that the inhibitors do not affect normal cells but are effective in blocking Src induced cell transformation. 3) The Src inhibitors to the cancer drugs etoposide, taxol, doxorubicin and cisplatin in ovarian tumors from three different patients and an abdominal carcinoma from another patient. In all cases, the Src inhibitors were at least as effective, and typically more effective, than the known cancer drugs, with full efficacy seen at the lowest dose tested (3 μM). As a representative example, a comparison of taxol and doxorubicin (they were more effective than etoposide & cisplatin in this particular tumor cell culture) with the three Src inhibitors mentioned above utilizing ovarian tumor cells from tumor N015 is shown in FIG. 15A. 4) The Src inhibitors were also tested for inhibition of normal human fibroblast cell growth and found no inhibition of normal cell growth (both sub-confluent and confluent; some enhanced growth was observed instead), indicating that these inhibitors are not toxic to normal cells even at a 10-fold higher concentration. An example of his data is given in FIG. 15B.

Overall, the cell data obtained thus far shows what one might expect for Src inhibitors, i.e. broad activity against many cancer cell lines with little or no normal cell toxicity.

The preliminary Src inhibitors are lead structures from which it is possible to design more potent and selective inhibitors. In addition to utilizing the tyrosine kinase crystal structures, molecular modeling studies can be carried out with the natural product tyrosine kinase inhibitor damnacanthal (Faltynek et al., 1995) to investigate its peptide-competitive binding mode. These additional modeling studies are enable one to design further analogs of Src inhibitors wherein the key pharmacophore elements of damnacanthal are incorporated into the new inhibitors. Their syntheses will be undertaken and the isolated Src testing done as reported (Marsilje 2000).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

LITERATURE CITED

The following references which were cited herein, are hereby incorporated by reference into this application:

Ajay, Murcko, M. A. (1995) *Computational Methods to Predict Binding Free Energy in Ligand-Receptor Complexes*. J. Med. Chem., 38, 4953-4967.

Alberts, B., Bray, D., Lewis, J., Raff, M., Roberts, K. & Watson, J. D. (1994) Molecular Biology Of The Cell, 3rd ed., Garland Publishing, Inc., New York, pp 97, 508 & 667.

Alfaro-Lopez, J., Yuan, W., Phan, B. C., Kamath, J., Lou, Q., Lam, K. S., Hruby, V. J. (1998) *Discovery of a Novel Series of Potent and Selective Substrate-Based Inhibitors of p60c-src Protein Tyrosine Kinase: Conformational and Topographical Constraints in Peptide Design*. J. Med. Chem., 41, 2252-2260.

Backes, B. J., Virgilo, A. A., Ellman, J. A. (1996) *Activation Method to Prepare a Highly Reactive Acylsulfonamide "Safety-Catch" Linker for Solid-Phase Synthesis*. J. Am. Chem. Soc., 118, 3055-3056.

Baggio, R., Elbaum, D., Kanyo, Z. F., Carroll, P. J., Cavalli, C., Ash, D. E., Christianson, D. W. (1997) *Inhibition of Mn2+-Arginase by Borate Leads to the Design of a Transition State Analog Inhibitor, 2(S)-Amino-6-boronohexanoic Acid*. J. Am. Chem. Soc., 119, 8107-8108.

Barnekow, A.; Paul, E.; Schartl, M. (1987) *Expression of the c-src protooncogene in human skin tumors*. Cancer Res., 47, 235-240.

Benson, W. H., Birge, W. J., Dorough, H. W. (1984) Environ. Toxicol. Chem., 3, 209. Chem. Abstr. 101:124626g.

Bhagwat, S. S., Gude, C. (1994) *N-Alkylation of indole ring using Mitsunobu reaction*. Tet. Lett., 35, 1847-1850.

Bjorge, J. D., O'Connor, T. J., Fujita, D. J. (1996) *Activation of human pp60$^{c-src}$*. Biochemistry & Cell Biology, 74, 477-484.

Bjelfman, C.; Hedborg, F.; Johansson, I.; Nordenskjold, M.; Pahlman, S. (1990) *Expression of the neuronal for of* pp60c-src in neuroblastoma in relation to clinical stage and prognosis. Cancer Res, 50, 6908-6914.

Bohacek, R. S., McMartin, C., Guida, W. C. (1996) *The Art and Practice of Structure-Based Drug Design: A Molecular Modeling Perspective*. Medicinal Research Reviews, 16, 3-50 (see p. 43).

Boyd, M. R., Paull, K. D. (1995) *Some practical considerations and applications for the National Cancer Institute in vitro anticancer drug discovery screen*. Drug Development Research, 34, 91-109.

Brooks, S. P. J. & Storey, K. B. (1992) *Bound and Determined: A Computer Program for Making Buffers of Defined Ion Concentrations*. Analytical Biochemistry, 201, 119-126.

Brown, D. (1997) *Future Pathways for Combinatorial Chemistry*. Molecular Diversity, 2(4), 217-222.

Budde, R. J. A., McMurray, J. S., Saya, H., Gallick, G. E. & Levin, V. A. (1995) *Discovery, Development, and Testing of Substrates and Inhibitors of pp60$^{c\text{-}src}$*. International Journal of Pharmacognosy, 33, 27-34.

Budde, R. J. A., Ke, S., Levin, V. A. (1994) *Activity of pp60c-src in 60 different cell lines derived from human tumors*. Cancer Biochem. Biophys., 14, 171-175.

Burger, A. M., Kaur, G., Alley, M. C., Supko, J. G., Malspeis, L., Grever, M. R. & Sausville, E. A. (1995) *Tyrphostin AG17, [(3,5-Di-tert-butyl-4-hydroxybenzylidene)-malonitrile], inhibits cell growth by disrupting mitochondria*. Cancer Research, 55, 2794-2799.

Burke, T. R.; Lim, B.; Marquez, V. E.; Li, Z-H.; Bolen, J. B.; Stefanova, I.; Horak, I. D. (1993) J. Med. Chem. 36, 425.

Choi, S. (1999), Ph.D. Thesis SUNY at Buffalo, Buffalo, N.Y.

Cooper, C. M. (1990) Oncogenes. Jones and Bartlett Publishers, Boston, Mass.

Coughlin, J. R. (1996) *Inorganic borates-chemistry, human exposure, and health and regulatory guidelines*. J. Trace Elements in Experimental Medicine, 9, 137-151.

Courtneidge, S. A. (1994) *Protein tyrosine kinases, with emphasis on the Src family*. Seminars in Cancer Biology, 5, 239-246.

Cox, S., Radzio-Andzelm, E. & Taylor, S. S. (1994) *Domain movements in protein kinases*. Current Opinion in Structural Biology, 4(6), 893-901.

Culver, B. D., Hubbard, S. A. (1996) *Inorganic boron health effects in humans—and aid to risk assessment and clinical judgment*. J. Trace Elements in Experimental Medicine, 9, 175-184.

Davis, P. D.; Hill, C. H.; Keech, E.; Lawton, G.; Nixon, J. S.; Sedgwick, A. D.; Wadsworth, J.; Westmacott, D.; Wilkinson, S. E. (1989) FEBS Lett. 259(1), 61.

Davis, P. D.; Elliott, L. H.; Harris, W.; Hill, C. H.; Hurst, S. A.; Keech, E.; Kumar, M. K. H.; Lawton, G.; Nixon, J. S.; Wilkinson, S. E. (1992) J. Med. Chem. 35, 994.

Ellis, L. M., Staley, C. A., Liu, W., Fleming, R. Y., Parikh, N. U., Bucana, C. D., & Gallick, G. E. (1998) *Down-regulation of vascular endothelial growth factor in a human colon carcinoma cell line transfected with an antisense expression vector specific for c-src*. Journal of Biological Chemistry 273 (2): 1052-1057.

Ezquerra, J., Pedregal, C., Lamas, C., Barluenga, J., Perez, M., Garcia-Martin, M. A., Gonzalez, J. M. (1996) *Efficient reagents for the synthesis of 5-, 7-, and 5,7-substituted indoles starting from aromatic amines: scope and limitations*. J. Org. Chem., 61, 5804-5812.

Faltynek, C., et al. (1995) *Damnacanthal is a highly potent, selective inhibitor of p56lck tyrosine kinase activity*. Biochemistry 34, 12404-12410.

Faltynek, C. R.; Wang, S.; Miller, D.; Mauvais, P.; Gauvin, B.; Reid, J.; Xie, W.; Hoekstra, S.; Juniewicz, P.; Sarup, J.; Lehr, R.; Sawutz, D. G.; Murphy, D. J. (1995) Enzyme Inhibition 9, 111.

Fanning, P.; Bulovas, K.; Saini, K. S.; Libertino, J. A.; Joyce, A. D.; Summerhayes, I. C. (1992) *Elevated expression of pp60$^{c\text{-}src}$ in low grade human bladder carcinoma*. Cancer Research, 52, 1457-1462.

Fredenhagen, A.; Mett, H.; Meyer, T.; Buchdunger, E.; Regenass, U.; Roggo, B. E.; Petersen, F. J. (1995) Antibiotics 48, 1355.

Froyen, P. (1997) Tetrahedron Lett. 38(30), 5359.

Fry, D. W., Kraker, A. J., McMichael, A., Ambroso, L. A., Nelson, J. M. Leopold, W. R., Connors, R. W. & Bridges, A. J. (1994) *A Specific Inhibitor of the Epidermal Growth Factor Receptor Tyrosine Kinase*. Science, 265, 1093-1095.

Glass, D. B., Cheng, H.-C., Mende-Mueller, L., Reed. J. & Walsh, D. A. (1989) *Primary structure determinants essential for potent inhibition of cAMP-dependent protein kinase by inhibitory peptides corresponding to the active portion of the heat-stable inhibitor protein*. J. Biol. Chem., 264, 8802-8810.

Groundwater, P. W., Solomons, K. R. H., Drewe, J. A. & Munawar, M. A. (1996) *Protein Tyrosine Kinase Inhibitors*. Progress in Medicinal Chemistry, 33, 233-329.

Hanks, S. K. & Hunter, T. (1995) Protein kinases. 6. *The eukaryotic protein kinase superfamily: Kinase (catalytic) domain structure and classification*. FASEB J., 9, 576-596.

Hanke, J. H., Gardner, J. P., Dow, R. L., Changelian, P. S., Brissette, W. H., Weringer, E. J., Pollok, B. A. & Connelly, P. A. (1996) *Discovery of a novel, potent, and Src family-selective tyrosine kinase inhibitor*. J. Biol. Chem., 271, 695-701.

Hisano, C., Nakano, S., Fujishima, H., Masumoto, N., Tatsumoto, T., & Niho. Y. (1997) *src oncogene inhibits detachment-induced apoptosis through constitutive activation of p125FAK in HAG-1 human epithelial cells*. Proc. Annu. Meet. Am. Assoc. Cancer Res. 38:A1925.

Hsiao, G. K., Hangauer, D. G. (1998) *A Facile Synthesis of tert-Butyl 2-[(Benzyloxycarbonyl)amino]-3-(4,4,5,5-tetramethyl-1,3,2-dioxaborolan-2-yl)propionate: An Orthogonally Protected Boronic Acid Analog of Aspartic Acid*. Synthesis, 1043-1046.

Hsu, C-Y., J., Jacoski, M. V., Maguire, M. P., Spada, A. P. & Zilberstein, A. (1992) *Inhibition Kinetics and Selectivity of the Tyrosine Kinase Inhibitor Erbstatin and a Pyridone-based Analog*. Biochemical Pharmacology, 43, 241-2477.

Huang, C-K., Wu, F-Y., Ai, Y-X. (1995) *Polyhydroxylated 3-(N-phenyl) carbamoyl-2-iminochromene derivatives as potent inhibitors of tyrosine kinase p60c-src*. Bioorg. & Med. Chem. Lett., 5, 2423-2428.

Hubbard, S. R., Wei, L, Ellis, L, & Hendrickson, W. A. (1994) *Crystal structure of the tyrosine kinase domain of the human insulin receptor*, Nature, 372, 746-754.

Hubbard, S. R. (1997) *Crystal structure of the activated insulin receptor tyrosine kinase in complex with peptide substrate and ATP analog*. The EMBO Journal, 16, 5572-5581.

Hughes, R. L., Smith, I. C., Lawless, E. W. (1967) Production of the Boranes and Related Rearch, Holtzman R. T., Ed., Academic Press, New York, pp 291-294.

Hunter, T. (1987) *A thousand and one protein kinases*. Cell, 50, 823-829.

Hunter, T. (1994) *1001 protein kinases redux-towards 2000*. Seminars in Cell Biology, 5, 367-376.

Hunter, T. (1998) *The Croonian Lecture 1997. The phosphorylation of proteins on tyrosine: its role in cell growth and disease*. Philosophical Transactions of the Royal Society of London—Series B: Biological Sciences 353 (1368): 583-605.

Hutchins, C., Greer, J. (1991) *Comparative modeling of proteins in the design of novel renin inhibitors*. Critical Reviews in Biochemistry & Molecular Biology, 26, 77-127.

Ishiyama, T., Murata, M., Miyaura, N. (1995) *Palladium(0)-catalyzed cross-coupling reaction of alkoxydboron with haloarenes: A direct procedure for arylboronic esters*. J. Org. Chem., 60, 7508-7510.

Ishiyama, T., Itoh, Y., Kitano, T., Miyaura, N. (1997) *Synthesis of arylboronates via the palladium(0)-catalyzed cross-coupling reaction of tetra(alkoxo)diborons with aryl triflates*. Tet. Lett., 38, 3447-3450.

Karni, R., Jove R., & Levitzki A. (1999) *Inhibition of pp60c-src reduces Bcl-X expression and reverses the transformed phenotype of cells overexpressing EGF and HER-2 receptors*. Oncogene 18(33): 4654-4662.

Kelloff, G. J., Fay, J. R., Steele, V. E., Lubet, R. A., Boone, C. W., Crowell, J. A. (1996) *Epidermal growth factor receptor tyrosine kinase inhibitors as potential cancer chemopreventatives*. Cancer Epidemiology, Biomarkers & Prevention, 5, 657-666.

Kettner, C. A., Shenvi, A. B. (1984) *Inhibition of the Serine Proteases Leukocyte Elastase, Pancreatic Elastase, Cathepsin G, and Chymotrypsin by Peptide Boronic Acids*. J. Biol. Chem., 259, 15106-15114.

Kim. M. H., Lai, J. H. & Hangauer, D. G. (1994) *Tetrapeptide tyrosine kinase inhibitors: Enantioselective synthesis of p-hydroxymethyl-L-phenylalanine, incorporation into a tetrapeptide, and subsequent elaboration into p-(R,S-hydroxyphosphonomethyl)-L-phenylalanine*. Int. J. Peptide Protein Res., 44, 457-465.

Kinder, D. H., Frank, S. K., Ames, M. M. (1990) *Analogues of Carbamyl Aspartate as Inhibitors of Dihydroorotase: Preparation of Boronic Acid Transition-State Analogues and a Zinc Chelator Carbamylhomocysteine*. J. Med. Chem., 33, 819-823.

Klein, G. (1990) *Multistep emancipation of tumors from growth control: can it be curbed in a single step?* BioEssays, 12, 347-350.

Knighton, D. R., Cadena, D. L., Zheng, J., Ten Eyck, L. F., Taylor, S. S. & Sowadski, J. M. (1993) *Structural features that specify tyrosine activity deduced from homology modeling of the epidermal growth factor receptor*. Proc. Natl. Acad. Sci. U.S.A., 90(11), 5001-5.

Kolibaba, K. S. & Druker, B. J. (1997) *Protein tyrosine kinases and cancer*. Biochimica et Biophysica Acta, 1333: F217-F248.

Lai, J. H., Marsilje, T. M., Choi, S., Nair, S. A., Hangauer, D. G. (1998) *The design, synthesis and activity of pentapeptide pp60c-src inhibitors containing L-phosphotyrosine mimics*. J. Peptide Res., 51, 271-281.

Lai, J. H., Pham, H. & Hangauer, D. G. (1996) *Synthesis of a Vicinal Tricarbonyl Amide Derivative of L-Phenylalanine*. J. Org. Chem., 61, 1872-1874.

Lam, K. S. (1997) *Application of Combinatorial Library Methods in Cancer Research an Drug Discovery*. Anti-Cancer Drug Design, 12(3), 145-167.

Lawrence, D. S. & Niu, J. (1998) *Protein Kinase Inhibitors: The Tyrosine-Specific Protein Kinases*. Pharmacol. Ther., 77(2), 81-114.

Levitzki, A. (1996a) *Targeting signal transduction for disease therapy*. Current Opinion in Cell Biology, 8, 239-244.

Levitzki, A. (1996b) *SRC as a target for anti-cancer drugs*. Anti-Cancer Drug Design, 11, 175-182.

Levitzki, A.; Gazit, A. (1995) *Tyrosine Kinase Inhibition: An Approach to Drug Development*. Science, 267, 1782-1788.

Li, H., Liu, T. F., Lazrak, A., Peracchia, C., Goldberg, G. S., Lampe, P. D., Johnson, R. G. (1996) *Properties and regulation of gap junctional hemichannels in the plasma membranes of cultured cells*. J. Cell. Biol., 134, 1019-1030.

Loomis, W. D. & Durst, R. W. (1992) *Chemistry and biology of boron*. BioFactors, 3, 229-239.

Lou, Q., Leftwich, M. E., McKay, T., Salmon, S. E., Rychetsky, L. & Lam, K. S. (1997) *Potent Pseudosubstrate-based Peptide Inhibitors for p60$^{c-src}$ Protein Tyrosine Kinase*. Cancer Research, 57(10), 1877-1881.

Lou, Q., Leftwich, M. E. & Lam, K. S. (1996) *Identification of GIYWHHY as a Novel Peptide Substrate for Human p60c-src Protein Tyrosine Kinase*. Biorganic & Medicinal Chemistry, 4, 677-682.

Luttrell, D. K.; Lee, A.; Lansing, T. J.; Crosby, R. M.; Jung, K. D.; Willard, D.; Luther, M.; Rodriguez, M.; Berman, J.; Gilmer, T. M. (1994) *Involvement of pp60$^{c-src}$ with two major signaling pathways in human breast cancer*. Proc. Natl. Acad. Sci. USA, 91, 83-87.

Lynch, S. A.; Brugge, J. S.; Fromowitz, F.; Glantz, L.; Wang, P.; Caruso, R.; Viola, M. V. (1993) *Increased expression of the src proto-oncogene in hairy cell leukemia and a subgroup of B-cell lymphomas*. Leukemia, 7, 1416-1422.

Madhusudan, Trafny, E. A., Xuong, N-H, Adams, J. A., Ten Eyck, L. F., Taylor, S. S. & Sowadski, J. M. (1994) *cAMP-dependent protein kinase: Crystallographic insights into substrate recognition and phosphotransfer*. Protein Science, 3, 176-187.

Mao, W. G., Irby, R., Coppola, D., Fu, L., Turner, J. (1997) *Activation of c-src by receptor tyrosine kinases in human colon cancer cells with high metastatic potential*. Oncogene, 15, 3083-3090.

Marsilje, T. H., Milkiewicz, K. L., & Hangauer, D. L. (2000) *The design, synthesis and activity of non-ATP competitive inhibitors of pp60c-src tyrosine kinase 1. Hydroxynaphthalene Derivatives*. Bioorganic and Medicinal Chemistry Letters, in press.

Marx, J. (1990) *Oncogenes evoke new cancer therapies*. Science, 249, 1376-1378.

National Cancer Institute (1989) Survey of Compounds which have been tested for carcinogenic activity. NIH Publication No. 49-468, p. 16.

Matteson, D. S., Kandil, S. A., Soundararajan, R. (1990) *Synthesis of Asymmetrically Deuterated Glycerol and Dibenzylglyceraldehyde via Boronic Esters*. J. Am. Chem. Soc., 112, 3964-3969.

Matteson, D. S. (1988) Acc. Chem. Res., 21, 294-300.

Matteson, D. S., Kandil, A. A. (1987) *Conversion of α-halo boronic esters to inverted α-(methylsulfonyl)oxy boronic esters*. J. Org. Chem., 52, 5121-5124.

Matteson, D. S., Soloway, A. H., Tomlinson, D. W., Campbell, J. D., Nixon, G. A. (1964) J. Med. Chem., 7, 640.

Mazurenko, N. N.; Kogen, E. A.; Zborovskaya, I. B.; Kisseljov, F. L. (1992) *Expression of pp60$^{c-src}$ in human small cell and non-small cell long carcinomas*. European J. of Cancer, 28, 372-377.

Milkiewicz, K.; Marsilje, T.; Woodward Jr, R.; Bifulco Jr, N.; Hangauer, M.; Hangauer, D. G. (2000) *The design, synthesis and activity of non-ATP competitive inhibitors of pp60c-src tyrosine kinase 2. Hydroxyindole Derivatives*. Bioorganic and Medicinal Chemistry Letters, in press.

Mohammadi, M., Schlessinger, J., Hubbard, S. R. (1996) *Structure of the FGF Receptor Tyrosine Kinase Domain Reveals a Novel Autoinhibitory Mechanism.* Cell, 86, 577-587.

Mohammadi, M., McMahon, G., Li, S., Tang, C., Hirth, P., Yeh, B. K., Hubbard, S. R., Schlessinger, J. (1997) *Structures of the Tyrosine Kinase Domain of Fibroblast Growth Factor Receptor in Complex with Inhibitors.* Science, 276, 955-960.

Morin, C. (1994) *The Chemistry of Boron Analogues of Biomolecules.* Tetrahedron, 50, 12521-12569.

Murakami, Y., Otsuka, K. Wada, Y., Morikawa, A. (1990) *The partial oxidation of ethane over a $B_2O_3$-$Al_2O_3$ catalyst.* Bull. Chem. Soc. Jpn., 63, 340-346.

Nair, S. A., Kim, M. K., Warren, S. D., Choi, S., Songyang, Z., Cantley, L. C. & Hangauer, D. G. (1995). *Identification of Efficient Pentapeptide Substrates for the Tyrosine Kinase $pp60^{c-src}$.* J. Med. Chem., 38, 4276-4283.

Nair, S. A., Lee, B. & Hangauer, D. G. (1995b). *Synthesis of Orthogonally Protected L-Homocysteine and L-2-Amino-4-phosphonobutanoic Acid From L-Homoserine.* Synthesis, 7, 810-814.

Nielsen, F. H. (1997) *Boron in human and animal nutrition.* Plant & Soil, 193, 199-208.

Otsuka, K., Uragami, Y., Hatano, M. (1992) *Tile partial oxidation of ethane to acetaldehyde.* Catalysis Today, 13, 667-672.

Parsons, J. T. & Parsons, S. J. (1997) *Src family protein tyrosine kinases: cooperating with growth factor and adhesion signaling pathways.* Current Opinion in Cell Biology, 9, 187-192.

Patrick, D. R. & Heimbrook, D. C. (1996) *Protein Kinase Inhibitors For The Treatment of Cancer.* Drug Discovery Today, 1, 325-330.

Pavia, M. R., Cohen, M. P., Dilley, G. J., Dubuc, G. R., Durgin, T. L., Forman, F. W., Hediger, M. E., Milot, G., Powers, T. S., Sucholeiki, I., Zhou, S. & Hangauer, D. G. (1996) *The Design and Synthesis of Substituted Biphenyl Libraries.* Biorganic & Medicinal Chemistry, 4, 659-666.

Posner, I., Engel, M., Gazit, A. & Levitzki, A. (1994) *Kinetics of Inhibition by Tyrphostins of the Tyrosine Kinase Activity of the Epidernzal Growth Factor Receptor and Analysis by a New Computer Program.* Molecular Pharmacology, 45, 673-683.

Powis, G. (1991) *Signal targets for anticancer drug development.* TIPS, 188-194.

Ramdas, L., Obeyesekere, N. U., McMurray, J. S., Gallick, G. E., Seifert, W. E. Jr. & Budde, R. J. (1995) *A tyrphostin-derived inhibitor of protein tyrosine kinases: isolation and characterization.* Archives of Biochemistry & Biophysics, 323, 237-242.

Ramdas, L., McMurray, J. S. & Budde, R. J. (1994) *The degree of inhibition of protein tyrosine kinase activity by tyrphostin 23 and 25 is related to their instability.* Cancer Research, 54, 867-869.

Rewcastle, G. W., Palmer, B. D., Thompson, A. M., Bridges, A. J., Cody, D. R., Zhou, H. Fry, D. W., McMichael, A. & Denny, W. A. (1996) *Tyrosine Kinase Inhibitors. 10. Isomeric 4-[(3-Bromophenyl)amino]pyrido[d]-pyrimidines Are Potent ATP Binding Site Inhibitors of the Tyrosine Kinase Function of the Epidermal Growth Factor Receptor.* J. Med. Chem., 39, 1823-1835.

Rudd, C. E.; Janssen, O.; Prasad, K. V. S.; Raab, M.; da Silva, A.; Telfer, J. C.; Yamamoto, M. (1993) *src-related protein tyrosine kinases and their surface receptors.* Biochimica et Biophysica Acta, 1155, 239-266.

Saperstein, R., Vicario, P. P., Strout, H. V., Brady, E., Slater, E. E., Greenlee, W. J., Ondeyka, D. L., Patchett, A. A. & Hangauer, D. G. (1989) *Design of a selective insulin receptor tyrosine kinase inhibitor and its effect on glucose uptake and metabolism in intact cells.* Biochemistry, 28, 5694-5701.

Sawutz, D. G.; Bode, D. C.; Briggs, G. M.; Reid, J. R.; Canniff, P.; Caldwell, L.; Faltynek, C. R.; Miller, D.; Dunn, J. A.; Garavilla, L.; Guiles, J. W.; Weigelt, C.; Michne, W.; Treasurywala, A. M.; Silver, P. J. (1996) Biochem. Pharmacol. 51, 1631.

Schwartzberg, P. L., et al. (1997) *Rescue of osteoclast function by transgenic expression of kinase-deficient Src in src–/– mutant mice.* Genes & Development 11: 2835-2844.

Shiraishi, T., Owada, M. K., Tatsuka, M., Yamashita, T., Watanabe, K., Kakunaga, T. (1989) *Specific Inhibitors of Tyrosine-specific Protein Kinases: Properties of 4-hydroxycinnamamide derivatives in vitro.* Cancer Research, 49, 2374-2378.

Showalter, H. H. & Kraker, A. J. (1997) *Small molecule inhibitors of the platelet-derived growth factor receptor, the fibroblast growth factor receptor, and src family tyrosine kinases.* Pharmacology & Therapeutics, 76, 55-71.

Sicheri, F., Moarefi, I. & Kuriyan, J. (1997) *Crystal structure of the Src family tyrosine kinase Hck.* Nature, 385, 602-609.

Skordalakes, E., Tyrell, R., Elgendy, S., Goodwin, C. A., Green, D., Dodson, G., Scully, M. F., Freyssinet, J-M. H., Kakkar, V. V., Deadman, J. J. (1997) *Crystallographic Structures of Human α-Thrombin Complexed to Peptide Boronic Acids Lacking a Positive Charge at $P_1$. Evidence of Novel Interactions.* J. Am. Chem. Soc., 119, 9935-9936.

Snyder, H. R., Kuck, J. A., Johnson, J. R. (1938) J. Am. Chem. Soc., 60, 105.

Soloway, A. H., Whitman, B., Messer, J. R. (1962) J. Med. Pharm. Chem., 7, 640.

Soloway, A. H., Whitman, B., Messer, J. R. (1960) J. Pharmacology and Experimental Therapeutics, 129, 310-314.

Soloway, A. H. (1958) Science, 128, 1572.

Songyang, Z, Blechner, S., Hoagland, N., Hoekstra, M. F., Piwnica-Worms, H. & Cantley, L. C. (1994) *Use of an oriented peptide library to determine the optimal substrates of protein kinases.* Current Biology, 4, 973-982.

Songyang, Z., Carraway III, K. L., Eck, M. J., Harrison, S. C., Feldman, R. A., Mohammadl, M., Schlessinger, J., Hubbard, S. R., Smith, D. P., Eng. C., Lorenzo, J. J., Ponder, B. A. J., Mayer, B. J. & Cantley, L. C. (1995) *Protein tyrosine kinases and SH2 domains have overlapping specificities.* Nature, 373, 536-539.

Staley, C. A.; Parikh, N. U.; Gallick, G. E. (1997) *Cell Growth & Differentiation* 8(3), 269.

Stanwell, C., Burke, T. R. & Yuspa, S. H. (1995) *Erbstatin Analogue Methyl 2,5-dihydrocinnamate Cross-links Proteins and is Cytotoxic to Normal and Neoplastic Epithelial Cells by a Mechanism Independent of Tyrosine Kinase Inhibition.* Cancer Research, 55, 4950-4956.

Stanwell, C., Ye, B. & Burke, T. R. (1996) *Cell Protein Cross-linking by Erbstatin and Related Compounds.* Biochemical Pharmacology, 52, 475-480.

Takeshima, E.; Hamaguchi, M.; Watanbe, T.; Akiyama, S.; Kataoka, M.; Ohnishi, Y.; Xiao, H.; Hagai, Y., Taka, H. (1991) *Aberrant elevation of tyrosine-specific phosphorylation in human gastric cancer cells.* Japan J. Cancer Res., 82, 1428-1435.

Talamonti, M. S.; Roh, M. S.; Curley, S. A.; Gallick, G. E. (1993) *Increase in activity and level of pp60$^{c-src}$ in progressive stages of human colorectal cancer.* J. of Clinical Investigation, 91, 53-60.

Taniyama, K., Fujiwara, H., Kuno, T., Saito, N., Shuntoh, H., Sakaue, M. (1989) *Acute and subacute toxicity of 10B-paraboronophenylalanine.* Pigment Cell Research, 2, 291-296.

Taylor, S. J., Shalloway, D. (1996) *Src and the control of cell division.* Bioessays, 18, 9-11.

Taylor, S. S., Knighton, D. R., Zheng, J., Sowadski, J. M., Gibbs, C. S. & Zoller, M. J. (1993) *A template for the protein kinase family.* Trends in Biochemical Sciences, 18(3), 84-9.

Taylor, S. S., Radzio-Andzelm, E. (1994) *Three protein kinase structures define a common motif. Stucture,* 2, 345-355.

Thakkar, K., Geahlen, R. L., Cushman, M. (1993) *Synthesis and protein-tyrosine kinase inhibitory activity of polyhydroxylated stilbene analogs of piceatannol.* J. Med. Chem., 36, 2950-2955.

Weinberg, R. A. (1989) *Oncogenes, antioncogenes, and the molecular basis of multistep carcinogenesis.* Cancer Research, 49, 3713-3721.

Wolfe, J. P., Ahman, J., Sadighi, J. P., Singer, R. A., Buchwald, S. L. (1997) *An ammonia equivalent for the palladium-catalyzed amination of aryl halides and triflates.* Tet. Lett., 38, 6367-6370.

Wong, T. W. & Goldberg, A. R. (1984) *Kinetics and mechanism of angiotensin phosphorylation by the transforming gene product of Rous Sarcoma Virus.* J. Biol. Chem., 259, 3127-3131.

Xu, W., Harrison, S. C. & Eck, M. J. (1997) *Three-dimensional structure of the tyrosine kinase c-Src.* Nature, 385, 595-602.

Yamaguchi, H. & Hendrickson, W. A. (1996) *Structural basis for activation of human lymphocyte kinase Lck upon tyrosine phosphorylation.* Nature, 384, 484-489.

Yamamoto, T. (1993) *Molecular Basis of Cancer: Oncogenes and Tumor Suppresor Genes.* Microbiol. Immunol. 37, 11-22.

Zheng, J., Knighton, D. R., Ten Eyck, L. R., Karlsson, R., Xuong, N-H., Taylor, S. S. & Sowadski, J. M. (1993) *Crystal structure of the catalytic subunit of cAMP-dependent protein kinase complexed with MgATP and peptide inhibitor.* Biochemistry, 32, 2154-61.

Zhanpeisov, N. U., Otsuka, K. (1992) *Cluster quantum chemical study of the mechanism of selective oxidation of ethane to acetaldellyde on boron-phosphorous mixed oxide catalysts.* React. Kinet. Catal. Lett., 48, 301-308.

---

What is claimed:

1. A compound having the formula:

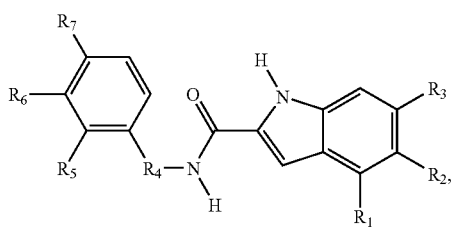

wherein $R_1$ is H or OH, $R_2$ is OH, $R_3$ is OH or H, and $R_4$ is $CH_2$, $CH_2CH_2$, $CH(CH_3)$ (R-configuration), $CH(CH_3)$ (S-configuration), or a bond, $R_5$ is $OCH_3$, H, or OH, $R_6$ is $OCH_3$, F, H, or OH, and $R_7$ is $OCH_3$, H, OH, $CO_2H$, $CO_2CH_3$, $CH_2CO_2H$, or $CH_2CO_2CH_3$, provided that one of $R^5$, $R^6$ or $R^7$ is not hydrogen and the remaining $R^5$, $R^6$ or $R^7$ are H.

2. The compound of claim 1, wherein the compound is selected from indole compounds

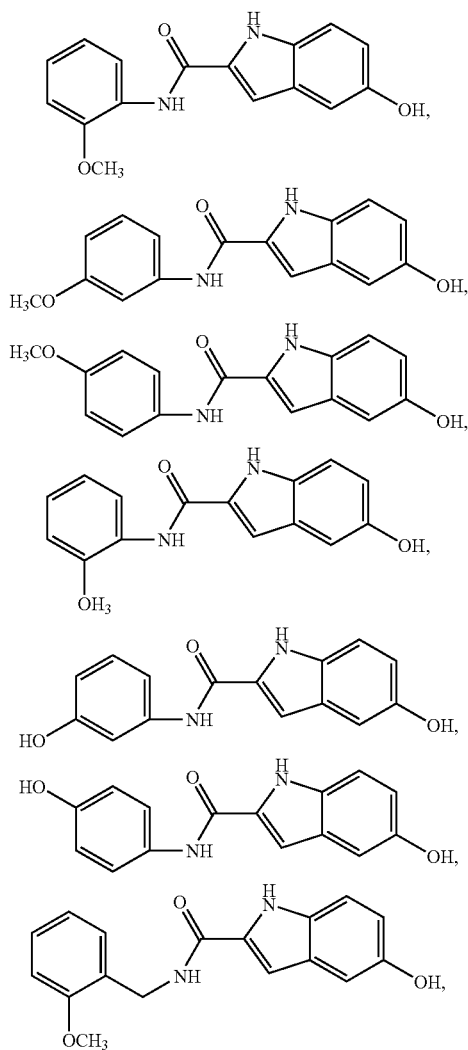

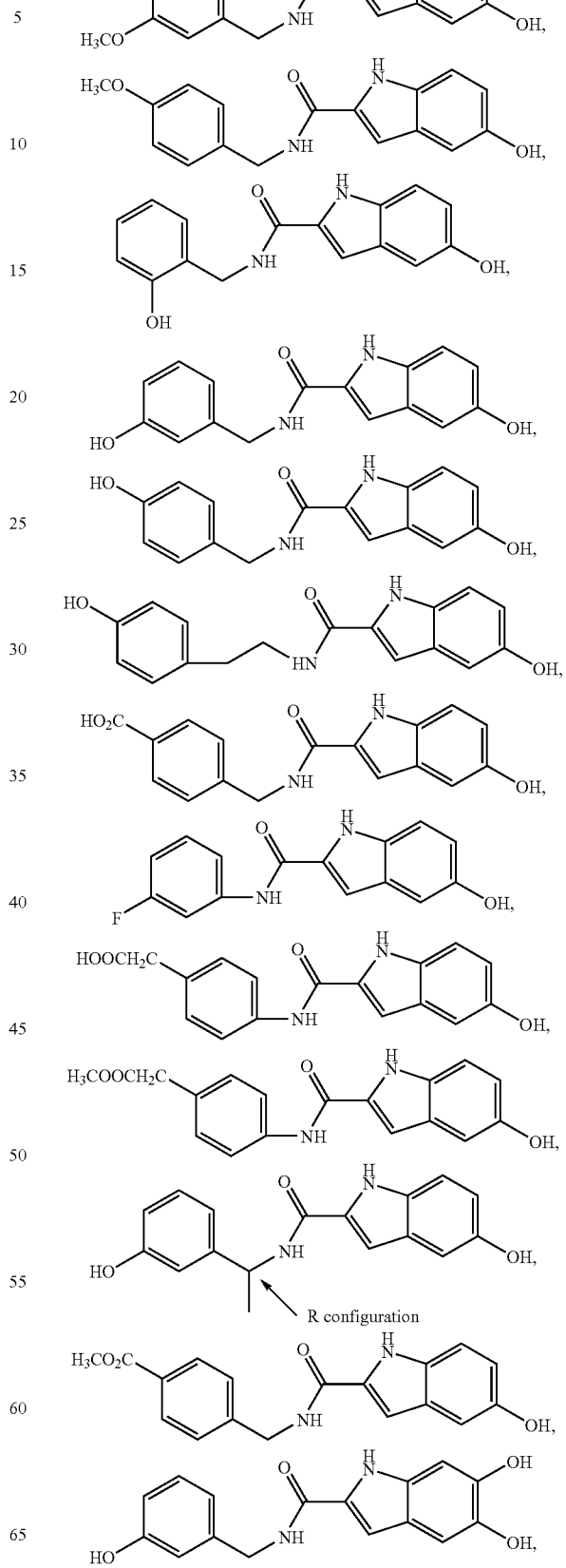

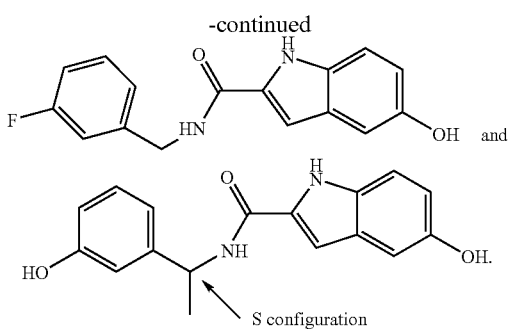 and
3. The compound of claim 1, wherein $R_1$ is H.
4. The compound of claim 1, wherein $R_3$ is H.
5. The compound of claim 1, wherein $R_5$ is $CH_2$.
6. The compound of claim 1, wherein $R_5$ is H.
7. The compound of claim 1, wherein $R_6$ is OH.
8. The compound of claim 1, wherein $R_7$ is H.
9. A compound having the structure:
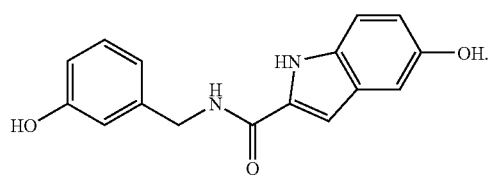
* * * * *

UNITED STATES PATENT AND TRADEMARK OFFICE
CERTIFICATE OF CORRECTION

PATENT NO. : 7,901,894 B2  
APPLICATION NO. : 11/261858  
DATED : March 8, 2011  
INVENTOR(S) : David G. Hangauer, Jr. et al.

Page 1 of 1

It is certified that error appears in the above-identified patent and that said Letters Patent is hereby corrected as shown below:

On the cover, sheet 1, the inventor's name "David G. Hangauer" should read --David G. Hangauer Jr.--.

On the Title Page:

The first or sole Notice should read --

Subject to any disclaimer, the term of this patent is extended or adjusted under 35 U.S.C. 154(b) by 324 days.

Column 71, lines 45-50, the chemical structure

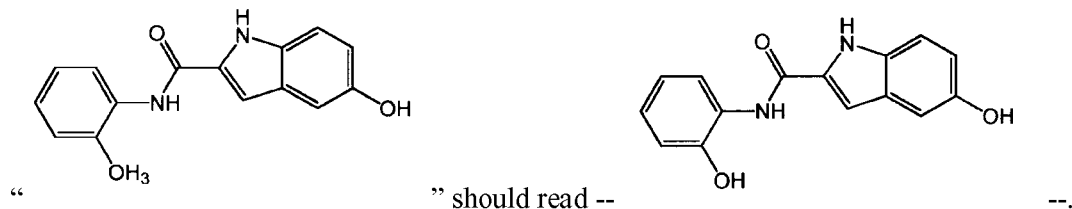

Column 74, line 1, the term "$R_5$" should read --$R_4$--.

Signed and Sealed this  
Ninth Day of August, 2011

David J. Kappos  
*Director of the United States Patent and Trademark Office*

SEQUENCE LISTING

```
<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: src
      substrate pentapeptide

<400> SEQUENCE: 1

Ile Tyr Gly Glu Phe
1               5

<210> SEQ ID NO 2
<211> LENGTH: 5
<212> TYPE: PRT
<213> ORGANISM: Artificial Sequence
<220> FEATURE:
<221> NAME/KEY: PEPTIDE
<222> LOCATION: (2)
<223> OTHER INFORMATION: Xaa in position 2 is modified Tyr.
<220> FEATURE:
<223> OTHER INFORMATION: Description of Artificial Sequence: src
      pentapeptide scaffold

<400> SEQUENCE: 2

Ile Xaa Gly Glu Phe
1               5

<210> SEQ ID NO 3
<211> LENGTH: 5
<212> TYPE: PRT
<213> ORGANISM: Artificial Sequence
<220> FEATURE:
<221> NAME/KEY: PEPTIDE
<222> LOCATION: (4)
<223> OTHER INFORMATION: Xaa in position 4 is modified Ala.
<220> FEATURE:
<223> OTHER INFORMATION: Description of Artificial Sequence: PKA
      pentapeptide scaffold
```

-continued

```
<400> SEQUENCE: 3

Arg Arg Gly Xaa Ile
 1               5

<210> SEQ ID NO 4
<211> LENGTH: 5
<212> TYPE: PRT
<213> ORGANISM: Artificial Sequence
<220> FEATURE:
<221> NAME/KEY: PEPTIDE
<222> LOCATION: (4)
<223> OTHER INFORMATION: Xaa in position 4 is Ala or modified Ala.
<220> FEATURE:
<223> OTHER INFORMATION: Description of Artificial Sequence: Boronic
      acid-containing PKA inhibitor

<400> SEQUENCE: 4

Arg Arg Gly Xaa Ile
 1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence:  Kemptamide

<400> SEQUENCE: 5

Leu Arg Arg Ala Ser Leu Gly
 1               5

<210> SEQ ID NO 6
<211> LENGTH: 7
<212> TYPE: PRT
<213> ORGANISM: Artificial Sequence
<220> FEATURE:
<221> NAME/KEY: MOD_RES
<222> LOCATION: (5)
<223> OTHER INFORMATION: Xaa in position 5 is ALA; PHOSPHORYLATION
<220> FEATURE:
<223> OTHER INFORMATION: Description of Artificial Sequence:
      Phosphorylated Kemptamide

<400> SEQUENCE: 6

Leu Arg Arg Ala Xaa Leu Gly
 1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence:  Peptide
      substrate for Src

<400> SEQUENCE: 7

Gly Ile Tyr Trp His His Tyr
 1               5
```